(12) United States Patent
Fischell et al.

(10) Patent No.: US 8,224,430 B2
(45) Date of Patent: Jul. 17, 2012

(54) BASELINE PROCESSING FOR A CARDIAC EVENT DETECTION SYSTEM

(75) Inventors: David R. Fischell, Fair Haven, NJ (US); Tim A. Fischell, Kalamazoo, MI (US); Jonathan Harwood, Rumson, NJ (US); Robert E. Fischell, Dayton, MD (US); Steven R. Johnson, Fair Haven, NJ (US); Bruce Hopenfeld, Oceanport, NJ (US); Michael Sasha John, Larchmont, NY (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 480 days.

(21) Appl. No.: 12/585,861

(22) Filed: Sep. 28, 2009

(65) Prior Publication Data

US 2010/0087745 A1 Apr. 8, 2010

Related U.S. Application Data

(60) Division of application No. 11/594,806, filed on Nov. 9, 2006, which is a continuation-in-part of application No. 10/853,058, filed on May 26, 2004, now Pat. No. 7,558,623, which is a continuation-in-part of application No. 10/642,245, filed on Aug. 18, 2003, now Pat. No. 8,038,624, which is a continuation-in-part of application No. 10/251,505, filed on Sep. 20, 2002, now Pat. No. 6,609,023.

(51) Int. Cl.
*A61N 1/00* (2006.01)
(52) U.S. Cl. ...................... 600/509; 600/517
(58) Field of Classification Search ............... 607/9–28; 600/508–528
See application file for complete search history.

(56) References Cited

U.S. PATENT DOCUMENTS

| 5,113,869 | A | 5/1992 | Nappholz et al. |
|---|---|---|---|
| 5,135,004 | A | 8/1992 | Adams et al. |
| 5,199,428 | A | 4/1993 | Obel et al. |
| 5,313,953 | A | 5/1994 | Yomtov et al. |
| 5,497,780 | A | 3/1996 | Zehender |
| 5,792,066 | A | 8/1998 | Kwong |
| 6,112,116 | A | 8/2000 | Fischell et al. |
| 6,128,526 | A | 10/2000 | Stadler et al. |
| 6,272,379 | B1 | 8/2001 | Fischell et al. |
| 6,368,284 | B1 | 4/2002 | Bardy |
| 6,442,432 | B2 | 8/2002 | Lee |
| 6,501,983 | B1 | 12/2002 | Natarajan et al. |
| 7,066,891 | B2 | 6/2006 | Stadler et al. |

OTHER PUBLICATIONS

Zimmerman, M., et al.; "On Improving the Classification of Myocardial Ischemia Using Holter ECG Data"; Computers in Cardiology; 2004, 31, pp. 377-380.
Kligfield, et al.; "Heart rate adjustment of ST segment depression for improved detection of coronary artery disease"; Circulation; 1989, vol. 79, No. 2, pp. 245-255.
Okin, et al.; "Recovery-Phase Patterns of St Segment Depression in the Heart Rate Domain"; Circulation; 1989, vol. 80, No. 3, pp. 533-541.

*Primary Examiner* — Scott Getzow
(74) *Attorney, Agent, or Firm* — Rosenberg, Klein & Lee

(57) ABSTRACT

A system for the detection of cardiac events occurring in a human patient is provided. At least two electrodes are included in the system for obtaining an electrical signal from a patient's heart. An electrical signal processor is electrically coupled to the electrodes for processing the electrical signal and a patient alarm means is further provided and electrically coupled to the electrical signal processor. The electrical signal is acquired in the form of electrogram segments, which are categorized according to heart rate, ST segment shift and type heart rhythm (normal or abnormal). Baseline electrogram segments are tracked over time.

10 Claims, 18 Drawing Sheets

BASELINE PROCESSING FOR A CARDIAC EVENT DETECTION SYSTEM

CROSS REFERENCE TO RELATED APPLICATIONS

This application is a Divisional Application of U.S. patent application Ser. No. 11/594,806, filed Nov. 9, 2006 which is a Continuation-In-Part of U.S. patent application Ser. No. 10/853,058, filed May 26, 2004 now U.S. Pat. No. 7,558,623, entitled "Means and Method for the Detection of Cardiac Events," which is a Continuation-In-Part of U.S. patent application Ser. No. 10/642,245, filed Aug. 18, 2003 now U.S. Pat. No. 8,038,624, entitled "System for the Detection of Cardiac Events," which is a Continuation-In-Part of U.S. patent application Ser. No. 10/251,505, filed Sep. 20, 2002, now U.S. Pat. No. 6,609,023.

FIELD OF USE

This invention is in the field of systems, including devices implanted within a human patient, for the purpose of automatically detecting the onset of a cardiac event.

BACKGROUND OF THE INVENTION

Heart disease is the leading cause of death in the United States. A heart attack (also known as an Acute Myocardial Infarction (AMI)) typically results from a thrombus that obstructs blood flow in one or more coronary arteries. AMI is a common and life-threatening complication of coronary heart disease. The sooner that perfusion of the myocardium is restored (e.g., with injection of a thrombolytic medication such as tissue plasminogen activator (tPA)), the better the prognosis and survival of the patient from the heart attack. The extent of damage to the myocardium is strongly dependent upon the length of time prior to restoration of blood flow to the heart muscle.

Myocardial ischemia is caused by a temporary imbalance of blood (oxygen) supply and demand in the heart muscle. It is typically provoked by physical activity or other causes of increased heart rate when one or more of the coronary arteries are obstructed by atherosclerosis. Patients will often (but not always) experience chest discomfort (angina) when the heart muscle is experiencing ischemia.

Acute myocardial infarction and ischemia may be detected from a patient's electrocardiogram (ECG) by noting an ST segment shift (i.e., voltage change) over a relatively short (less than 5 minutes) period of time. However, without knowing the patient's normal ECG pattern detection from standard 12 lead ECG can be unreliable. In addition, ideal placement of subcutaneous electrodes for detection of ST segment shifts as they would relate to a subcutaneously implanted device has not been explored in the prior art.

Fischell et al in U.S. Pat. Nos. 6,112,116 and 6,272,379 describe implantable systems for detecting the onset of acute myocardial infarction and providing both treatment and alarming to the patient. While Fischell et al discuss the detection of a shift in the S-T segment of the patient's electrogram from an electrode within the heart as the trigger for alarms; it may be desirable to provide more sophisticated detection algorithms to reduce the probability of false positive and false negative detection. In addition while these patents describe some desirable aspects of programming such systems, it may be desirable to provide additional programmability and alarm control features.

Although anti-tachycardia pacemakers and Implantable Cardiac Defibrillators (ICDs) can detect heart arrhythmias, none are currently designed to detect ischemia and acute myocardial infarction events independently or in conjunction with arrhythmias.

In U.S. Pat. Nos. 6,112,116 and 6,272,379 Fischell et al, discuss the storage of recorded electrogram and/or electrocardiogram data; however techniques to optimally store the appropriate electrogram and/or electrocardiogram data and other appropriate data in a limited amount of system memory are not detailed.

In U.S. Pat. No. 5,497,780 by M. Zehender, a device is described that has a "goal of eliminating . . . cardiac rhythm abnormality." To do this, Zehender requires exactly two electrodes placed within the heart and exactly one electrode placed outside the heart. Although multiple electrodes could be used, the most practical sensor for providing an electrogram to detect a heart attack would use a single electrode placed within or near to the heart.

Zehender's drawing of the algorithm consists of a single box labeled ST SIGNAL ANALYSIS with no details of what the analysis comprises. His only description of his detection algorithm is to use a comparison of the ECG to a reference signal of a normal ECG curve. Zehender does not discuss any details to teach an algorithm by which such a comparison can be made, nor does Zehender explain how one identifies the "normal ECG curve". Each patient will likely have a different "normal" baseline ECG that will be an essential part of any system or algorithm for detection of a heart attack or ischemia.

In addition, Zehender suggests that an ST signal analysis should be carried out every three minutes. It may be desirable to use both longer and shorter time intervals than 3 minutes so as to capture certain changes in ECG that are seen early on or later on in the evolution of an acute myocardial infarction. Longer observation periods will also be important to account for minor slowly evolving changes in the "baseline" ECG. Zehender has no mention of detection of ischemia having different normal curves based on heart rate. To differentiate from exercise induced ischemia and acute myocardial infarction, it may be important to correlate ST segment shifts with heart rate or R-R interval.

Finally, Zehender teaches that "if an insufficient blood supply in comparison to the reference signal occurs, the corresponding abnormal ST segments can be stored in the memory in digital form or as a numerical event in order to be available for associated telemetry at any time." Storing only abnormal ECG segments may miss important changes in baseline ECG. Thus it is desirable to store some historical ECG segments in memory even if they are not "abnormal".

The Reveal™ subcutaneous loop Holter monitor sold by Medtronic uses two case electrodes spaced by about 3 inches to record electrocardiogram information looking for arrhythmias. It has no real capability to detect ST segment shift and its high pass filtering would in fact preclude accurate detection of changes in the low frequency aspects of the heart's electrical signal. Also the spacing of the electrodes it too close together to be able to effectively detect and record ST segment shifts. Similarly, current external Holter monitors are primarily designed for capturing arrhythmia related signals from the heart.

Although often described as an electrocardiogram (ECG), the stored electrical signal from the heart as measured from electrodes within the body should be termed an "electrogram". The early detection of an acute myocardial infarction or exercise induced myocardial ischemia caused by an increased heart rate or exertion is feasible using a system that notes a change in a patient's electrogram. The portion of such a system that includes the means to detect a cardiac event is defined herein as a "cardiosaver" and the entire system including the cardiosaver and the external portions of the system is defined herein as a "guardian system."

Furthermore, although the masculine pronouns "he" and "his" are used herein, it should be understood that the patient or the medical practitioner who treats the patient could be a man or, a woman. Still further the term; "medical practitioner" shall be used herein to mean any person who might be involved in the medical treatment of a patient. Such a medical practitioner would include, but is not limited to, a medical doctor (e.g., a general practice physician, an internist or a cardiologist), a medical technician, a paramedic, a nurse or an electrogram analyst. A "cardiac event" includes an acute myocardial infarction, ischemia caused by effort (such as exercise) and/or an elevated heart rate, bradycardia, tachycardia or an arrhythmia such as atrial fibrillation, atrial flutter, ventricular fibrillation, and premature ventricular or atrial contractions (PVCs or PACs).

For the purpose of this invention, the term "electrocardiogram" is defined to be the heart electrical signals from one or more skin surface electrode(s) that are placed in a position to indicate the heart's electrical activity (depolarization and repolarization). An electrocardiogram segment refers to the recording of electrocardiogram data for either a specific length of time, such as 10 seconds, or a specific number of heart beats, such as 10 beats. For the purposes of this specification the PQ segment of a patient's electrocardiogram is the typically flat segment of a beat of an electrocardiogram that occurs just before the R wave.

For the purpose of this invention, the term "electrogram" is defined to be the heart electrical signals from one or more implanted electrode(s) that are placed in a position to indicate the heart's electrical activity (depolarization and repolarization). An electrogram segment refers to the recording of electrogram data for either a specific length of time, such as 10 seconds, or a specific number of heart beats, such as 10 beats. For the purposes of this specification the PQ segment of a patient's electrogram is the typically flat segment of an electrogram that occurs just before the R wave. For the purposes of this specification, the terms "detection" and "identification" of a cardiac event have the same meaning. A beat is defined as a sub-segment of an electrogram or electrocardiogram segment containing exactly one R wave.

Heart signal parameters are defined to be any. Heart signal parameters include PQ segment average value, ST segment average voltage value, R wave peak value, ST deviation, ST shift, average signal strength, T wave peak height, T wave average value, T wave deviation, heart rate, R-R interval and peak-to-peak voltage amplitude.

Heart rhythm parameters are defined to be any measured or calculated value created during the processing of one or more beats of electrogram data that pertain to heart rhythm. Heart rhythm parameters include R-R interval, ST segment duration and other single beat heart signal parameters, as well as parameters that classify multiple beats. For example, the frequency spectrum of a consecutive number of beats conveys information regarding the heart rhythm of those beats and is therefore a heart rhythm parameter.

SUMMARY OF THE INVENTION

The present invention is a system for the detection of cardiac events (a guardian system) that includes a device called a cardiosaver, and external equipment including a physician's programmer and an external alarm system. The present invention envisions a system for early detection of an acute myocardial infarction or exercise induced myocardial ischemia caused by an increased heart rate or exertion.

In the preferred embodiment of the present invention, the cardiosaver is implanted along with the electrodes. In an alternate embodiment, the cardiosaver and the electrodes could be external but attached to the patient's body. Although the following descriptions of the present invention in most cases refer to the preferred embodiment of an implanted cardiosaver processing electrogram data from implanted electrodes, the techniques described are equally applicable to the alternate embodiment where the external cardiosaver processes electrocardiogram data from skin surface electrodes.

In the preferred embodiment of the cardiosaver either or both subcutaneous electrodes or electrodes located on a pacemaker type right ventricular or atrial leads will be used. It is also envisioned that one or more electrodes may be placed within the superior vena cava. One version of the implanted cardiosaver device using subcutaneous electrodes would have an electrode located under the skin on the patient's left side. This could be best located between 2 and 20 inches below the patient's left arm pit. The cardiosaver case that would act as the indifferent electrode would typically be implanted like a pacemaker under the skin on the left side of the patient's chest.

Using one or more detection algorithms, the cardiosaver can detect a change in the patient's electrogram that is indicative of a cardiac event, such as an acute myocardial infarction, within five minutes after it occurs and then automatically warn the patient that the event is occurring. To provide this warning, the guardian system includes an internal alarm subsystem (internal alarm means) within the cardiosaver and/or an external alarm system (external alarm means). In the preferred, implanted embodiment, the cardiosaver communicates with the external alarm system using a wireless radio-frequency (RF) signal.

The internal alarm means generates an internal alarm signal to warn the patient. The internal alarm signal may be a mechanical vibration, a sound or a subcutaneous electrical tickle. The external alarm system (external alarm means) will generate an external alarm signal to warn the patient. The external alarm signal is typically a sound that can be used alone or in combination with the internal alarm signal. The internal or external alarm signals would be used to alert the patient to at least two different types of conditions (i.e. levels of severity): an "EMERGENCY ALARM" signaling the detection of a major cardiac event (e.g. a heart attack) and the need for immediate medical attention, and a less critical "SEE DOCTOR ALERT" (or alarm) signaling the detection of a less serious non life threatening condition such as exercise induced ischemia. The SEE DOCTOR alert signal would be used to tell the patient that he is not in immediate danger but should arrange an appointment with his doctor in the near future. In addition to the signaling of less critical cardiac events, the SEE DOCTOR alert signal could also signal the patient when the cardiosaver battery is getting low.

In the preferred embodiment, the internal EMERGENCY alarm signal would be applied periodically, for example, with three pulses every 5 seconds after the detection of a major cardiac event. It is also envisioned that the less critical SEE DOCTOR alert, would be signaled in a different way, such as one pulse every 7 seconds.

The external alarm system is a hand-held portable device that may include any or all of the following features:

1. an external alarm means to generate an external alarm signal to alert the patient.

2. the capability to receive cardiac event alarms, recorded electrogram and other data from the cardiosaver
3. the capability to transmit the cardiac event alarm, recorded electrogram and other data collected by the cardiosaver to a medical practitioner at a remote location.
4. an "alarm-off" or disable button that when depressed can acknowledge that the patient is aware of the alarm and will turn off internal and external alarm signals.
5. a display (typically an LCD panel) to provide information and/or instructions to the patient by a text message and the display of segments of the patient's electrogram.
6. the ability to provide messages including instructions to the patient via a pre-recorded human voice.
7. a patient initiated electrogram capture initiated by a "Panic Button" to allow the patient, even when there has been no alarm, to initiate transmission of electrogram data from the cardiosaver to the external alarm system for transmission to a medical practitioner.
8. a patient initiated electrogram capture to initiate transmission of electrogram data from the cardiosaver to the external alarm system for display to a medical practitioner using the display on the external alarm system.
9. the capability to automatically turn the internal and external alarms off after a reasonable (initial alarm-on) period that is typically less than 30 minutes if the alarm-off button is not used. This feature might also be implemented within the cardiosaver implant.

If the alarm disable button is not used by the patient to indicate acknowledgement of awareness of an EMERGENCY alarm, it is envisioned that instead of completely stopping all alarm signals to the patient after the first period of time which is an initial alarm-on period, a reminder alarm signal would be turned on for a second time period which is a reminder alarm on-period of time that would follow an off-period of time during which time the alarm signal is turned off.

The reminder alarm signal might be repeated periodically for a third longer time period which is a periodic reminder time period. Each of the repeated reminder alarm signals would last for the reminder alarm on-period and would be followed by an alarm off-period. The periodic reminder time period would typically be 3 to 5 hours because after three to five hours the patient's advantage in being alerted to seek medical attention for a severe cardiac event like an AMI is mostly lost. The alarm off-period between the periodic reminder alarm signals could either remain constant, increase or decrease over the periodic reminder time period. For example, after an initial alarm-on time period of five minutes a 30 second long reminder alarm signal might occur every 10 minutes for a periodic reminder time period of 3 hours, (i.e. the reminder alarm on-period is 30 seconds and the alarm off-period is 9 minutes and 30 seconds). It is also envisioned that the alarm off-period might change during the periodic reminder time period. For example, the off-period in the first hour of the periodic reminder time period might be 10 minutes increasing to 20 minutes in the last hour of the periodic reminder time period.

Text and/or spoken instructions may include a message that the patient should promptly take some predetermined medication such as chewing an aspirin, placing a nitroglycerine tablet under his tongue, inhaling or nasal spraying a single or multiple drug combination and/or injecting thrombolytic drugs into a subcutaneous drug port. The message may be a printed label or a context specific message displayed on a visual display such as a liquid crystal display (LCD). The messaging displayed by or spoken from the external alarm system and/or a phone call from a medical practitioner who receives the alarm could also inform the patient that he should wait for the arrival of emergency medical services or he should promptly proceed to an emergency medical facility. It is envisioned that the external alarm system can have direct connection to a telephone line and/or work through cell phone or other wireless networks.

The present invention also includes an embodiment of the external alarm system that includes a container for medications to be taken in the event of an EMERGENCY alarm. For example, the container might have aspirin, PLAVIX, or another clot reducing medication and nitroglycerine which is a vasodilator.

If a patient seeks care in an emergency room, the external alarm system could provide a display to the medical practitioners in the emergency room of both the electrogram segment that caused the alarm and the baseline electrogram segment against which the electrogram that caused the alarm was compared. The ability to display both baseline and alarm electrogram segments will significantly improve the ability of the emergency room physician to properly identify AMI.

A preferred embodiment of the external alarm system consists of an external alarm transceiver and a handheld computer. The external alarm transceiver having a standardized interface, such as Compact Flash adapter interface, a secure digital (SD) card interface, a multi-media card interface, a memory stick interface or a PCMCIA card interface. The standardized interface will allow the external alarm transceiver to connect into a similar standardized interface slot that is present in many handheld computers such as a Palm Pilot or Pocket PC. An advantage of this embodiment is that the handheld computer can cost effectively supply the capability for text and graphics display and for playing spoken messages.

Using a handheld computer, such as the Handspring Treo™, Blackberry or Thera™ by Audiovox™ that combines a Palm device or Pocket PC with having an SD/Multimedia interface slot with a cell phone having wireless internet access, is a solution that can easily be programmed to provide communication between the external alarm system and a diagnostic center staffed with medical practitioners.

The panic button feature, which allows a patient-initiated electrogram capture and transmission to a medical practitioner, will provide the patient with a sense of security knowing that, if he detects symptoms of a heart-related ailment such as left arm pain, chest pain or palpitations, he can get a fast review of his electrogram. Such a review would allow the diagnosis of arrhythmias, such as premature atrial or ventricular beats, atrial fibrillation, atrial flutter or other heart rhythm irregularities. The medical practitioner could then advise the patient what action, if any, should be taken. The guardian system would also be programmed to send an alarm in the case of ventricular fibrillation so that a caretaker of the patient could be informed to immediately provide a defibrillation electrical stimulus. This is practical as home defibrillation units are now commercially available. It is also possible that, in patients prone to ventricular fibrillation following a myocardial infarction, such a home defibrillator could be placed on the patient's chest to allow rapid defibrillation should ventricular fibrillation occur while waiting for the emergency medical services to arrive.

The physician's programmer provides the patient's doctor with the capability to set cardiosaver cardiac event detection parameters. The programmer communicates with the cardiosaver using the wireless communication capability that also allows the external alarm system to communicate with the cardiosaver. The programmer can also be used to upload and review electrogram data captured by the cardiosaver including electrogram segments captured before, during and after a cardiac event.

An extremely important capability of the present invention is the use of a continuously adapting cardiac event detection program that compares extracted features from a recently captured electrogram segment with the same features extracted from a baseline electrogram segment at a predetermined time in the past. For example, the thresholds for detecting an excessive ST shift would be appropriately adjusted to account for slow changes in electrode sensitivity or ST segment voltage levels over time. It may also be desirable to choose the predetermined time in the past for comparison to take into account daily cycles in the patient's heart electrical signals.

Thus, a preferred embodiment of the present invention would use a baseline for comparison that is an average of the baselines collected hourly over the approximately 24 hours prior to the electrogram segment being examined. Such a system would adapt to both minor (benign) slow changes in the patient's baseline electrogram as well as any daily cycle.

Use of a system that adapts to slowly changing baseline conditions is of great importance in the time following the implantation of electrode leads in the heart. This is because there can be a significant "injury current" present just after implantation of an electrode and for a time of up to a month, as the implanted electrode heals into the wall of the heart. Such an injury current may produce a depressed ST segment that deviates from a normal isoelectric electrogram where the PQ and ST segments are at approximately the same voltage. Although the ST segment may be depressed due to this injury current, the occurrence of an acute myocardial infarction can still be detected since an acute myocardial infarction will still cause a significant shift from this "injury current" ST baseline electrogram. Alternately, the present invention might be implanted and the detector could be turned on after healing of the electrodes into the wall of the heart. This healing would be noted in most cases by the evolution to an isoelectric electrogram (i.e., PQ and ST segments with approximately the same voltages).

The present invention's ST detection technique involves recording and processing baseline electrogram segments to calculate the threshold for myocardial infarction and/or ischemia detection. These baseline electrogram segments would typically be collected, processed and stored once an hour or with any other appropriate time interval. It is important to the function of the present invention that baseline segments represent a "normal" electrogram for the patient's heart where the heart rate is in the "normal" range and the beats are not irregular nor do the exhibit excessive ST shift. During collection of baseline segments, the present invention will assess if the segment selected meets the normalcy requirements. If it does not, the present invention will try to use the next collected electrogram segment as the baseline. If this too is not normal, the present invention will keep trying for a preset period of time to collect a baseline after which it will note the inability to collect a baseline, keep the previous baseline for future detection and wait for the next baseline collection time interval and try to collect the next baseline. A very important feature of the present invention is the ability to identify the inability to collect any baselines over a specified time period and alert the patient to this event. This alert could indicate that the device is malfunctioning, the lead is no longer properly connected or the patient's heart is not producing "normal" electrogram signals. For example, the patient's heart rate could be elevated over the specified time period due to the patient's failure to take his beta blocker medication.

In addition to patient alerting, the reason for the inability to find a baseline may be stored in a "bad baseline" log.

If a suitable baseline for any particular time slot has not been changed over a selected time period due to a persistent inability to find a good baseline for that time slot, the baseline for that time slot may be set to a default value.

The present invention supports the capability to program the default baseline values at any time. Additionally, baseline updating may be turned off, such that the default baseline values are always used as the baselines. This feature may be helpful in various situations, for example in the case where a person's QRS complex is very irregular and/or frequently changes.

A preferred embodiment of the present invention would save and process a 10 second baseline electrogram segment once every hour. Every 30 seconds the cardiosaver would save and process a 10 second long recent electrogram segment. The cardiosaver would compare the recent electrogram segment with an average of the 24 most recent baseline electrogram segments that were set hourly over the preceding approximately 24 hour period.

The processing of each of the hourly baseline electrogram segments would involve calculating the average electrogram signal strength as well as calculating the average "ST deviation". The ST deviation for a single beat of an electrogram segment is defined to be the difference between the average ST segment voltage and the average PQ segment voltage. The average ST deviation of the baseline electrogram segment is the average of the ST deviation of multiple (at least two) beats within the baseline electrogram segment.

The following detailed description of the drawings fully describes how the ST and PQ segments are measured and averaged.

An important aspect of the present invention is the capability to adjust the location in time and duration of the ST and PQ segments used for the calculation of ST shifts. The present invention is initially programmed with the time interval between peak of the R wave of a beat and the start of the PQ and ST segments of that beat set for the patient's normal heart rate. As the patient's heart rate changes during daily activities, the present invention will adjust these time intervals for each beat proportional to the R-R interval for that beat. In other words, if the R-R interval shortens (higher heart rate) then the ST and PQ segments would move closer to the R wave peak and would become shorter. ST and PQ segments of a beat within an electrogram segment are defined herein as sub-segments of the electrogram segment. Specifically, the time interval between the R wave and the start of the ST and PQ segments may be adjusted in proportion to the R-R interval or alternately by the square root of the R-R interval. It is preferable in all cases to base these times on the R-R interval from the beat before the current beat. As calculating the square root is a processor intensive calculation, the preferred implementation of this feature is best done by pre-calculating the values for the start of PQ and ST segments during programming and loading these times into a simple lookup table where for each R-R interval, the start times and/or durations for the segments is stored.

It is envisioned that a combination of linear and square root techniques could be used where both the time interval between the R wave and the start of the ST segment ($T_{ST}$) and the duration of the ST segment ($D_{ST}$) are proportional to the square root of the R-R interval, while the time interval between the R wave and the start of the PQ segment ($T_{PQ}$) and the duration of the PQ segment ($D_{PQ}$) are linearly proportional to the R-R interval.

It is also envisioned that the patient would undergo a stress test following implant, the electrogram data collected would be transmitted to the physician's programmer and the parameters $T_{ST}$, $D_{ST}$, $T_{PQ}$ and $D_{PQ}$ would be automatically selected by the programmer based on the electrogram data from the stress test. The data from the stress test would cover each of the heart rate ranges and could also be used by the programmer to generate excessive ST shift detection thresholds for each of the heart rate ranges. In each heart rate range of the implant the detection threshold would typically be set based on the mean and standard deviation of the ST shifts seen during the stress test. For example, one could set the detection threshold for each heart rate range to the value of the mean ST shift plus or minus a multiple (e.g. three) times the standard deviation. In each case where the programmer can automatically select parameters for the ST shift detection algorithm, a manual override would also be available to the medical practitioner. Such an override is of particular importance as it allows adjustment of the algorithm parameters to compensate for missed events or false positive detections.

The difference between the ST deviation on any single beat in a recently collected electrogram segment and a baseline average ST deviation extracted from a baseline electrogram segment is defined herein as the "ST shift" for that beat. The present invention envisions that detection of acute myocardial infarction and/or ischemia would be based on comparing the ST shift of one or more beats with a predetermined detection threshold "$H_{ST}$".

In U.S. application Ser. No. 10/051,743 that is incorporated herein by reference, Fischell describes a fixed threshold for detection that is programmed by the patient's doctor. The present invention envisions that the threshold should rather be based on some percentage "$P_{ST}$" of the average signal strength extracted from the baseline electrogram segment where $P_{ST}$ is a programmable parameter of the cardiosaver device. The "signal strength" can be measured as peak-to-peak signal voltage, RMS signal voltage or as some other indication of signal strength such as the difference between the average PQ segment amplitude and the peak R wave amplitude.

Similarly, it is envisioned that the value of $P_{ST}$ might be adjusted as a function of heart rate so that a higher threshold could be used if the heart rate is elevated, so as to not trigger on exercise that in some patients will cause minor ST segment shifts when there is not a heart attack occurring. Alternately, lower thresholds might be used with higher heart rates to enhance sensitivity to detect exercise-induced ischemia. One embodiment of the present invention has a table stored in memory where values of $P_{ST}$ for a preset number of heart rate ranges, (e.g. 50-80, 81-90, 91-100, 101-120, 121-140) might be stored for use by the cardiosaver detection algorithm in determining if an acute myocardial infarction or exercise induced ischemia is present.

Thus it is envisioned that the present invention would use the baseline electrogram segments in 3 ways.
1. To calculate a baseline average value of a feature such as ST segment voltage or ST deviation that is then subtracted from the value of the same feature in recently captured electrogram segments to calculate the shift in the value of that feature. E.g. the baseline average ST deviation is subtracted from the amplitude of the ST deviation on each beat in a recently captured electrogram segment to yield the ST shift for that beat.
2. To provide an average signal strength used in calculating the threshold for detection of a cardiac event. This will improve detection by compensating for slow changes in electrogram signal strength over relatively long periods of time.
3. To provide a medical practitioner with information that will facilitate diagnosis of the patient's condition. For example, the baseline electrogram segment may be transmitted to a remotely located medical practitioner and/or displayed directly to a medical practitioner in the emergency room.

For the purposes of the present invention, the term adaptive detection algorithm is hereby defined as a detection algorithm for a cardiac event where at least one detection-related threshold adapts over time so as to compensate for relatively slow (longer than an hour) changes in the patient's normal electrogram.

The present invention might also include an accelerometer built into the cardiosaver where the accelerometer is an activity sensor used to discriminate between elevated heart rate resulting from patient activity as compared to other causes.

It is also envisioned that the present invention could have specific programming to identify a very low heart rate (bradycardia) or a very high heart rate (tachycardia or fibrillation). While a very low heart rate is usually not of immediate danger to the patient, its persistence could indicate the need for a pacemaker. As a result, the present invention could use the "SEE DOCTOR" alert along with an optional message sent to the external alarm system to alert the patient that his heart rate is too low and that he should see his doctor as soon as convenient. On the other hand, a very high heart rate can signal immediate danger thus it would be desirable to initiate an EMERGENCY in a manner similar to that of acute myocardial infarction detection. What is more, detections of excessive ST shift during high heart rates may be difficult and if the high heart rate is the result of a heart attack then it is envisioned that the programming of the present invention would use a major event counter that would turn on the alarm if the device detects a combination of excessive ST shift and overly high heart rate.

Another early indication of acute myocardial infarction is a rapid change in the morphology of the T wave. Unfortunately, there are many non-AMI causes of changes in the morphology of a T wave. However, these changes typically occur slowly while the changes from an AMI occur rapidly. Therefore one embodiment of this invention uses detection of a change in the T wave as compared to a baseline collected a short time (less than 30 minutes) in the past. The best embodiment is probably using a baseline collected between 1 and 5 minutes in the past. Such a T wave detector could look at the amplitude of the peak of the T wave. An alternate embodiment of the T wave detector might look at the average value of the entire T wave as compared to the baseline. The threshold for T wave shift detection, like that of ST shift detection, can be a percentage $P_T$ of the average signal strength of the baseline electrogram segment. $P_T$ could differ from $P_{ST}$ if both detectors are used simultaneously by the cardiosaver.

In its simplest form, the "guardian system" includes only the cardiosaver and a physician's programmer. Although the cardiosaver could function without an external alarm system where the internal alarm signal stays on for a preset period of time, the external alarm system is highly desirable. One reason it is desirable is the button on the external alarm system that provides the means for of turning off the alarm in either or both the implanted device (cardiosaver) and the external alarm system. Another very important function of the external alarm system is to facilitate display of both the baseline and alarm electrogram segments to a treating physician to facilitate rapid diagnosis and treatment for the patient.

As an implantable device, the present invention cardiosaver must conserve power to allow a reasonable lifetime in a cosmetically acceptable package size. In U.S. Pat. No. 6,609,023, Fischell et al describe how the cardiosaver collects and processes electrogram data for a first predetermined, "segment time period" (e.g. 10 seconds) to look for a cardiac event and then going to a lower power usage sleep state for a second predetermined "sleep state time period" (e.g. 20 seconds). Although it is desirable to look for cardiac events every 30 seconds as described by Fischell et al, it is possible to decrease the use of electrical power by extending the time duration of the sleep state time period to be greater than 20 seconds. Extending implant lifetime by decreasing electrical power usage can be accomplished by utilizing a longer time duration for the sleep state time period to be (for example) on the order of 50 to 80 seconds.

While a 50 to 80 sleep state time period with a 10 second time duration for the segment time period of data collection would increase the life of the implant, the total cycle times of 60 to 90 seconds is a comparatively long time to wait if cardiac events are to be quickly detected. The present invention cardiosaver utilizes an adaptive cycle time where the sleep state time period following detection of an "abnormal" electrogram segment is shorter than the sleep state time period following detection of an electrogram segment that has no detected abnormality. For example, the sleep state time period could be 80 seconds following an electrogram segment where no abnormality is detected and 20 seconds following an electrogram segment where any abnormality (e.g. excessive ST shift or arrhythmia) is detected. In this way, the function during any irregularity of heart signal would be the same as the Fischell et al. cardiosaver, yet significant power savings would be created during normal functioning of the heart.

It is also envisioned that the sleep state time period could be even more adaptive so that the length of the sleep state time might be related to the number of successive normal (no abnormality detected) electrogram segments. For example, one normal segment would be followed by a sleep state time period of 40 seconds, two normal segments by 50 seconds, 3 normal segments by 80 seconds, and 4 or more normal segments by 110 seconds. There would typically be a maximum sleep state time period used during long periods when all electrogram segments are normal and a minimum sleep time period that would be used following any detected abnormality. The maximum and minimum sleep times could be preset or programmable.

An abnormal electrogram segment is an electrogram segment where one or more heart signal parameters extracted during the processing of the electrogram segment by the cardiosaver meets the criteria for an abnormal electrogram segment. The criteria for an abnormal electrogram segment can be the same criteria used for detecting a cardiac event within the electrogram segment. It is also envisioned that the criteria for detecting an abnormal electrogram segment could be less stringent that the criteria for detecting a cardiac event. For example, an abnormal segment might be detected using a threshold lower by a preset percentage (e.g. 50%) than the respective threshold for the indication of a cardiac event. In this way, the time to detection of the event might be reduced by getting to the shorter sleep time more quickly.

It is also highly desirable for the present invention guardian system to allow real time or near real time display of electrogram data for diagnostic purposes. Such a display could be of great value in an emergency setting where fast review of the patient's current heart signal is important. In a real time mode, the cardiosaver 5 of FIG. 1 would simultaneously collect and transmit electrogram data to the external equipment 7 of FIG. 1.

In the near real time mode, the cardiosaver 5 would collect an electrogram segment, process the electrogram segment looking for abnormalities and then transmit the segment to the external equipment 7. A typical cycle time for the near real time mode would be 15 seconds including 10 seconds for electrogram segment collection, 1 second for processing and 4 seconds for transmission to the external equipment 7. The results of the processing might also be transmitted along with the segment.

It may be very important to differentiate positive ST shifts (elevation) of the electrogram from negative ST shifts (depression) and also separately differentiate these conditions based on heart rate. In fact, there are four separate detectable conditions as follows:

1. Excessive ST elevation at normal heart rate
2. Excessive ST depression at normal heart rate
3. Excessive ST elevation at elevated heart rate
4. Excessive ST depression at elevated heart rate While ST depression at elevated heart rate is the well known indication of sub-endocardial ischemia and ST elevation at normal heart rate is typically an indication of transmural ischemia it is not as clear as to the cause of excessive ST depression at normal heart rate or excessive ST elevation at an elevated heart rate. For example, excessive ST depression at normal heart rate could be the result of sub-endocardial ischemia from a partial occlusion of a coronary artery or it could be the result of transmural ischemia from a total occlusion (this is sometimes referred to as upside down ST elevation). It is also possible that an excessive ST shift at normal heart rates can be seen in the 10 minute period following an interval of elevated heart rate. As transmural ischemia is a much more dangerous condition, and one should not send a patient to the emergency room if the patient's condition is not a dangerous one, it is important to be able to have techniques in the present invention ST shift algorithm to allow the algorithm to properly classify the cardiac event in any of the above 4 conditions.

The present invention ST shift algorithm does this in several ways. First, the detection thresholds for all 4 conditions are separately programmable so that one could have a larger shift threshold for conditions 2, 3 or 4 than that of condition 1. Next one can require a different ST shift duration or persistence time for the different conditions. For example, excessive ST elevation at normal heart rate might only require 2 minutes of ST shift duration while excessive ST depression at elevated heart rate could require 15 minutes of ST shift duration for an event detection. Finally, to properly classify excessive ST shifts at normal heart rate the algorithm could extend any period of elevated heart rate by a time window that would classify any ST shift in the window as being at an elevated heart rate, even if the heart rate drops into a normal range.

Thus it is an object of this invention is to have a cardiosaver designed to detect the occurrence of a cardiac event by comparing baseline electrogram data from a first predetermined time with recent electrogram data from a second predetermined time.

Another object of the present invention is to have a Guardian system where the electrogram data collected during a preset period (such as during a stress test) is used by the programmer to automatically select detection parameters for the ST shift detection algorithm.

Another object of the present invention is to have a Guardian system with at least two levels of severity of patient alarm/alerting where the more severe EMERGENCY alarm alerts the patient to seek immediate medical attention.

Another object of the present invention is to have a cardiac event detected by comparing at least one heart signal parameter extracted from an electrogram segment captured at a first predetermined time by an implantable cardiosaver with the same at least one heart signal parameter extracted from an electrogram segment captured at a second predetermined time.

Another object of the present invention is to have acute myocardial infarction detected by comparing recent electrogram data to an average of baseline electrogram data that is collected periodically (e.g. once an hour) over a certain amount of time (e.g. one day). A related object of this invention is to create a plurality of baseline time slots (e.g. 24 time slots for an hourly period over one day) for which corresponding baseline electrogram data is stored.

Another object of the present invention is to have acute myocardial infarction detected by comparing the ST deviation of the beats in a recently collected electrogram segment to the average ST deviation of two or more beats of a baseline electrogram segment.

Another object of the present invention is to have acute myocardial infarction detected by comparing the ST segment voltage of the beats in a recently collected electrogram segment to the average ST segment voltage of two or more beats of a baseline electrogram segment.

Another object of the present invention is to have the threshold(s) for detecting the occurrence of a cardiac event adjusted by a cardiosaver device to compensate for slow changes in the average signal level of the patient's electrogram.

Another object of the present invention is to have the threshold for detection of a cardiac event adjusted by a cardiosaver device to compensate for daily cyclic changes in the average signal level of the patient's electrogram.

Another object of the present invention is to have an external alarm system including an alarm off button that will turn off either or both internal and external alarm signals initiated by an implanted cardiosaver.

Another object of the present invention is to have the alarm signal generated by a cardiosaver automatically turn off after a preset period of time.

Still another object of this invention is to use the cardiosaver to warn the patient that an acute myocardial infarction has occurred by means of a subcutaneous vibration.

Still another object of this invention is to have the cardiac event detection require that at least a majority of the beats exhibit an excessive ST shift before identifying an acute myocardial infarction.

Still another object of this invention is to have the cardiac event detection require that excessive ST shift still be present in at least two electrogram segments separated by a preset period of time.

Still another object of this invention is to have the cardiac event detection require that excessive ST shift still be present in at least three electrogram segments separated by preset periods of time.

Yet another object of the present invention is to have a threshold for detection of excessive ST shift that is dependent upon the average signal strength calculated from a baseline electrogram segment.

Yet another object of the present invention is to have a threshold for detection of excessive ST shift that is a function of the difference between the average PQ segment amplitude and the R wave peak amplitude of a baseline electrogram segment.

Yet another object of the present invention is to have a threshold for detection of excessive ST shift that is a function of the average minimum to maximum (peak-to-peak) voltage for at least two beats calculated from a baseline electrogram segment.

Yet another object of the present invention is to have the ability to detect a cardiac event by the shift in the amplitude of the T wave of an electrogram segment at a second predetermined time as compared with the average baseline T wave amplitude from a baseline electrogram segment at a first predetermined time.

Yet another object of the present invention is to have the ability to detect a cardiac event by the shift in the T wave deviation of at least one beat of an electrogram segment at a second predetermined time as compared with the average baseline T wave deviation from an electrogram segment at a first predetermined time.

Yet another object of the present invention is to have the first and second predetermined times for T wave amplitude and/or deviation comparison be separated by less than 30 minutes.

Yet another object of the present invention is to have the baseline electrogram segment used for ST segment shift detection and the baseline electrogram segment used for T wave shift detection be collected at different times.

Yet another object of the present invention is to have an initial alarm-on patient alerting period followed by a reminder alarm that periodically cycles on and off over a periodic reminder alarm period.

Yet another object of the present invention is to have an individualized (patient specific) "normal" heart rate range such that the upper and lower limits of "normal" are programmable using the cardiosaver programmer.

Yet another object of the present invention is to have one or more individualized (patient specific) "elevated" heart rate ranges such that the upper and lower limits of each "elevated" range are programmable using the cardiosaver programmer.

Yet another object of the present invention is to allow the threshold for detection of an excessive ST shift be different for the "normal" heart rate range as compared to one or more "elevated" heart rate ranges.

Yet another object of the present invention is to allow real time or near real time display of electrogram data for diagnostic purposes.

Yet another object of the present invention is to have the time period between collections of electrogram data vary, where the time period is lengthened when the electrogram is normal and shortened when the electrogram is abnormal.

Yet another object of the present invention is to have different criteria for the normal/abnormal electrogram decision that influences the time period between collections of electrogram data as compared with the criteria for detecting a cardiac event.

Yet another object of the present invention is to be able to identify the inability to collect a normal baseline electrogram segment over a baseline alert time period and if so identified, use the alerting capabilities of the present invention to alert the patient to seek medical attention.

Yet another object of the present invention is to be able to identify the inability to collect a normal baseline electrogram segment for a particular baseline time slot and if so, use a preselected baseline electrogram for that time slot.

Yet another object of the present invention is to detect.

These and other objects and advantages of this invention will become obvious to a person of ordinary skill in this art upon reading of the detailed description of this invention including the associated drawings as presented herein.

DETAILED DESCRIPTION OF THE INVENTION

Figure 1:
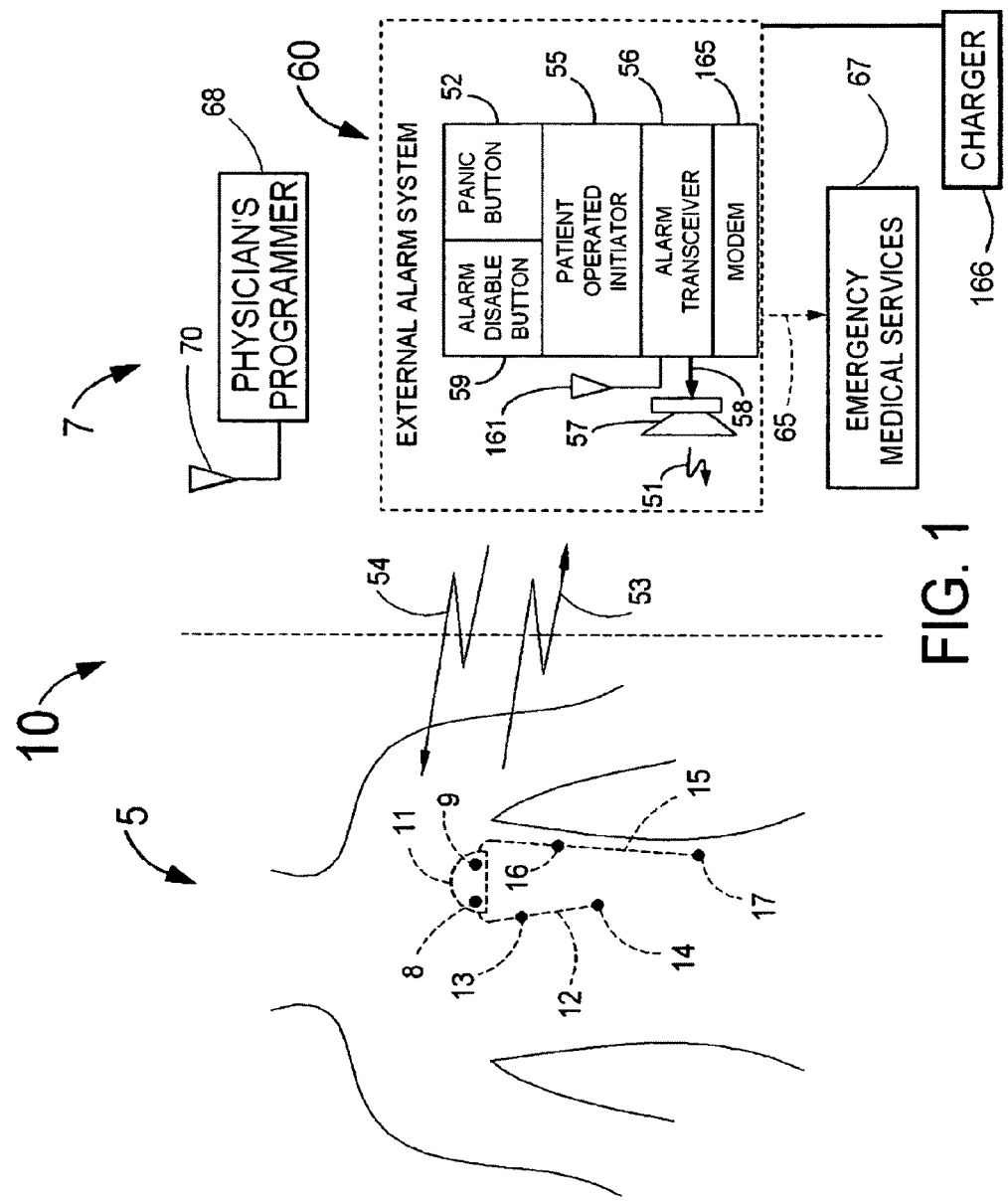
FIG. 1 illustrates a guardian system for the detection of a cardiac event and for warning the patient that a cardiac event is occurring.

FIG. 1 illustrates one embodiment of the guardian system 10 consisting of an implanted cardiosaver 5 and external equipment 7. The battery powered cardiosaver 5 contains electronic circuitry that can detect a cardiac event such as an acute myocardial infarction or arrhythmia and warn the patient when the event occurs. The cardiosaver 5 can store the patient's electrogram for later readout and can send wireless signals 53 to and receive wireless signals 54 from the external equipment 7. The functioning of the cardiosaver 5 will be explained in greater detail with the assistance of FIG. 4.

The cardiosaver 5 has two leads 12 and 15 that have multi-wire electrical conductors with surrounding insulation. The lead 12 is shown with two electrodes 13 and 14. The lead 15 has subcutaneous electrodes 16 and 17. In fact, the cardiosaver 5 could utilize as few as one lead or as many as three and each lead could have as few as one electrode or as many as eight electrodes. Furthermore, electrodes 8 and 9 could be placed on the outer surface of the cardiosaver 5 without any wires being placed externally to the cardiosaver 5.

The lead 12 in FIG. 1 could advantageously be placed through the patient's vascular system with the electrode 14 being placed into the apex of the right ventricle. The lead 12 with electrode 13 could be placed in the right ventricle or right atrium or the superior vena cava similar to the placement of leads for pacemakers and Implantable Coronary Defibrillators (ICDs). The metal case 11 of the cardiosaver 5 could serve as an indifferent electrode with either or both electrodes 13 and/or 14 being active electrodes. It is also conceived that the electrodes 13 and 14 could be used as bipolar electrodes. Alternately, the lead 12 in FIG. 1 could advantageously be placed through the patient's vascular system with the electrode 14 being placed into the apex of the left ventricle. The electrode 13 could be placed in the left atrium.

The lead 15 could advantageously be placed subcutaneously at any location where the electrodes 16 and/or 17 would provide a good electrogram signal indicative of the electrical activity of the heart. Again for this lead 15, the case 11 of the cardiosaver 5 could be an indifferent electrode and the electrodes 16 and/or 17 could be active electrodes or electrodes 16 and 17 could function together as bipolar electrodes. The cardiosaver 5 could operate with only one lead and as few as one active electrode with the case of the cardiosaver 5 being an indifferent electrode. The guardian system 10 described herein can readily operate with only two electrodes.

One embodiment of the cardiosaver device 5 using subcutaneous lead 15 would have the electrode 17 located under the skin on the patient's left side. This could be best located between 2 and 20 inches below the patient's left arm pit. The cardiosaver case 11 could act as the indifferent electrode and would typically be implanted under the skin on the left side of the patient's chest.

FIG. 1 also shows the external equipment 7 that consists of a physician's programmer 68 having an antenna 70, an external alarm system 60 including a charger 166. The external equipment 7 provides means to interact with the cardiosaver 5. These interactions include programming the cardiosaver 5, retrieving data collected by the cardiosaver 5 and handling alarms generated by the cardiosaver 5.

The purpose of the physician's programmer 68 shown in FIG. 1 is to set and/or change the operating parameters of the implantable cardiosaver 5 and to read out data stored in the memory of the cardiosaver 5 such as stored electrogram segments. This would be accomplished by transmission of a wireless signal 54 from the programmer 68 to the cardiosaver 5 and receiving of telemetry by the wireless signal 53 from the cardiosaver 5 to the programmer 68. When a laptop computer is used as the physician's programmer 68, it would require connection to a wireless transceiver for communicating with the cardiosaver 5. Such a transceiver could be connected via a standard interface such as a USB, serial or parallel port or it could be inserted into the laptop's PCMCIA card slot. The screen on the laptop would be used to provide guidance to the physician in communicating with the cardiosaver 5. Also, the screen could be used to display both real time and stored electrograms that are read out from the cardiosaver 5.

In FIG. 1, the external alarm system 60 has a patient operated initiator 55, an alarm disable button 59, a panic button 52, an alarm transceiver 56, an alarm speaker 57 and an antenna 161 and can communicate with emergency medical services 67 with the modem 165 via the communication link 65.

If a cardiac event is detected by the cardiosaver 5, an alarm message is sent by a wireless signal 53 to the alarm transceiver 56 via the antenna 161. When the alarm is received by the alarm transceiver 56 a signal 58 is sent to the loudspeaker 57. The signal 58 will cause the loudspeaker to emit an external alarm signal 51 to warn the patient that an event has occurred. Examples of external alarm signals 51 include a periodic buzzing, a sequence of tones and/or a speech message that instructs the patient as to what actions should be taken. Furthermore, the alarm transceiver 56 can, depending upon the nature of the signal 53, send an outgoing signal over the link 65 to contact emergency medical services 67. When the detection of an acute myocardial infarction is the cause of the alarm, the alarm transceiver 56 could automatically notify emergency medical services 67 that a heart attack has occurred and an ambulance could be sent to treat the patient and to bring him to a hospital emergency room.

If the remote communication with emergency medical services 67 is enabled and a cardiac event alarm is sent within the signal 53, the modem 165 will establish the data communications link 65 over which a message will be transmitted to the emergency medical services 67. The message sent over the link 65 may include any or all of the following information: (1) a specific patient is having an acute myocardial infarction or other cardiac event, (2) the patient's name, address and a brief medical history, (3) a map and/or directions to where the patient is located, (4) the patient's stored electrogram including baseline electrogram data and the specific electrogram segment that generated the alarm (5) continuous real time electrogram data, and (6) a prescription written by the patient's personal physician as to the type and amount of drug to be administered to the patient in the event of a heart attack. If the emergency medical services 67 includes an emergency room at a hospital, information can be transmitted that the patient has had a cardiac event and should be on his way to the emergency room. In this manner the medical practitioners at the emergency room could be prepared for the patient's arrival.

The communications link 65 can be either a wired or wireless telephone connection that allows the alarm transceiver 56 to call out to emergency medical services 67. The typical external alarm system 60 might be built into a Pocket PC or Palm Pilot PDA where the alarm transceiver 56 and modem 165 are built into insertable cards having a standardized interface such as compact flash cards, PCMCIA cards, multimedia, memory stick or secure digital (SD) cards. The modem 165 can be a wireless modem such as the Sierra AirCard 300 or the modem 165 may be a wired modem that connects to a standard telephone line. The modem 165 can also be integrated into the alarm transceiver 56.

The purpose of the patient operated initiator 55 is to give the patient the capability for initiating transmission of the most recently captured electrogram segment from the cardiosaver 5 to the external alarm system 60. This will enable the electrogram segment to be displayed for a medical practitioner.

Once an internal and/or external alarm signal has been initiated, depressing the alarm disable button 59 will acknowledge the patient's awareness of the alarm and turn off the internal alarm signal generated within the cardiosaver 5 and/or the external alarm signal 51 played through the speaker 57. If the alarm disable button 59 is not used by the patient to indicate acknowledgement of awareness of a SEE DOCTOR alert or an EMERGENCY alarm, it is envisioned that the internal and/or external alarm signals would stop after a first time period (an initial alarm-on period) that would be programmable through the programmer 68.

For EMERGENCY alarms, to help prevent a patient ignoring or sleeping through the alarm signals generated during the initial alarm-on period, a reminder alarm signal might be turned on periodically during a follow-on periodic reminder time period. This periodic reminder time is typically much longer than the initial alarm-on period. The periodic reminder time period would typically be 3 to 5 hours because after 3 to 5 hours the patient's advantage in being alerted to seek medical attention for a severe cardiac event like an AMI is mostly lost. It is also envisioned that the periodic reminder time period could also be programmable through the programmer 68 to be as short as 5 minutes or even continue indefinitely until the patient acknowledges the alarm signal with the button 59 or the programmer 68 is used to interact with the cardiosaver 5.

Following the initial alarm on-period there would be an alarm off-period followed by a reminder alarm on-period followed by an alarm off-period followed by another reminder alarm on-period and so on periodically repeating until the end of the periodic reminder time period.

The alarm off-period time interval between the periodic reminders might also increase over the reminder alarm on-period. For example, the initial alarm-on period might be 5 minutes and for the first hour following the initial alarm-on period, a reminder signal might be activated for 30 seconds every 5 minutes. For the second hour the reminder alarm signal might be activated for 20 seconds every 10 minutes and for the remaining hours of the periodic reminder on-period the reminder alarm signal might be activated for 30 seconds every 15 minutes.

The patient might press the panic button 52 in the event that the patient feels that he is experiencing a cardiac event. The panic button 52 will initiate the transmission from the cardiosaver 5 to the external alarm system 60 via the wireless signal 53 of both recent and baseline electrogram segments. The external alarm system 60 will then retransmit these data via the link 65 to emergency medical services 67 where a medical practitioner will view the electrogram data. The remote medical practitioner could then analyze the electrogram data and call the patient back to offer advice as to whether this is an emergency situation or the situation could be routinely handled by the patient's personal physician at some later time.

It is envisioned that there may be preset limits within the external alarm system 60 that prevent the patient operated initiator 55 and/or panic button from being used more than a certain number of times a day to prevent the patient from running down the batteries in the cardiosaver 5 and external alarm system 60 as wireless transmission takes a relatively large amount of power as compared with other functional operation of these devices.

Figure 2:
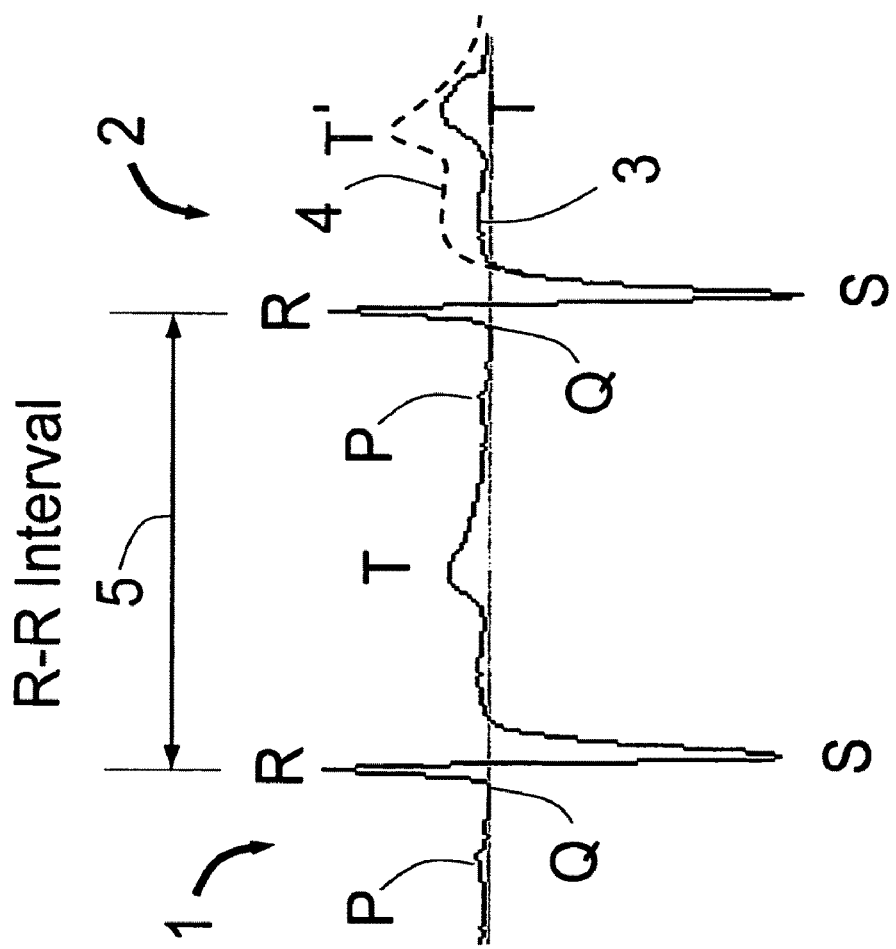
FIG. 2 illustrates a normal electrogram pattern and also shows a superimposed elevated ST segment that would be indicative of an acute myocardial infarction.
Figure 3:
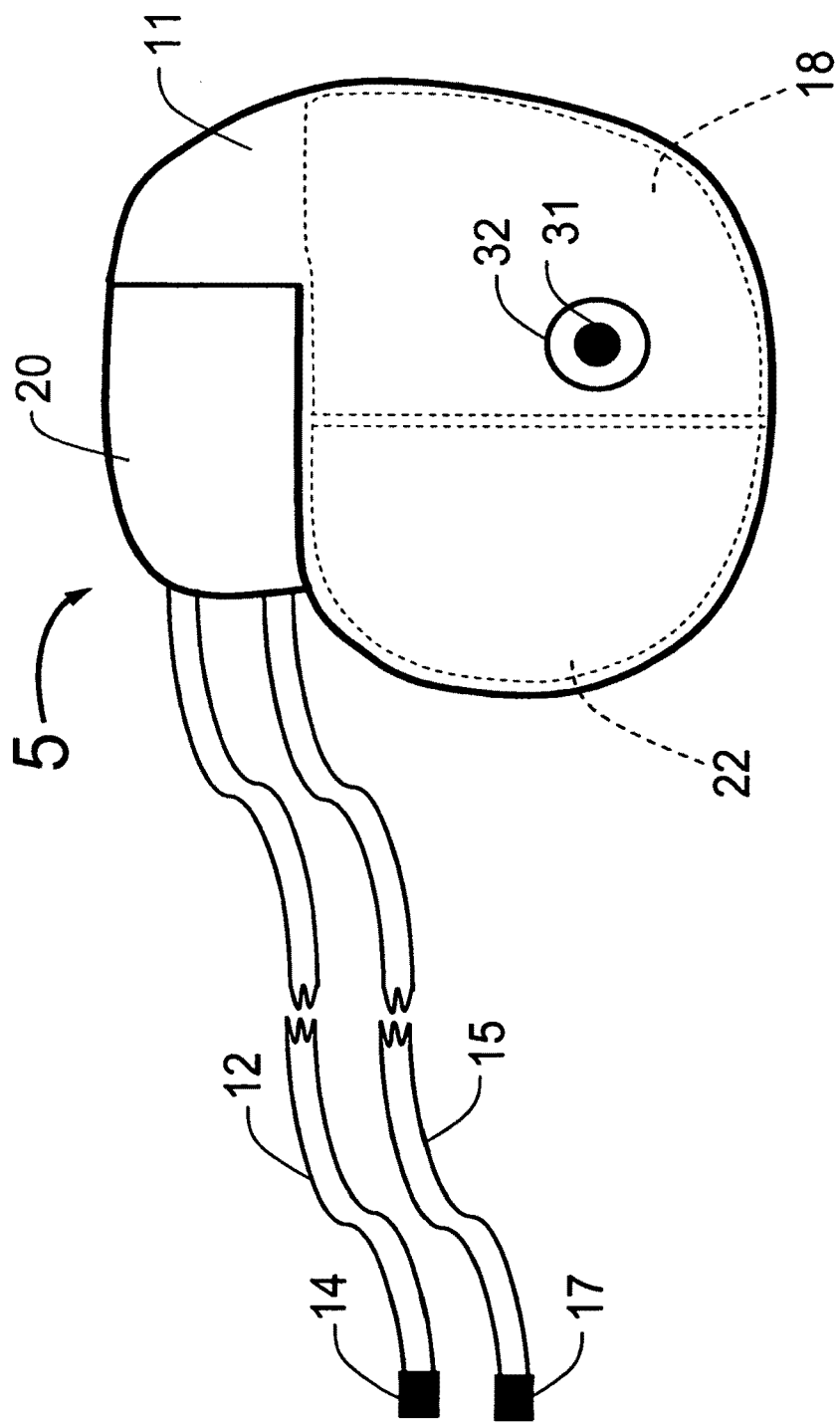
FIG. 3 is a plan view of the cardiosaver showing the cardiosaver electronics module and two electrical leads each having one electrode.

FIG. 2 illustrates a typical electrogram signal having beats 1 and 2 from some pair of implanted electrodes such as the electrode 14 and the case 11 of FIG. 3 overlaid with an electrogram having an elevated ST segment 4 (dashed line). The various portions of the electrogram are shown as the P, Q, R, S, and T waves. These are all shown as portions of a solid line in FIG. 2. The normal ST segment 3 of beat 2 is also shown in FIG. 2. The R-R interval 5 for beat 2 is shown as the time between the R waves of beat 2 and the beat before it (beat 1).

When an acute myocardial infarction occurs, there is typically an elevation (or depression) of the ST segment 4 as shown by the dashed line in FIG. 2. It is this shift of the ST segment 4 as compared to the baseline ST segment 3 that is a clear indicator that an acute myocardial infarction has occurred in a significant portion of the patient's myocardium.

Although an elevated ST segment 4 can be a good indicator of an acute myocardial infarction, other indicators such as a sudden change of heart rate or heart wall motion, intra-coronary blood pressure or a sudden decrease in blood $pO_2$ could also be used as independent sensing means or those signals could be used in addition to the voltage shift of the ST segment 4.

It is important to note that the electrogram from implanted electrodes may provide a faster detection of an ST segment shift as compared to an electrocardiogram signal obtained from skin surface electrodes. Thus the electrogram from implanted electrodes as described herein is the preferred embodiment of the present invention.

It is also well known that the T wave can shift very quickly when a heart attack occurs. It is envisioned that the present invention might detect this T wave shift as compared to a time of 1 to 5 minutes in the past.

It is anticipated that when a patient who has a stenosis in a coronary artery is performing a comparatively strenuous exercise his heart rate increases and he can develop exercise induced ischemia that will also result in a shift of the ST segment of his electrogram. This is particularly true for patients who have undergone balloon angioplasty with or without stent implantation. Such patients will be informed by their own physician that, if their cardiosaver 5 of FIG. 1 activates an alarm during exercise, that it may be indicative of the progression of an arterial stenosis in one of the heart's arteries. Such a patient would be advised to stop all exertion immediately and if the alarm signal goes away as his heart rate slows, the patient should see his doctor as soon as convenient. If the alarm signal does not go away as the patient's heart rate slows down into the normal range then the cardiosaver will change the alarm signal to indicate that the patient should immediately seek medical care. As previously described, the cardiosaver 5 could emit a different signal if there is a heart attack as compared to the signal that would be produced if there were ischemia resulting from exercise.

It is also envisioned that heart rate and the rate of change of heart rate experienced during an ST segment voltage shift can be used to indicate which alarm should be produced by the cardiosaver 5. Specifically, an ST segment shift at a near normal heart rate would indicate an acute myocardial infarction. An ST segment shift when there is an elevated heart rate (e.g., greater than 100 bpm) would generally be indicative of a progressing stenosis in a coronary artery. In any case, if a sufficient ST segment shift occurs that results in an alarm from the cardiosaver 5, the patient should promptly seek medical care to determine the cause of the alarm.

It should be understood that, depending on a patient's medical condition, a vigorous exercise might be as energetic as running a long distance or merely going up a flight of stairs. After the cardiosaver 5 is implanted in a patient who has undergone a stent implant, he should have a stress test to determine his level of ST segment shift that is associated with the highest level of exercise that he can attain. The patient's heart rate should then be noted and the cardiosaver thresholds for detection, described with FIGS. 5 through 10, should be programmed so as to not alarm at ST segment shifts observed during exercise. Then if at a later time the patient experiences an increased shift of his ST segment at that pre-determined heart rate or within a heart rate range, then an alarm indicating ischemia can be programmed to occur. The occurrence of such an alarm can indicate that there is a progression in the narrowing of some coronary artery that may require angiography to determine if angioplasty, possibly including stent implantation, is required.

The alarm signal associated with an excessive ST shift caused by an acute myocardial infarction can be quite different from the "SEE DOCTOR" alarm means associated with progressing ischemia during exercise. For example, the SEE DOCTOR alert signal might be an audio signal that occurs once every 5 to 10 seconds. A different alarm signal, for example an audio signal that is three buzzes every 3 to 5 seconds, may be used to indicate a major cardiac event such as an acute myocardial infarction. Similar alarm signal timing would typically be used for both internal alarm signals generated by the alarm sub-system 48 of FIG. 4 and external alarm signals generated by the external alarm system 60.

In any case, a patient can be taught to recognize which signal occurs for these different circumstances so that he can take immediate response if an acute myocardial infarction is indicated but can take a non-emergency response if progression of the narrowing of a stenosis or some other less critical condition is indicated. It should be understood that other distinctly different audio alarm patterns could be used for different arrhythmias such as atrial fibrillation, atrial flutter, PVC's, PAC's, etc. A capability of the physician's programmer 68 of FIG. 1 would be to program different alarm signal patterns, enable or disable detection and/or generation of associated alarm signals in the cardiosaver for any one or more of these various cardiac events. Also, the intensity of the audio alarm, vibration or electrical tickle alarm could be adjusted to suit the needs of different patients. In order to familiarize the patient with the different alarm signals, the programmer 68 of the present invention would have the capability to turn each of the different alarm signals on and off.

FIG. 3 is a plan view of the cardiosaver 5 having a case 11 and a plastic header 20. The case 11 contains the primary battery 22 and the electronics module 18. This type of package is well known for pacemakers, implantable defibrillators and implantable tissue stimulators. Electrical conductors placed through the plastic header 20 connect the electronics module 18 to the electrical leads 12 and 15, which have respectively electrodes 14 and 17. The on-case electrodes 8 and 9 of FIG. 1 are not shown in FIG. 3. It should also be understood that the cardiosaver 5 can function with only two electrodes, one of which could be the case 11. All the different configurations for electrodes shown in FIGS. 1 and 3, such as the electrodes 8, 9, 13, 14, 16 or the metal case 11 are shown only to indicate that there are a variety of possible electrode arrangements that can be used with the cardiosaver 5.

On the metal case 11, a conducting disc 31 mounted onto an insulating disc 32 can be used to provide a subcutaneous electrical tickle to warn the patient that an acute myocardial infarction is occurring or to act as an independent electrode.

Figure 4:
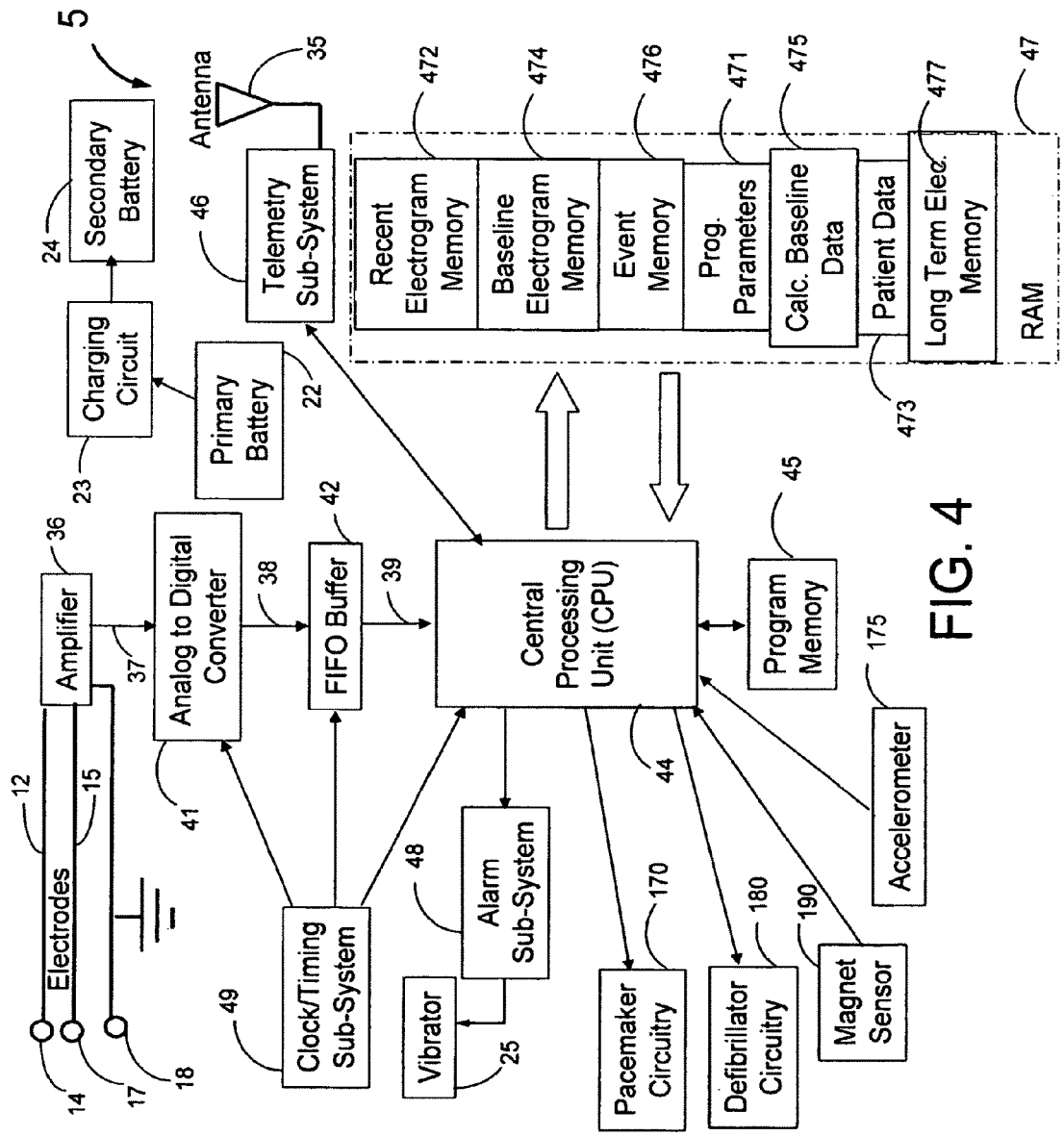
FIG. 4 is a block diagram of the cardiosaver.

FIG. 4 is a block diagram of the cardiosaver 5 with primary battery 22 and a secondary battery 24. The secondary battery 24 is typically a rechargeable battery of smaller capacity but higher current or voltage output than the primary battery 22 and is used for short term high output components of the cardiosaver 5 like the RF chipset in the telemetry sub-system 46 or the vibrator 25 attached to the alarm sub-system 48. An important feature of the present invention cardiosaver is the dual battery configuration where the primary battery 22 will charge the secondary battery 24 through the charging circuit 23. The primary battery 22 is typically a larger capacity battery than the secondary battery 24. The primary battery also typically has a lower self discharge rate as a percentage of its capacity than the secondary battery 24. It is also envisioned that the secondary battery could be charged from an external induction coil by the patient or by the doctor during a periodic check-up.

The electrodes 14 and 17 connect with wires 12 and 15 respectively to the amplifier 36 that is also connected to the case 11 acting as an indifferent electrode. As two or more electrodes 12 and 15 are shown here, the amplifier 36 would be a multi-channel amplifier. The amplified electrogram signals 37 from the amplifier 36 are then converted to digital signals 38 by the analog-to-digital converter 41. The digital electrogram signals 38 are buffered in the First-In-First-Out (FIFO) memory 42. Processor means shown in FIG. 4 as the central processing unit (CPU) 44 coupled to memory means shown in FIG. 4 as the Random Access Memory (RAM) 47 can process the digital electrogram data 38 stored the FIFO 42 according to the programming instructions stored in the program memory 45. This programming (i.e. software) enables the cardiosaver 5 to detect the occurrence of a cardiac event such as an acute myocardial infarction.

A clock/timing sub-system 49 provides the means for timing specific activities of the cardiosaver 5 including the absolute or relative time stamping of detected cardiac events. The clock/timing sub-system 49 can also facilitate power savings by causing components of the cardiosaver 5 to go into a low power standby mode in between times for electrogram signal collection and processing. Such cycled power savings techniques are often used in implantable pacemakers and defibrillators. In an alternate embodiment, the clock/timing subsystem can be provided by a program subroutine run by the central processing unit 44.

In an advanced embodiment of the present invention, the clock/timing circuitry 49 would count for a first period (e.g. 20 seconds) then it would enable the analog-to-digital converter 41 and FIFO 42 to begin storing data, after a second period (e.g. 10 seconds) the timing circuitry 49 would wake up the CPU 44 from its low power standby mode. The CPU 44 would then process the 10 seconds of data in a very short time (typically less than a second) and go back to low power mode. This would allow an on off duty cycle of the CPU 44 which often draws the most power of less than 2 seconds per minute while actually collecting electrogram data for 20 seconds per minute.

In a preferred embodiment of the present invention the RAM 47 includes specific memory locations for 4 sets of electrogram segment storage. These are the recent electrogram storage 472 that would store the last 2 to 10 minutes of recently recorded electrogram segments so that the electrogram data leading in the period just before the onset of a cardiac event can be reviewed at a later time by the patient's physician using the physician's programmer 68 of FIG. 1. For example, the recent electrogram storage 472 might contain eight 10 second long electrogram segments that were captured every 30 seconds over the last 4 minutes.

The baseline electrogram memory 474 would provide storage for baseline electrogram segments collected at preset times over one or more days. For example, the baseline electrogram memory 474 might contain 24 baseline electrogram segments of 10 seconds duration, one from each hour for the last day, and information abstracted from these baselines.

A long term electrogram memory 477 would provide storage for electrograms collected over a relatively long period of time. In the preferred embodiment, every ninth electrogram segment that is acquired is stored in a circular buffer, so that the oldest electrogram segments are overwritten by the newest one.

The event memory 476 occupies the largest part of the RAM 47. The event memory 476 is not overwritten on a regular schedule as are the recent electrogram memory 472 and baseline electrogram memory 474 but is typically maintained until read out by the patient's physician with the programmer 68 of FIG. 1. At the time a cardiac event like excessive ST shift indicating an acute myocardial infarction is detected by the CPU 44, all (or part) of the entire contents of the baseline and recent electrogram memories 472 and 474 would typically be copied into the event memory 476 so as to save the pre-event data for later physician review.

In the absence of events, the event memory 476 could be used temporarily to extend the recent electrogram memory 472 so that more data (e.g. every 10 minutes for the last 12 hours) could be held by the cardiosaver 5 of FIG. 1 to be examined by a medical practitioner at the time a patient visits. This would typically be overwritten with pre- and post-event electrogram segments following a detected event.

An example of use of the event memory 476 would have a SEE DOCTOR alert saving the last segment that triggered the alarm and the baseline used by the detection algorithm in detecting the abnormality. An EMERGENCY ALARM would save the sequential segments that triggered the alarm, a selection of other pre-event electrogram segments, or a selection of the 24 baseline electrogram segments and post-event electrogram segments. For example, the pre-event memory would have baselines from −24 hrs, −18, −12, −6, −5, −4, −3, −2 and −1 hours, recent electrogram segments (other than the triggering segments) from −5 minutes, −10, −20, −35, and −50 minutes, and post-event electrogram segments for every 5 minutes for the 2 hours following the event and for every 15 minutes after 2 hours post-event. These settings could be pre-set or programmable.

The RAM 47 also contains memory sections for programmable parameters 471 and calculated baseline data 475. The programmable parameters 471 include the upper and lower limits for the normal and elevated heart rate ranges, and physician programmed parameters related to the cardiac event detection processes stored in the program memory 45. The calculated baseline data 475 contain detection parameters extracted from the baseline electrogram segments stored in the baseline electrogram memory 474. Calculated baseline data 475 and programmable parameters 471 would typically be saved to the event memory 476 following the detection of a cardiac event. The RAM 47 also includes patient data 473 that may include the patient's name, address, telephone number, medical history, insurance information, doctor's name, and specific prescriptions for different medications to be administered by medical practitioners in the event of different cardiac events.

It is envisioned that the cardiosaver 5 could also contain pacemaker circuitry 170 and/or defibrillator circuitry 180 similar to the cardiosaver systems described by Fischell in U.S. Pat. No. 6,240,049.

The alarm sub-system 48 contains the circuitry and transducers to produce the internal alarm signals for the cardiosaver 5. The internal alarm signal can be a mechanical vibration, a sound or a subcutaneous electrical tickle or shock.

The telemetry sub-system 46 with antenna 35 provides the cardiosaver 5 the means for two-way wireless communication to and from the external equipment 7 of FIG. 1. Existing radiofrequency transceiver chip sets such as the Ash transceiver hybrids produced by RF Microdevices, Inc. can readily provide such two-way wireless communication over a range of up to 10 meters from the patient. It is also envisioned that short range telemetry such as that typically used in pacemakers and defibrillators could also be applied to the cardiosaver 5. It is also envisioned that standard wireless protocols such as Bluetooth and 802.11a or 802.11b might be used to allow communication with a wider group of peripheral devices.

A magnet sensor 190 may be incorporated into the cardiosaver 5. An important use of the magnet sensor 190 is to turn on the cardiosaver 5 on just before programming and implantation. This would reduce wasted battery life in the period between the times that the cardiosaver 5 is packaged at the factory until the day it is implanted.

The cardiosaver 5 might also include an accelerometer 175. The accelerometer 174 together with the processor 44 is designed to monitor the level of patient activity and identify when the patient is active. The activity measurements are sent to the processor 44. In this embodiment the processor 44 can compare the data from the accelerometer 175 to a preset threshold to discriminate between elevated heart rate resulting from patient activity as compared to other causes.

Figure 5:
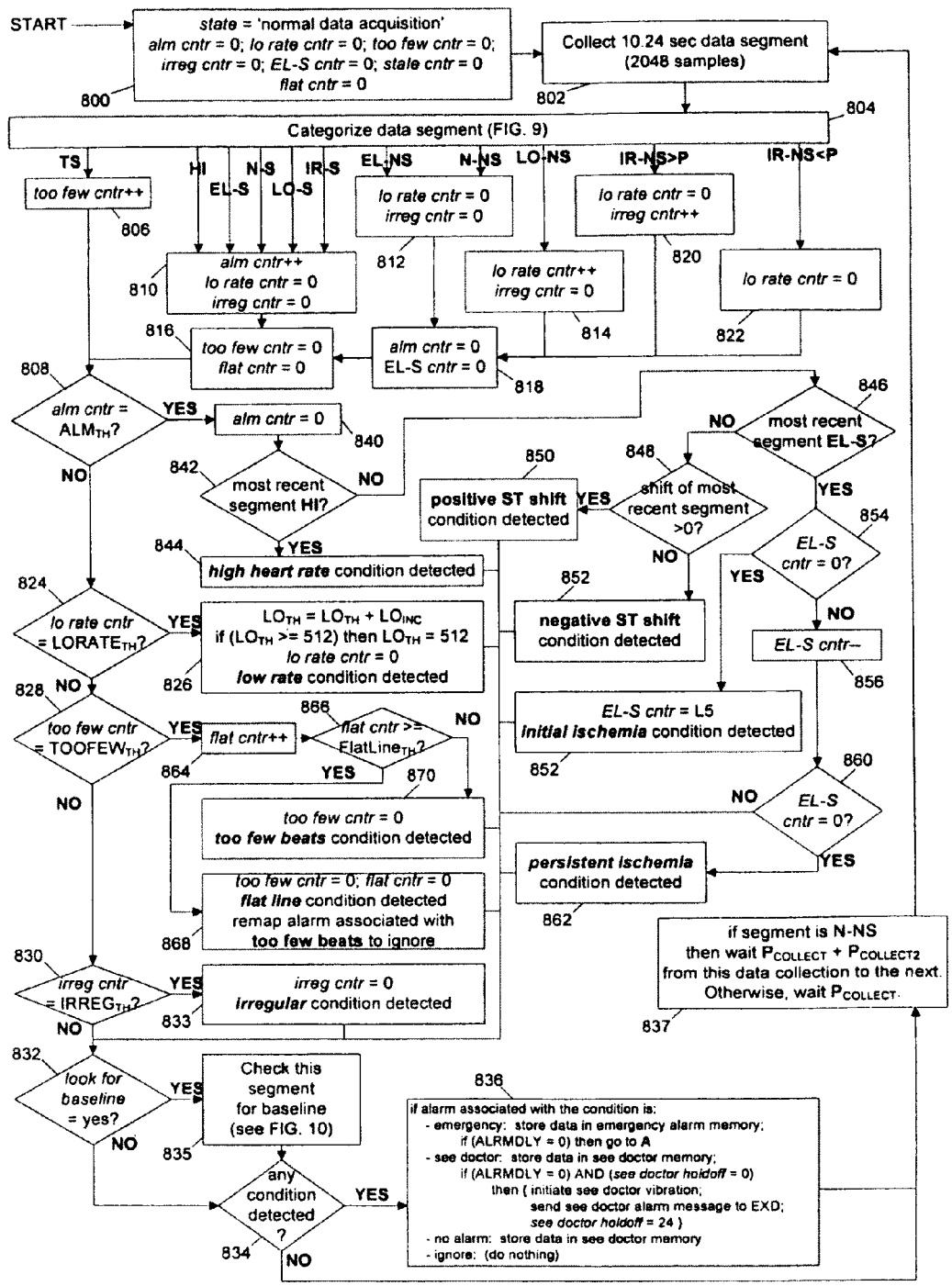
FIG. 5 is a block diagram of the cardiosaver event detection program.

FIG. 5 illustrates in the form of a block diagram the operation of the heart signal processing program 450 for cardiac event detection by the cardiosaver 5 of FIGS. 1-4. The heart signal processing program 450 is an example of one of many such detection programs whose instructions could reside in the program memory 45 for use by the CPU 44 of the cardiosaver 5 as shown in FIG. 4. The program shown in FIG. 5 is preferably run continuously. There is another routine, shown in FIG. 7, that preferably is run once per hour. The hourly routine stores various histogram data (see U.S. patent application Ser. No. 10/950,401, filed Sep. 28, 2004, entitled "Implantable system for monitoring the condition of the heart") and also operates in conjunction with the program shown in FIG. 5 to enable collection of baselines for each hourly period.

Turning to the program shown in FIG. 5, in block 800, various flags and counters, whose roles will be described further below, are initialized. In block 802, a data segment is captured into the FIFO buffer 42 of FIG. 4 and then transferred to the recent electrogram memory 472 of FIG. 4. The data segment is Y seconds long, where Y is preferably 10.24 sec., which corresponds to 2048 samples at a sampling rate of 200 Hz. Next, in block 804, which is described in detail with reference to FIG. 9, the acquired data segment is categorized as one of the following:

| Abbreviation | Description |
| --- | --- |
| HI | High Heart Rate |
| EL-S | Elevated Heart Rate with an ST Shift |
| EL-NS | Elevated Heart Rate with no ST Shift |
| N-S | Normal Heart Rate with an ST Shift |
| N-NS | Normal Heart Rate with no ST Shift |
| LO-S | Low Heart Rate with an ST Shift |
| LO-NS | Low Heart Rate with no ST Shift |
| IR-S | Irregular Heart Rate with an ST Shift |
| IR-NS>P | Irregular Heart Rate with no ST Shift with lots of short beats |
| IR-NS<P | Irregular Heart Rate with no ST Shift with few short beats |
| TS | Too Short (not enough "good" beats) |

If the segment has been categorized as "too short" (or TS), meaning that it does not have a sufficient number of acceptable beats, the program 450 moves to block 806, where the too few counter is incremented by 1. The program 450 then moves to block 808. As will be described further below, the too few counter tracks the number of consecutive (processed/categorized) segments that are "too short" for the purpose of generating an alarm in the case where there are so many consecutive TS segments that a medical or device problem is possible.

Returning to block 804, if the segment exhibits an ST shift or a high heart rate (HI, EL-S, N-S, LO-S or IR-S), an alarm counter (alm cntr) is incremented in block 810. Also in block 810, low heart rate (lo rate cntr) and irregular (irreg cntr) counters are set to 0. These counters track the number of consecutive segments characterized by low heart rates and irregular rhythms, respectively. (Even though one of the categories that results in a movement to block 810, LO-S, is associated with a low heart rate, the low rate counter is nonetheless set to 0 because that counter tracks the number of low heart rate segments that are not ST shifted.)

From block 810, the program 450 moves to block 816, where the too few cntr and flat cntr counters are set to 0 because the current segment is not TS ("too short"). These counters work in tandem to determine the number of consecutively acquired "too short" segments. Thus, any segment that is acquired that is not "too short" will result in setting these counters back to 0.

Again returning to block 804, if the segment has been categorized as non-ST shifted and either elevated or normal heart rate (EL-NS or N-NS), the program 450 moves to block 812 and sets the rate cntr and irreg cntr to 0. From block 812, the program 450 moves to block 818, where the alm cntr is set to 0. The alm cntr variable tracks the number of consecutive segments that exhibit an ST shift or a high heart rate. Thus, this counter is reset to 0 when any segment is acquired that is not of that type. Similarly, the EL-S counter (EL-S cntr), which tracks the number of consecutive segments characterized by an elevated heart rate and ST shift, is reset to 0.

Again returning to block 804, if the segment is categorized as low heart rate with no ST shift (LO-NS), control is transferred to block 814, where the lo rate cntr is incremented and the irregular rhythm counter (irreg cntr) is reset to 0. From block 514, control is transferred to block 818.

Again returning to block 804, if the segment is characterized as having an irregular rhythm with too many short beats with no ST shift (IR-NS>P), control is transferred to block 820, where the lo rate cntr is reset to 0, and the irreg cntr is incremented. From block 820, control is transferred to block 818.

Again returning to block 804, if the segment is characterized as having an irregular rhythm with few short beats and not having an ST shift (IR-NS<P), control is transferred to block 822, where the lo rate cntr is reset to 0. From block 822, control is transferred to block 818.

All of the characterization and counter setting steps mentioned above eventually proceed to block 808, which checks whether the alarm counter (alm cntr) has reached the threshold ($ALM_{TH}$) needed for detection. $ALM_{TH}$ is preferably set to 3, which means that 3 consecutively processed/categorized segments must have been characterized as exhibiting an ST shift or a high heart rate before an event to said to be detected. Thus, an ST shift or a high heart rate condition must be somewhat persistent to trigger an event detection, which helps to avoid false positive detections.

$ALM_{TH}$ is a programmable parameter that could be increased to avoid false positive detections. With current average times from onset of a heart attack to arrival at a treatment center of 3 hours, a few minutes delay for a device that should enable the patient to easily reach a treatment center within 30 minutes is valuable if it improves the reliability of detection.

If the alm cntr has reached $ALM_{TH}$, the type of alarm to issue is determined, as will be further described below.

If alm cntr is less than $ALM_{TH}$, control passes to block 824, which checks whether the low rate counter (lo rate cntr) has reached the threshold ($LORATE_{TH}$) for detecting a low heart rate condition. If lo rate cntr has reached the threshold (LORATE$_{TH}$), then control passes to block 826, which adjusts the threshold (LO$_{TH}$) for detecting low heart rates (as will be further described with reference to FIG. 8) so that LO$_{TH}$=LO$_{TH}$+LO$_{INC}$ or 512, whichever is smaller. (Temporal quantities such as LO$_{TH}$ are expressed as a number of samples at a sampling rate of 200 Hz.)

Thus, for future segments, a lower heart rate is required to characterize a segment as a low heart rate segment. Both the initial LO$_{TH}$ (i.e. the LO$_{TH}$ that applies before the first segment is acquired after implantation) and LO$_{INC}$ are programmable. An initial LO$_{TH}$ value corresponding to approximately 50 beats/min (200*60/50 at a 200 Hz sampling rate) is preferred. A LO$_{INC}$ corresponding to approximately 5 beats/min (at 50 beats/min) is preferred.

The low rate counter (lo rate cntr) is reset and a low rate condition is detected. Control then passes to the baseline checking routine (block 832), which will be further described below.

Returning to block 824, if the low rate counter (lo rate cntr) is not less than LORATE$_{TH}$, control passes to block 828, which checks whether the "too few" beats counter (too few cntr) has reached the threshold (TOOFEW$_{TH}$) for detecting too few good beats. If so, the "too few" beat routine is invoked, starting at block 864, as will be further described below. If not, control passes to block 830, which checks whether the "irregular rhythm" segment counter (irreg cntr) has reached the threshold (IRREG$_{TH}$) for triggering an event for irregular beats. If so, control passes to block 833, which resets irreg cntr to 0 and sets a flag indicating that an irregular condition has been detected.

Control then passes to the baseline checking routine beginning at block 832. Control also passes to block 832 directly from block 830. Block 832 checks whether a baseline is desired by examining a look for baseline flag. Whether a baseline is desired, in turn, depends upon a number of factors. First, whether a baseline is desired depends on whether baselining is enabled, which is externally programmable. If baselining is not enabled, the look for baseline flag is set to 0 and does not change (unless and until baselining is reenabled.) If baselining is enabled, then the heart signal processing program 450 will try to find a baseline for each hourly period, starting at the beginning of the hourly period. If the heart signal processing program 450 has already found a baseline for the current hourly period, or if it has tried and failed to find a baseline for the current hourly period, then the look for baseline flag will have been set to 0 (as will be further described with reference to FIG. 12) and control will be passed to block 834. Otherwise, the present segment will be checked to determine whether it is a proper baseline segment according to the routine indicated by block 835 that is described further in FIG. 12. Control will then be passed to block 834.

Block 834 checks whether any condition has been detected with this segment. If not, control passes to block 837, which waits a certain amount of time before the next data segment is acquired in block 802. Specifically, if the current segment is normal and not ST shifted, then the program 450 waits for a relatively longer amount of time (P$_{COLLECT}$+P$_{COLLECT2}$) before acquiring the next segment, based on the assumption that when the patient is normal and has a normal heart rate, segments need not be taken as frequently to determine if the patient has or may develop a problem. In any other case, the program 450 waits for a relatively shorter amount of time (P$_{COLLECT}$) before acquiring the next segment. Preferred times for P$_{COLLECT}$ and P$_{COLLECT2}$ are 30 seconds and 60 seconds, respectively.

In an alternate embodiment, some other criteria apart from (or in addition to) time may determine the baseline acquisition time. Whether a baseline is desired depends on whether a baseline for the current period has already been found, or whether too many attempts have been made to find a baseline for the current period, as will be further described with reference to FIG. 12.

Returning to block 834, if a condition has been detected, control passes to block 836. In block 836, the routine checks what type of action should be taken when a particular condition has been detected. There are four possible actions which may generally be mapped by a medical practitioner to a particular condition: (1) generate an emergency alarm (and store data); (2) generate a "See Doctor" alert (and store data); (3) store data only; and (4) do nothing.

In block 836, if the condition is mapped to an emergency alarm, then the contents of the recent electrogram data storage 472, preferably 8 electrogram segments, is stored in the emergency alarm memory that is part of the event memory 476. This allows the patient's physician to review the electrogram segments collected during a period of time that occurred before the alarm, unless the data is overwritten by subsequent emergency alarm data. Also, a subset of the long term electrogram data in the long term electrogram memory 477 and the baseline electrogram memory 474 are written into the emergency alarm memory.

Data corresponding to the first emergency alarm is stored in the "emergency alarm memory-1" area of memory. If it is not the first emergency alarm, the data is stored in the "emergency alarm memory-2" area of memory. This approach means that if more than 2 emergency alarms are detected before a 'release memory' command is received, then the segments for the first (oldest) and the most recent (newest) are kept.

Because there is a possibility that segments from one or more emergency alarms may be lost with this approach, a counter of the number of emergency alarms since the last 'release memory' command was received, not shown in the figures, TOTEMER, is maintained.

After data is written to memory, if a counter ALARMDLY is 0, an emergency alarm is generated according to the alarm subroutine 490, which is described with reference to. FIG. 8. ALARMDLY, which is programmable, controls the duration that the device will not issue any alarms, regardless of whether it detects a condition. This counter is decremented every hour, as will be described with reference to FIG. 7.

In block 836, if the condition is mapped to "See Doctor Alert", a subset (preferably the most recent 3 segments) of the recent electrogram data 472 is stored in the appropriate place in "see doctor" memory. Also, the baseline electrogram memory 474 is written into the "see doctor" memory. There are 6 areas of "see doctor" memory that are used in a circular buffer. That is, if 7 see doctor alerts occur before a 'release memory' command is received, segments for the 2nd through the 7th are kept. If both ALARMDLY is 0 and see doctor holdoff are 0, then a "See Doctor Alert" vibration is generated by the alarm subroutine 490 described with reference to FIG. 8. The see doctor holdoff controls the amount of time after generation of a first "See Doctor Alert" that the next "See Doctor Alert" may be generated (if another "See Doctor Alert" type of condition is detected). This counter is decremented every hour, as will be described with reference to FIG. 7. It is reset to a default value of 24 (hours) after a "See Doctor Alert" is generated, which means that any "See Doctor Alert" type conditions that occur in the subsequent 24 hours will not result in the generation of a "See Doctor Alert."

If the condition is not mapped to an alarm but to only storing data, then the data is stored in the circular buffer "See Doctor" memory. However, no vibration is initiated. Finally, if the condition is mapped to nothing at all, it is simply ignored.

Returning to block 808, if the alarm counter=ALM$_{TH}$, a routine is invoked to classify the type of condition that caused the alarm counter to reach threshold. In block 840, the alarm counter (alm cntr) is reset to 0 and control passes to block 842, which checks whether the current electrogram segment is characterized by a high heart rate. If so, a high heart rate flag is set in block 844 and control then passes to block 832. If the segment is not associated with a high heart rate, block 842 transfers control to block 846, which checks whether the current electrogram segment is characterized as an elevated heart rate with an ST shift (EL-S). If not, control passes to block 848, which checks the polarity of the ST shift (i.e. greater than or less than 0), with corresponding positive and negative ST shift flags set in blocks 850 and 852, respectively. From either of these blocks, control is transferred to block 832.

Returning to block 846, if the most recent segment is characterized as an elevated heart rate with an ST shift (EL-S), control basses to block 854. An elevated heart rate with an ST shift (EL-S) may be a result of exercise. To help avoid false positives, there are two conditions for ST shift with elevated heart rates: "initial ischemia" and "persistent ischemia". "Initial ischemia" is detected much like other conditions described above: a set of characteristics for a number of consecutive segments. "Persistent ischemia" is detected by detecting "initial ischemia" a number of consecutive times. For a particular example, in a preferred embodiment, 3 consecutive EL-S segments will generally be required to detect an "initial ischemia", while 21 consecutive EL-S segments will generally be required to detect a "persistent ischemia".

The 21 segment criterion is implemented by an EL-S counter (EL-S cntr), which is set to 7 after the "initial ischemia" is detected (first 3 EL-S segments), and decrementing this counter (in block 856) each time another consecutive "initial ischemia" is detected. (It is theoretically possible that 7 consecutive groups of 3 segments could give rise to "persistent ischemia" even though not all segments within each group is an EL-S. For example, if the pattern of N-S, N-S, EL-S were to repeat seven times, "persistent ischemia" would be detected. This would seem to be quite unlikely from a physiological standpoint.)

The above mentioned EL-S scheme is implemented by checking the value of the EL-S counter in block 854. If the counter is 0, then the current segment indicates the detection of "initial ischemia". If so, control is passed to block 858, where the EL-S counter is set to (preferably) 7. If the EL-S counter is not equal to 0, which indicates that a run of EL-S segments has been detected, the EL-S counter is decremented in block 856. Control then passes to block 860, which checks whether the EL-S counter is 0, which would signify a run of (preferably) 7 consecutive groups of 3 EL-S segments ("initial ischemia" detections). If so, then a "persistent ischemia" flag is set in block 862. Otherwise, no alarm for this segment is signified, and control passes to block 832.

Returning to block 828, if the too few cntr has reached the threshold for detecting a problem pertaining to a lack of detected heart beats, control passes from block 828 to block 864, where the flat line counter (flat cntr) is incremented. As previously mentioned, this counter, along with too few cntr, keeps track of the number of consecutive segments with too few beats. Specifically, the number of consecutive segments with too few beats is equal to TOOFEW$_{TH}$*flat cntr+too few cntr. TOOFEW$_{TH}$ is preferably set to 4.

In block 866, the flat counter is compared to a threshold (FlatLine$_{TH}$), which is preferably equal to 3. If so, there has been a sufficient number of consecutive segments with too few beats to signify a flat line condition, and control passes to block, where flat cntr and too few cntr are reset, and a "flat line" flag is set to indicate a flat line condition. If flat cntr is less than FlatLine$_{TH}$, control passes to block 870, which resets too few cntr and sets a flag that signifies a "too few beats" condition.

Figure 6:
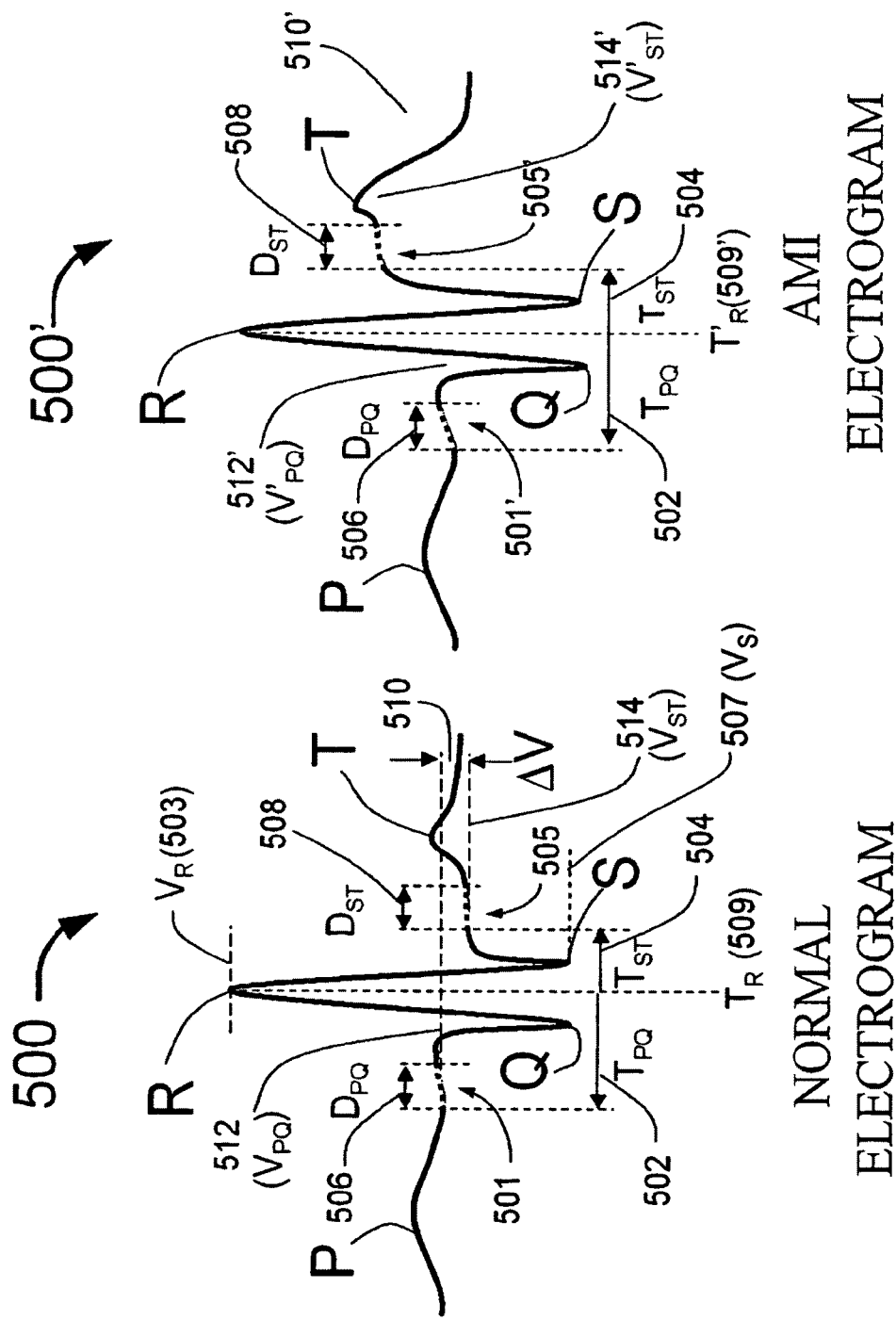
FIG. 6 illustrates the extracted electrogram segment features used to calculate ST shift.

FIG. 6 illustrates the features of a single normal beat 500 of an electrogram segment and a single beat 500' of an AMI electrogram segment that has a significant ST segment shift as compared with the normal beat 500. Such ST segment shifting occurs within minutes following the occlusion of a coronary artery during an AMI. The beats 500 and 500' show typical heart beat wave elements labeled P, Q, R, S, and T. The definition of a beat such as the beat 500 is a sub-segment of an electrogram segment containing exactly one R wave and including the P and Q elements before the R wave and the S and T elements following the R wave.

For the purposes of detection algorithms, different sub-segments, elements and calculated values related to the beats 500 and 500' are hereby specified. The peak of the R wave of the beat 500 occurs at the time T$_R$ (509). The PQ segment 501 and ST segment 505 are sub-segments of the normal beat 500 and are located in time with respect to the time T$_R$ (509) as follows:
  a. The PQ segment 501 has a time duration D$_{PQ}$ (506) and starts T$_{PQ}$ (502) milliseconds before the time T$_R$ (509).
  b. The ST segment 505 has a time duration D$_{ST}$ (508) and starts T$_{ST}$ (502) milliseconds after the time T$_R$ (509).

The PQ segment 501' and ST segment 505' are sub-segments of the beat 500' and are located in time with respect to the time T'$_R$ (509') as follows:
  c. The PQ segment 501' has a time duration D$_{PQ}$ (506) and starts T$_{PQ}$ (502) milliseconds before the time T'$_R$ (509').
  d. The ST segment 505' has a time duration D$_{ST}$ (508) and starts T$_{ST}$ (502) milliseconds after the time T'$_R$ (509').

The ST segments 505 and 505' and the PQ segments 501 and 501' are examples of sub-segments of the electrical signals from a patient's heart. The R wave and T wave are also sub-segments. The dashed lines V$_{PQ}$ (512) and V$_{ST}$ (514) illustrate the average voltage amplitudes of the PQ and ST segments 501 and 505 respectively for the normal beat 500. Similarly the dashed lines V'$_{PQ}$ (512') and V'$_{ST}$ (514') illustrate the average amplitudes of the PQ and ST segments 501' and 505' respectively for the beat 500'. The "ST deviation" ΔV (510) of the normal beat 500 and the ST deviation ΔV$_{AMI}$ (510') of the AMI electrogram beat 500' are defined as:

$$\Delta V(510) = V_{ST}(514) - V_{PQ}(512)$$

$$\Delta V_{AMI}(510') = V'_{ST}(514') - V'_{PQ}(512')$$

Note that the both beats 500 and 500' are analyzed using the same time offsets T$_{PQ}$ and T$_{ST}$ from the peak of the R wave and the same durations D$_{PQ}$ and D$_{ST}$. In this example, the beats 500 and 500' are of the same time duration (i.e. the same heart rate). The parameters T$_{PQ}$, T$_{ST}$, D$_{PQ}$ and D$_{ST}$ would typically be set with the programmer 68 of FIG. 1 by the patient's doctor at the time the cardiosaver 5 is implanted so as to best match the morphology of the patient's electrogram signal and normal heart rate. V$_{PQ}$ (512), V$_{ST}$ (514), V$_R$ (503) and ΔV (510) are examples of per-beat heart signal parameters for the beat 500.

Figure 7:
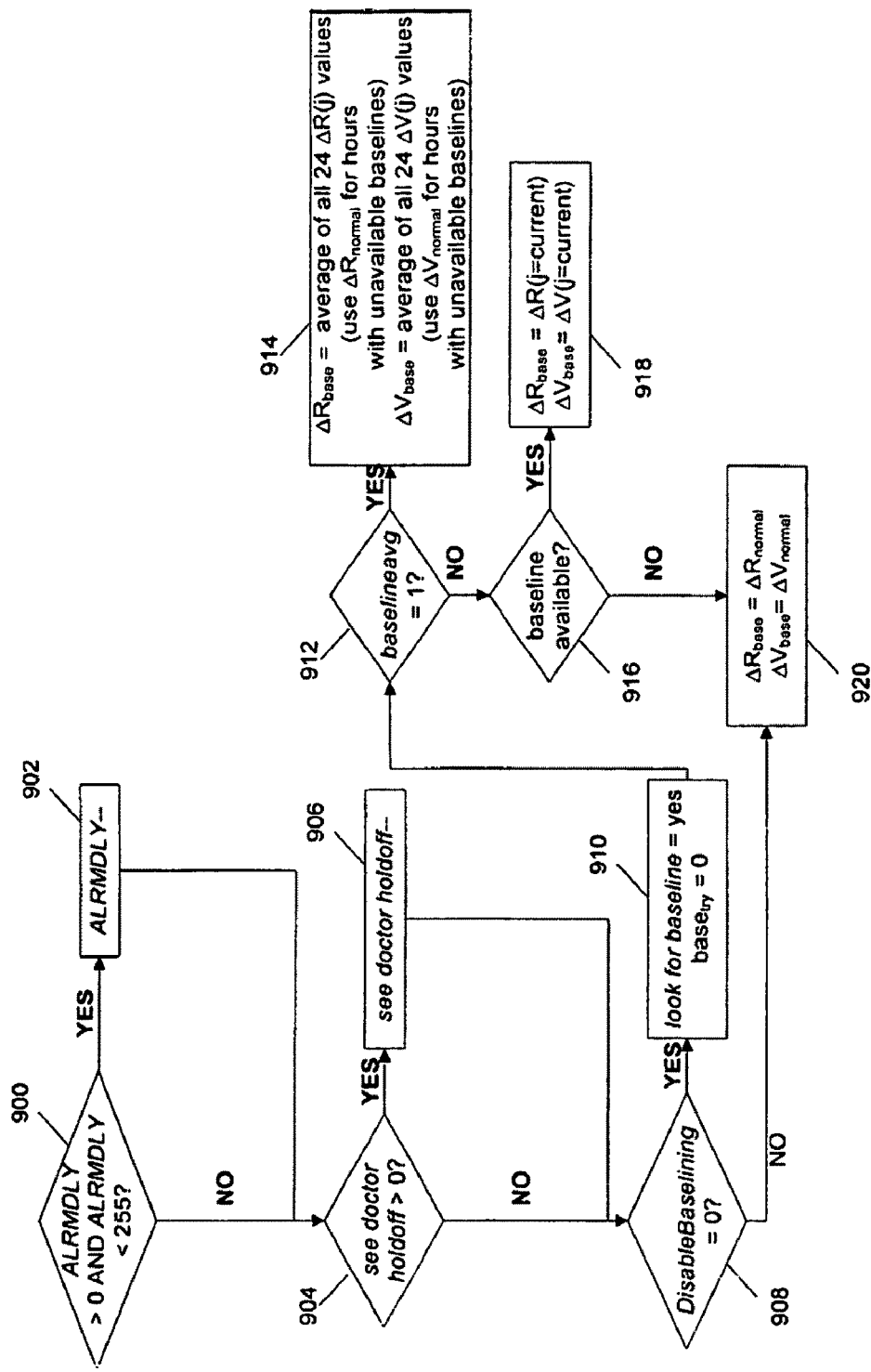
FIG. 7. is a block diagram of the hourly routine of the cardiosaver event detection program.
Figure 8:
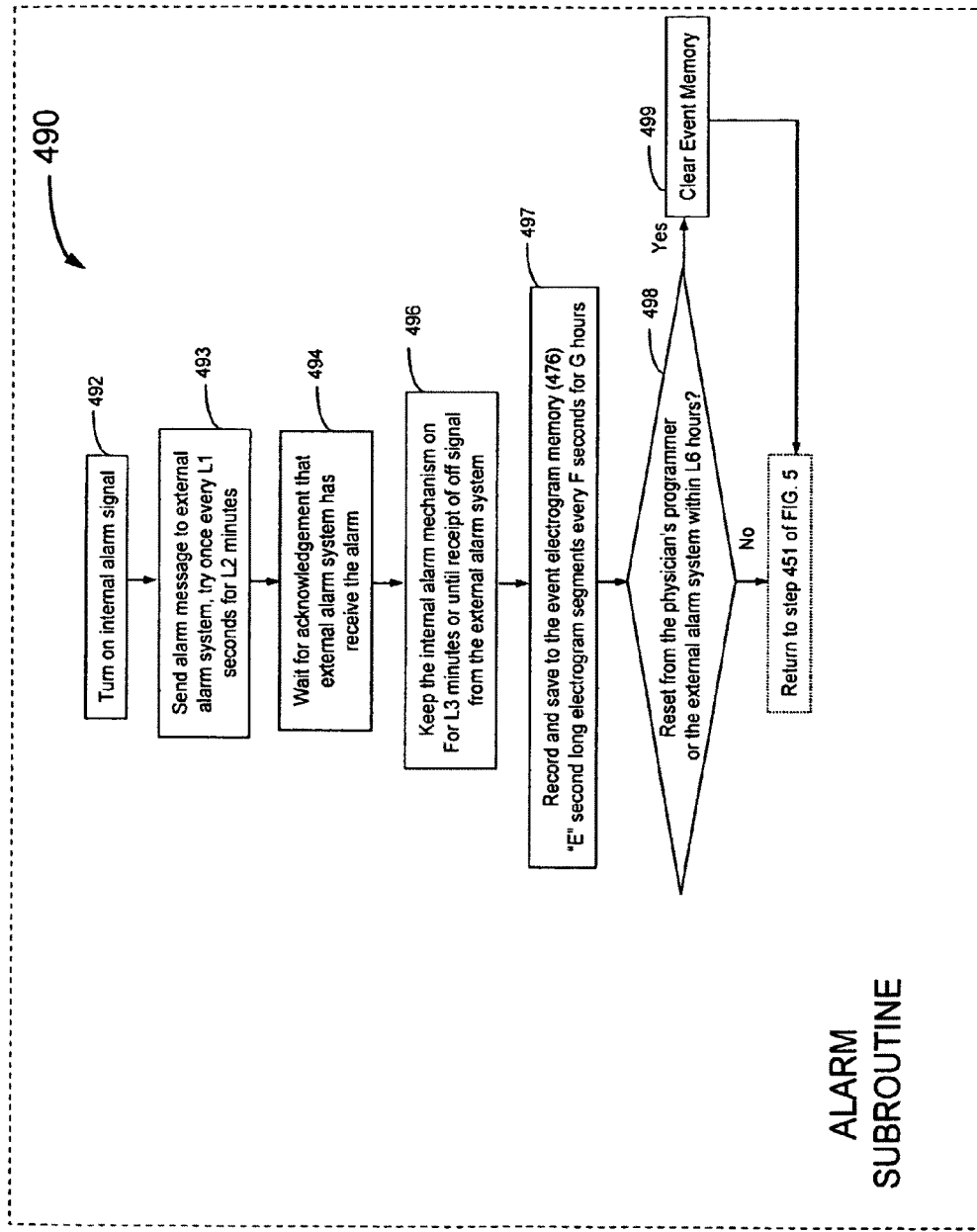
FIG. 8 is a block diagram of the alarm subroutine of the cardiosaver event detection program.

FIG. 7 illustrates a preferred embodiment of a periodically performed routine that is part of the program 450. The routine is run every Y minutes, with Y preferably set to 60 so that the routine is run once per hour. In block 900, the program 450 checks whether a timer, ALRMDLY, is between 0 and 255. This programmable timer allows alarms to be suppressed. If 0<ALRMDLY<255, then control passes to block 902, where ALRMDLY is decremented, such ALRMDLY keeps track of the number of hours before a detected condition should be allow to generate an alarm or alert vibration. (Vibrations are allow only with ALRMDLY is equal to 0. Note that if ALRMDLY is 0 it is not changed: i.e. is remains at 0. However, also note that if ALRMDLY is equal to 255, it also is not changed, i.e. it remains at 255. ALRMDLY is set to 255 at the factory, preventing any vibrations while on the shelf prior to implantation.

From either block 900 or block 902, control passes to block 904, which checks whether the "see doctor holdoff" counter (see doctor holdoff) is greater than 0. This counter provides a means for preventing multiple "See Doctor" alerts within a 24 hour period. It is set to 24 (hours) after any "See Doctor" alert occurs, thus ensuring that any subsequent conditions mapped to a "See Doctor" alert will have their vibrations suppressed. If see doctor holdoff is greater than 0, control passes to block 906, where see doctor holdoff counter is decremented (by one hour).

From either block 904 or 906, control passes to block 908, which checks whether baselining is enabled. In some cases, it may be desirable to turn off baselining, which is accomplished by setting a flag, DisableBaselining, to 1. If baselining is not disabled, (i.e. DisableBaselining=0), control passes to block 910, which sets the look for baseline flag to "yes". As previously mentioned, this flag is checked in block 832 of FIG. 5 to determine whether a current segment should be checked as a candidate for a baseline. Also in block 910, the counter $base_{try}$ is set to 0. This counter tracks the number of unsuccessful attempts to obtain a baseline. If it reaches a certain threshold, as will be further described with reference to FIG. 12, then no further attempts are made to find a baseline for the current hourly period.

Control passes to block 912, where the baselineavg variable is examined. This variable, which is externally programmable, dictates whether the values that will be used for determining ST shifts are composed of an average of baseline values or a single baseline value. If baseline averaging is enabled, control passes to block 914, which averages the baseline heart signal parameters that are used to determine ST shifts. As will be described with reference to FIG. 10, a baseline ST-PQ value, shown as $\Delta V$ (510) in FIG. 6, is used to determine ST shifts. Also, a baseline R to PQ amplitude $\Delta R = V_R - V_{PQ}$ (see FIG. 6 for examples of $V_R$ and $V_{PQ}$) is used to determine ST shifts. In block 914, the baseline $\Delta V$ value that will be used to determine ST shifts, $\Delta V_{BASE}$, is set equal to the average $\Delta V$ of the most recent U baselines, $(1/U)\Sigma\Delta V(j)$, where U is preferably 24 and $\Delta V(j)$ is the $\Delta V$ of the j'th baseline. (When U is 24 and baselines are collected hourly, as is preferable, $\Delta V_{BASE}$ is the average over one day, or 24 hours.) Similarly, the baseline $\Delta R$ value that will be used to determine ST shifts, $\Delta R_{BASE}$, is set equal to $(1/U)\Sigma\Delta R(j)$, where U is again preferably equal to 24 and $\Delta R(j)$ is the $\Delta R$ of the j'th baseline.

It is possible that baselines for some time slots are non-existent or have become too old, in which case, as will be further described with reference to FIG. 12, default values $\Delta V_{normal}$ and $\Delta R_{normal}$ may be used as the $\Delta V(j)$ and $\Delta R(j)$ for those time slots j for which a baseline was found to be non-existent or too old.

Instead of an average of the $\Delta V(j)$, some other statistical measure may be generated to compare against the current $\Delta V$. For example, a weighted average could be used whereby baselines corresponding to earlier time slots (e.g. >12 hours ago) are weighted more heavily than baselines corresponding to more recent time slots (e.g. <=12 hours ago). The exact nature of the averaging would depend on the expected normal rate of the change of $\Delta V$. Another alternative could involve taking the average of those $\Delta V(j)$ that fall within a standard deviation of the $\Delta V(j)$ distribution.

Returning to block 912, if baseline averaging is not enabled, control passes to block 916, which determines whether a baseline was collected U hours ago for the current hourly period. For example, if U is 24, and the hourly routine is run every hour on the hour, and it is currently 1:00 p.m., block 912 checks whether baseline values $\Delta V$ and $\Delta R$ for the 1:00 p.m. time slot are available, meaning that a baseline for that time slot was found fairly recently, preferably within the last three days (see FIG. 12 for more details). If so, in block 918, $\Delta V_{BASE}$ and $\Delta R_{BASE}$ are set equal to the $\Delta V$ and $\Delta R$ baseline values for the pertinent time slot (i.e. U hours ago). Otherwise, if baseline values $\Delta V$ and $\Delta R$ for that time slot are not available, default parameters $\Delta V_{normal}$ and $\Delta R_{normal}$ are used in block 620 for $\Delta V_{BASE}$ and $\Delta R_{BASE}$.

$\Delta V_{BASE}$ and $\Delta R_{BASE}$, computed in blocks 914, 918 or 920, are stored in the calculated baseline data memory 475 of FIG. 4.

FIG. 8. illustrates a preferred embodiment of the alarm subroutine 490. The alarm subroutine 490 is run when there have been a sufficient number of events detected to warrant a major event cardiac alarm to the patient. The alarm subroutine 490 begins with step 491

Next; in step 492 the internal alarm signal is turned on by having the CPU 44 of FIG. 4 cause the alarm sub-system 48 to activate a major event alarm signal.

Next in step 493 the alarm subroutine instructs the CPU 44 to send a major event alarm message to the external alarm system 60 of FIG. 1 through the telemetry sub-system 46 and antenna 35 of the cardiosaver 5 of FIG. 4. The alarm message is sent once every L1 seconds for L2 minutes. During this time step 494 waits for an acknowledgement that the external alarm has received the alarm message. After L2 minutes, if no acknowledgement is received, the cardiosaver 5 of FIG. 1 gives up trying to contact the external alarm system 60. If an acknowledgement is received before L2 minutes, step 495 transmits alarm related data to the external alarm system. This alarm related data would typically include the cause of the alarm, baseline and last event electrogram segments and the time at which the cardiac event was detected.

Next in step 496, the cardiosaver 5 transmits to the external alarm system 60 of FIG. 1 other data selected by the patient's physician using the programmer 69 during programming of the cardiosaver. These data may include the detection thresholds $H_{ST}(i)$, $H_T(i)$ and other parameters and electrogram segments stored in the cardiosaver memory 47.

Once the internal alarm signal has been activated by step 492, it will stay on until the clock/timing sub-system 49 of FIG. 4 indicates that a preset time interval of L3 minutes has elapsed or the cardiosaver 5 receives a signal from the external alarm system 60 of FIG. 1 requesting the alarm be turned off.

To save power in the implantable cardiosaver 5, step 496 might check once every minute for the turn off signal from the external alarm system 60 while the external alarm system 60 would transmit the signal continuously for slightly more than a minute so that it will not be missed. It is also envisioned that when the alarm is sent to the external alarm system 60, the internal clock 49 of the cardiosaver 5 and the external alarm system 60 can be synchronized so that the programming in the external alarm system 60 will know when to the second, that the cardiosaver will be looking for the turn off signal.

At this point in the alarm subroutine 490 step 497 begins to record and save to event memory 476 of FIG. 4, an E second long electrogram segment every F seconds for G hours, to allow the patient's physician and/or emergency room medical professional to read out the patient's electrogram over time following the events that triggered the alarm. This is of particular significance if the patient, his caregiver or paramedic injects a thrombolytic or anti-platelet drug to attempt to relieve the blood clot causing the acute myocardial infarction. By examining the data following the injection, the effect on the patient can be noted and appropriate further treatment prescribed.

In step 498 the alarm subroutine will then wait until a reset signal is received from the physician's programmer 68 or the patient operated initiator 55 of the external alarm system 60 of FIG. 1. The reset signal would typically be given after the event memory 476 of FIG. 4 has been transferred to a component of the external equipment 7 of FIG. 1. The reset signal will clear the event memory 476 (step 499) and restart the main program 450 at step 451.

If no reset signal is received in L6 hours, then the alarm subroutine 490 returns to step 451 of FIG. 5 and the cardiosaver 5 will once again begin processing electrogram segments to detect a cardiac event. If another event is then detected, the section of event memory 476 used for saving post-event electrogram data would be overwritten with the pre-event electrogram data from the new event. This process will continue until all event memory is used. I.e. it is more important to see the electrogram data leading up to an event than the data following detection.

Figure 9:
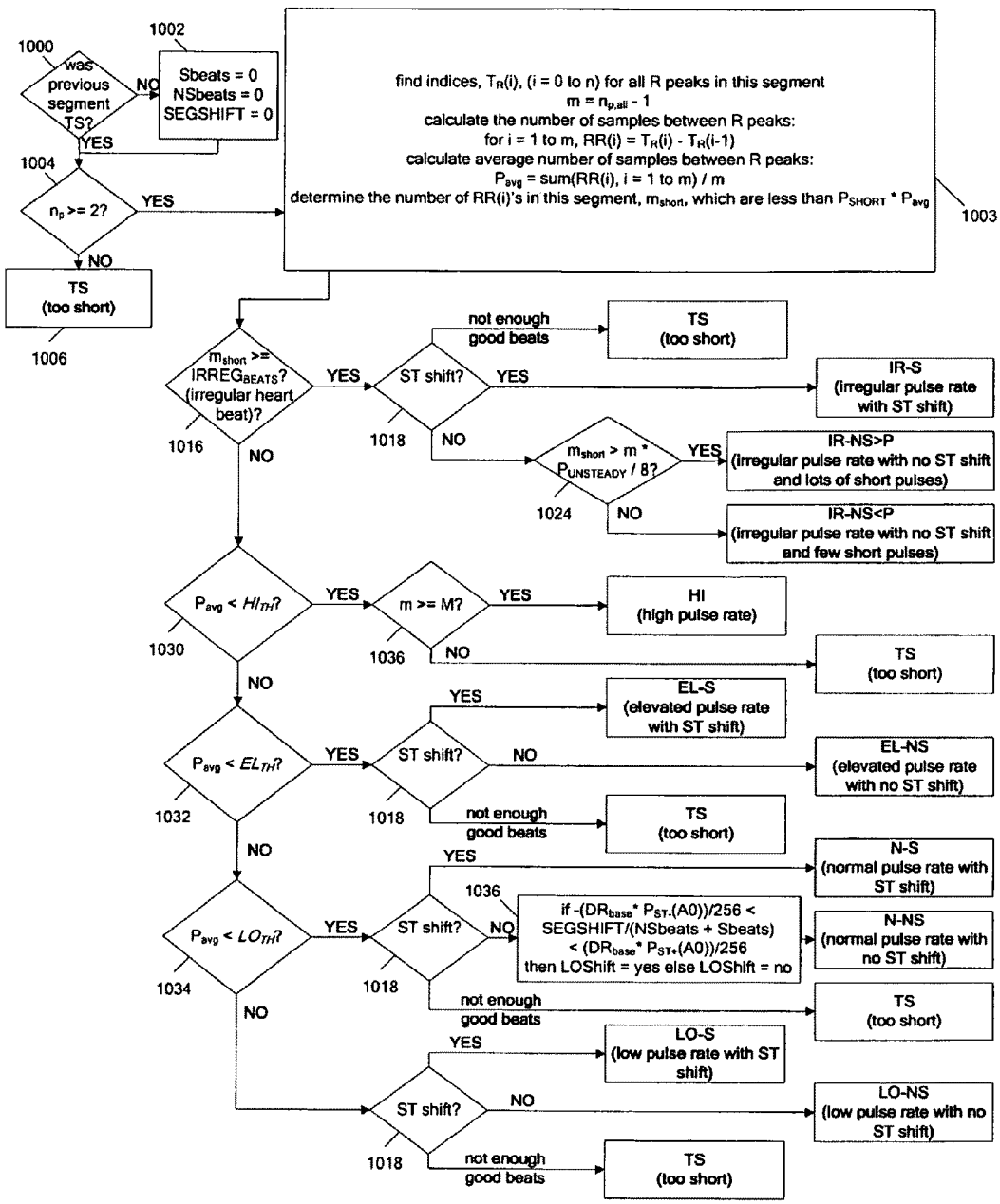
FIG. 9 is a block diagram of the data segment characterization subroutine of the cardiosaver event detection program.

FIG. 9 is a flow chart of the segment categorization routine of block 804 (FIG. 5). In block 1000, the program 450 examines whether the previous segment had too few good beats (i.e. was too short or TS). If so, the current segment will effectively be appended to the previous segment to create a compound segment.

If the previous segment was not too short, control passes to block 1002, where various variables (Sbeats, NSbeats and SEGSHIFT) are reset to 0. Sbeats and NSbeats track the number of ST shifted and non-ST shifted beats during a segment or run of segments. SEGSHIFT tracks the total sum of ST shifts during a segment or run of segments. These variables are reset to 0 in block 1002 because the previous segment was not too short.

Control transfers to block 1004, which checks whether the number of beats ($n_p$) in the segment is greater than or equal to 2. If not, the segment is too short, and is categorized as such in block 1006. As will be discussed below, the segment may be categorized as too short even if $n_p >= 2$.

If $n_p$ is greater than or equal to 2, as determined in block 1004, then control passes to block 1003, which involves a number of steps. First, the variable m, which is the number of beats to be analyzed, is set equal to $n_{p,all} - 2$, where $n_{p,all}$ is the number of R wave peaks in the segment to be categorized, which may be a compound segment. (I.e. $n_{p,all}$ is the number of R wave peaks in a segment, which may consist of a number of discrete "too short" single segments or a single segment with $n_p >= 2$.) 2 is subtracted from $n_{p,all}$ (in the $m = n_{p,all} - 2$ computation) because the first and last R wave peaks within the segment may not represent complete beats, i.e. the R-R interval before the first R wave peak may not be available from the segment data while the ST segment after the last R wave peak may not be available from the segment data.

The next step in block 1003 involves computing the number of samples between R wave peaks for the m beats to be processed, thereby computing R-R intervals RR(i), where i runs from 1 to m. Next, the average number of samples between R peaks ($P_{avg} = (1/m)\Sigma RR(i)$) is calculated for the m beats. The next step in block 1003 involves estimating the number of irregular beats ($m_{short}$) in the segment. If an RR(i) interval for a particular beat is much shorter than the average RR interval for the segment ($P_{avg}$), then some sort of arrhythmia may be occurring, e.g. that beat may be an ectopic beat. (Such a beat should also not be analyzed for ST shift.) Whether an RR(i) interval is considered to be abnormally short relative to other beats in the segment depends on the programmable parameter $P_{SHORT}$. Specifically, a beat is determined to be too short relative to other beats if its R-R interval is less than ($P_{SHORT}/256$) of $P_{avg}$. 205 is an exemplary value for $P_{SHORT}$, (which is results in ~80% (205/256) of $P_{avg}$ as the criteria).

In block 1016, the number of irregular beats $m_{short}$ is compared to a threshold $IRREG_{BEATS}$. If $m_{short} > IRREG_{BEATS}$, the segment is either irregular or too short. To determine whether the segment too short, and also to determine whether the segment is ST shifted, control passes to the ST shift routine denoted by block 1018. This routine will be described further below with reference to FIG. 10. The ST shift routine 1018 may categorize the segment as too short or ST shifted, in which case the segment is too short (TS) or irregular with an ST shift (IR-S), respectively. If the ST shift routine 1018 determines that the segment is sufficiently long and not ST shifted, control passes to block 1024, which determines whether the segment has a relatively large number or relatively small number of "short" beats by comparing the number of short beats ($m_{short}$) with a programmable fraction $P_{UNSTEADY}/8$ of the total number of beats in the segment m. An exemplary value of $P_{UNSTEADY}$ is 2 (resulting in a fraction of 25%). If $m_{short} > m^* P_{UNSTEADY}/8$, then the segment is categorized as irregular, non-ST shifted with a relatively large number of short beats (IR-NS>P). Otherwise, the segment is categorized as irregular, non-ST shifted with a relatively small number of short beats (IR-NS<P).

Returning to block 1016, if the number of irregular beats $m_{short}$ is less than $IRREG_{BEATS}$, so that the segment is not irregular, control passes to block 1030, which, along with blocks 1032 and 1034, categorizes the heart rate of the segment. These three blocks, 1030, 1032 and 1034, compare the average RR interval $P_{avg}$ to programmable thresholds $HI_{TH}$, $EL_{TH}$ and $LO_{TH}$, corresponding to high, elevated and low heart rates, respectively.

If the average RR interval suggests a high heart rate, block 1030 transfers control to block 1036, which determines if there are a sufficient number of beats in the segment by comparing the number of beats (m) with a programmable threshold M, which is preferably set to 6. This check is done to avoid characterizing a segment as a high heart rate segment based on only a few beats. A segment with a low $P_{avg}$ may have only a few beats when, for example, some actual heart beats are not detected and thus not included within the m beats. If $m >= M$, then the segment is characterized as a high heart rate segment (HI). Otherwise, it is categorized as too short (TS).

All other heart rate ranges (estimated by $P_{avg}$) are checked for ST shifts by the routine indicated by block 1018. In all of these heart rate types, elevated, normal, and low, the segment is placed into one of three categories depending upon whether the segment is ST shifted, and whether it is too short.

If the heart rate is normal, and the ST shift routine determines that the segment is not shifted and is not too short (i.e.

the segment is N-NS), then an additional check is made in block 1036 to determine whether the segment might qualify as an acceptable baseline. (As will be described with reference to the baseline routine outlined in FIG. 12, only N-NS segments may serve as baselines.) Specifically, block 1036 checks whether the average ST shift of the segment is less than half of the positive and negative thresholds. A flag, LOShift, which is used in the baseline routine as will be further described with reference to FIG. 12, is set accordingly.

Figure 10:
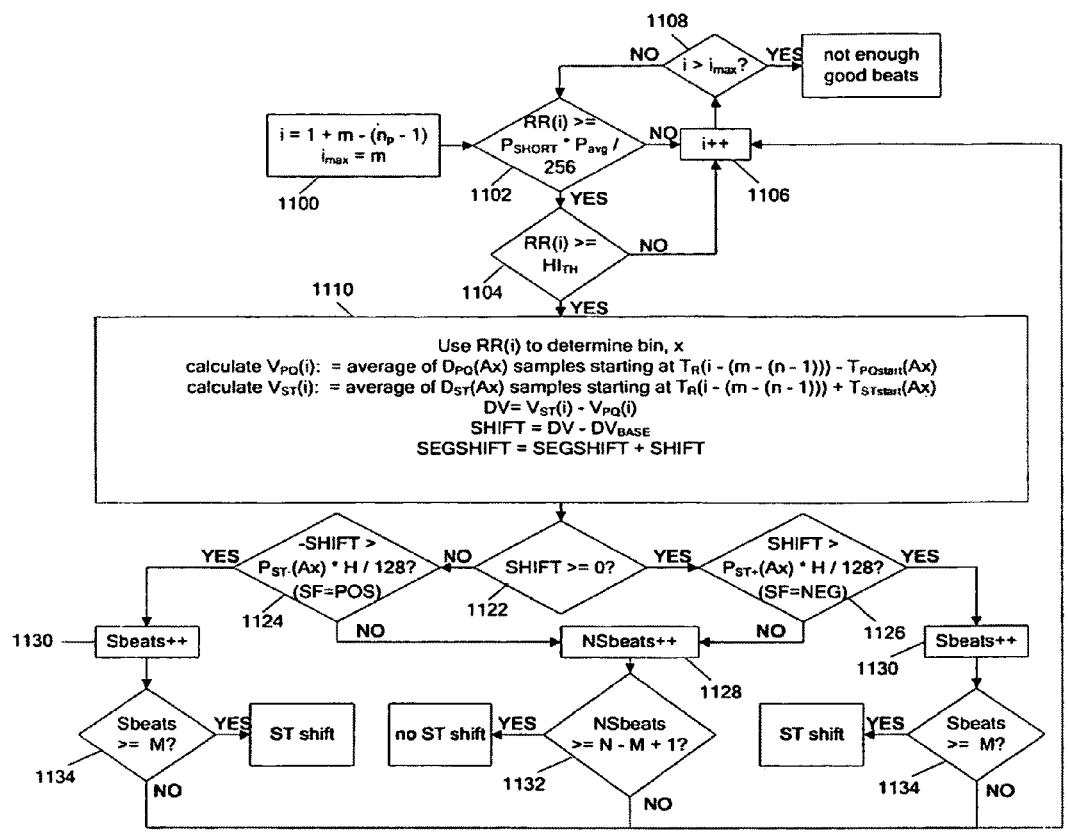
FIG. 10 is a block diagram of the ST shift subroutine of the cardiosaver event detection program.

FIG. 10 is a flow chart of the ST shift routine 1018. The ST shift detection routine checks beats that meet certain criteria for an ST shift ("ST analyzable beat"). The criteria a beat must meet in order to be checked for ST shift (i.e. to be an ST analyzable beat) are that the beat's period is not "too short" and not characterized by a high heart rate. The segment (which may be a compound segment) is declared to have an ST shift if M out of N "good" beats have an ST shift. The routine is structured to keep a running count of the number of beats with and without an ST shift. There are 3 possible outcomes: M beats with an ST shift are found before N−M+1 beats without an ST shift, N−M+1 beats without an ST shift are found before M beats with an ST shift, or the segment doesn't have ST analyzable beats for either of the previous conditions to be met. For example, the default values of M and N are 6 and 8, respectively. That means if 6 shifted beats are found before 3 non-shifted beats are found, the segment is declared to have an ST shift. Conversely, if 3 non-shifted beats are found before 6 shifted beats are found, the segment is declared to not have an ST shift. Note that this means (using these default values for M and N) that a determination can be made in as few as 3 ST analyzable beats and no more than 8 ST analyzable beats. This means that a segment with fewer than 8 ST analyzable beats may be TS (and a segment with 8 or more ST analyzable beats will never be TS).

Turning to FIG. 10, in block 1100, an index i is set equal to the index of the first beat to be analyzed, and $i_{max}$, which the index can not exceed, is set equal to m, the number of beats to be analyzed. If the current segment is not a compound segment, i is set equal to 1, the first beat to be analyzed. Otherwise, the segment is compound, and i is set so that it points to the first beat of the most recently acquired segment, the previously acquired segments) in the compound segment already having been analyzed. Thus, i is set equal to $1+m-(n_p-1)$, where $n_p$ is the number of peaks in the most recently acquired segment.

In block 1102, the beat referenced by i is checked to determine whether it is too short by comparing its RR interval with $P_{SHORT}/256 * P_{avg}$. If the RR interval (RR(i)) is too small according to a comparison with other beats in the segment ($P_{SHORT} * P_{avg}/256$), thereby indicating a short beat, the beat is not analyzed for an ST shift. More generally, beats associated with abnormal rhythms, as indicated by some heart rhythm parameter such as RR interval, may not represent a normal ST shift, and therefore it is preferable to exclude such beats from the segment for the purposes of analyzing ST shift. Control passes to block 1106, which increments i so that it points to the next beat. Control then transfers to block 1108, which checks if the last beat has been reached. If so, there are not enough good beats in the segment. (For segments with enough good beats, the logic of the ST shift routine 1018 is configured such that the routine exits before i reaches $i_{max}$.)

Returning to block 1102, if the RR interval (RR(i)) is greater than or equal to $P_{SHORT}/256 * P_{avg}$, control passes to block 1104, where RR(i) is compared to the threshold RR interval for high heart rate ($HI_{TH}$). If the RR interval is too short, indicating too high a heart rate, the beat is not analyzed for ST shift and control transfers to block 1106.

If the RR interval is sufficiently long, control passes to block 1110, which selects the appropriate heart rate bin based on the RR interval. In the preferred embodiment, there are 5 different heart rate ranges that have corresponding ST shift thresholds and other parameters that govern the analysis of various portions of a beat. In particular, the start of the PQ segment (measured as the number of samples backward from the R wave peak; see FIG. 6), the duration of the PQ segment ($D_{PQ}$, in units of samples), the start of the ST segment (measured as the number of samples after the R wave peak), the duration of the ST segment ($D_{ST}$, in units of samples), and the fraction of baseline R to PQ amplitude ($\Delta R_{BASE}=V_{R,BASE}-V_{PQ,BASE}$) to use as positive and negative ST shift thresholds, respectively. These programmable parameters are listed in the table below.

| heart rate bin | min # of samples between peaks | max # of samples between peaks | start of PQ (samples before R peak) | duration of PQ (samples after start of PQ) | start of ST (samples after R peak) | duration of ST (samples after start of ST) | fraction of average $(V_R - V_{PQ})$ for baseline to use as positive ST threshold | fraction of average $(V_R - V_{PQ})$ for baseline to use as negative ST threshold |
|---|---|---|---|---|---|---|---|---|
| A4 | $HI_{TH}$ | $A3_{TH} - 1$ | $T_{PQstart}(A4)$ | $D_{PQ}(A4)$ | $T_{STstart}(A4)$ | $D_{ST}(A4)$ | $P_{ST+}(A4)$ | $P_{ST-}(A4)$ |
| A3 | $A3_{TH}$ | $A2_{TH} - 1$ | $T_{PQstart}(A3)$ | $D_{PQ}(A3)$ | $T_{STstart}(A3)$ | $D_{ST}(A3)$ | $P_{ST+}(A3)$ | $P_{ST-}(A3)$ |
| A2 | $A2_{TH}$ | $A1_{TH} - 1$ | $T_{PQstart}(A2)$ | $D_{PQ}(A2)$ | $T_{STstart}(A2)$ | $D_{ST}(A2)$ | $P_{ST+}(A2)$ | $P_{ST-}(A2)$ |
| A1 | $A1_{TH}$ | $EL_{TH} - 1$ | $T_{PQstart}(A1)$ | $D_{PQ}(A1)$ | $T_{STstart}(A1)$ | $D_{ST}(A1)$ | $P_{ST+}(A1)$ | $P_{ST-}(A1)$ |
| A0 | $EL_{TH}$ | — | $T_{PQstart}(A0)$ | $D_{PQ}(A0)$ | $T_{STstart}(A0)$ | $D_{ST}(A0)$ | $P_{ST+}(A0)$ | $P_{ST-}(A0)$ |

In the case of a beat following an ectopic beat, the R-R interval may be very long because ectopic beats often have an unusually long ST/T/PQ segment, which would result in that following beat being put into a lower heart rate bin than it should be placed. However, that beat following the ectopic beat may often have an ST duration ($D_{ST}$) and other duration related parameters that are associated with a higher rate (i.e. the normal heart rate, excluding the ectopic beat.) In such a case, if an ectopic beat is detected, by for example comparing the R-R interval with the average R-R interval of a segment, then the beat following the ectopic beat may be assigned an R-R interval equal to the average R-R interval of the segment.

In the discussion below, Ax refers to the heart rate bin corresponding to x. For example, $D_{PQ}(Ax)$ is the duration of the PQ segment, where Ax can be A0, A1, A2, A3 or A4.

Also in block 1110, the PQ segment voltage is calculated as $V_{PQ}(i)$=average value of $D_{PQ}(Ax)$ samples starting at the sample defined by $T_R(i-(m-(n_p-1)))-T_{PQstart}(Ax)$. ($T_R$ is the number of the sample at which the peak of the R wave occurs.) Similarly, in block 1114, the ST segment voltage is calculated as $V_{ST}(i)$=average value of $D_{ST}(Ax)$ samples starting at the sample defined by $T_R(i-(m-(n_p-1)))+T_{STstart}(Ax)$.

Also in block 1110, the ST deviation ($\Delta V$ in FIG. 6) of the beat is calculated as $\Delta V=V_{ST}(i)-V_{PQ}(i)$. The ST shift, which compares the current ST deviation with the baseline ST deviation ($\Delta V_{BASE}$) is calculated as SHIFT=$\Delta V-\Delta V_{BASE}$. The cumulative ST shift for the entire segment is calculated by adding the current SHIFT to SEGSHIFT. (As mentioned, SEGSHIFT is used to compute the average ST shift for the beats in a segment that were analyzed for ST shift, as mentioned with reference to block 1036 in FIG. 9).

In block 1122, the polarity of the ST shift, positive or negative, is determined, so that different threshold tests can be applied depending on polarity, where the threshold tests indicate whether a beat is sufficiently shifted to be considered shifted. Beats with a shift greater than or equal to 0 are tested in block 1124 while negative shifted beats are tested in block 1126. In each case, the SHIFT is compared with a heart rate dependent fraction ($P_{ST+}(Ax)/128$ or $P_{ST-}(Ax)/128$) of the baseline R to PQ amplitude ($\Delta R_{BASE}$). $\Delta R_{BASE}$ serves as a proxy for signal strength, so a fraction of $\Delta R_{BASE}$ (i.e. $\Delta R_{BASE}*f$, where f is $P_{ST+}(Ax)/128$ or $P_{ST-}(Ax)/128$) is the amplitude of ST shift that is considered above threshold given the current signal strength.

In an alternate embodiment, the segment is tagged with a variable SF as having either a positive shift (block 1124) or a negative shift (block 1126).

If the beat is below the ST shift threshold, the count of non-shifted beats (NSbeats) is incremented in block 1128. In block 1132, a test is performed to determine if the segment already has enough non-shifted beats to avoid being categorized as a shifted segment, regardless of whether any additional beats in the segment are shifted. Recalling that M out of N beats are required to categorize a segment as shifted, N−M+1 beats without an ST shift mean that the segment can not have M shifted beats and is thus not shifted. Thus, in block 1132, if NSbeats>=N−M+1, then the segment is not shifted, and the ST shift routine exits. Otherwise, the next beat is analyzed starting with block 1106.

If the shift of the beat is above the ST shift threshold as determined by blocks 1124 or 1126, the count of shifted beats (Sbeats) is incremented in block 1130. In block 1134, the number of shifted beats Sbeats is compared with M, the number of beats required to categorize a segment as shifted. If Sbeats>=M, then the segment is shifted and the ST shift routine exits. Otherwise, the next beat is analyzed starting with block 1106.

The above described structure of the ST shift routine ensures that segments with less than M beats, and having less than N−M+1 good beats, are categorized as too short. For example, if a segment consists of 5 shifted beats, it is not considered shifted because it has less than M (=6) shifted beats. When the routine reaches block 1108 after processing the fifth beat, it will categorize the segment as too short and exit. A subsequent segment (or segments) will be appended to the segment to create a compound segment that is long enough to categorize as shifted or non-shifted. The number of shifted and non-shifted beats (Sbeats and NSbeats) for the current segment as well as SEGSHIFT are stored and may be incremented while processing the subsequent segment. In this manner, the total number of shifted and non-shifted beats (and SEGSHIFT) in a compound segment are tracked as consecutive TS segments are processed sequentially. As mentioned, once a segment is sufficiently long to categorize for ST shift, the Sbeats, NSbeats and SEGSHIFT are reset to 0 in block 1002 (FIG. 9) for the next segment.

Figure 11:
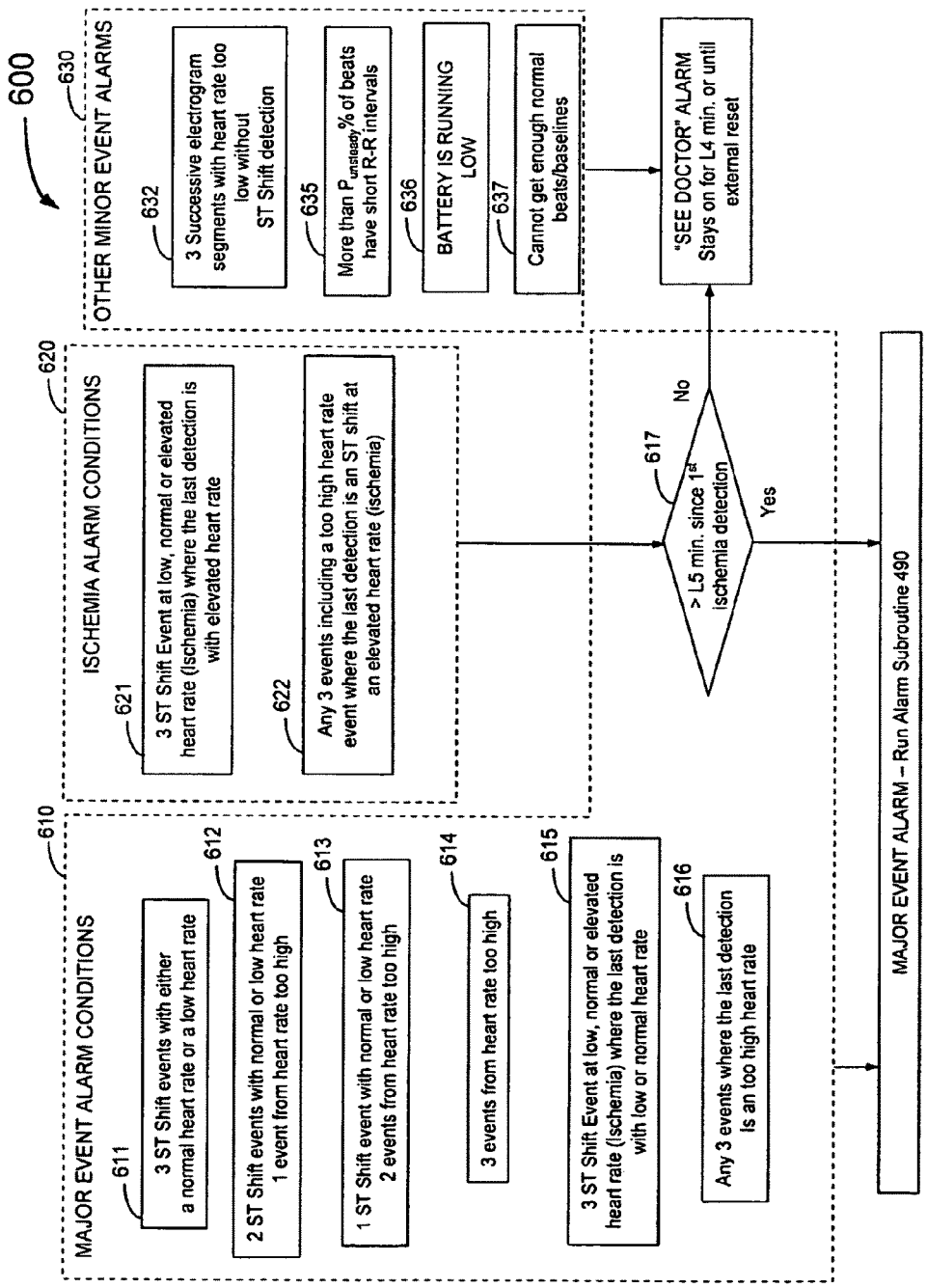
FIG. 11 diagrams the alarm conditions that are examples of the combinations of major and minor events that can trigger an internal alarm signal (and/or external alarm signal) for the guardian system of FIG. 1.

FIG. 11 diagrams the alarm conditions 600 that are examples of the combinations of major and minor events that can trigger an internal alarm signal (and/or external alarm signal for the guardian system of FIG. 1. Box 610 shows the combinations 611 through 617 of major cardiac events that can cause the alarm subroutine 490 to be run. These include the following:

| | |
|---|---|
| 611. | 3 ST shift events (detections of excessive ST shift) with either a normal heart rate or a low heart rate. |
| 612. | 2 ST shift events with a normal or low heart rate and 1 event from heart rate too high. |
| 613. | 1 ST shift event with a normal or low heart rate and 2 events from heart rate too high. |
| 614. | 3 events from heart rate too high. |
| 615. | 3 ST shift events with either a normal, low or elevated heart rate (ischemia) where the last detection is at a normal or low heart rate. |
| 616. | 3 events (excessive ST shift or high heart rate) where the last event is high heart rate. |
| 617. | An ischemia alarm indication from conditions in box 620 that remains for more than L5 minutes after the first detection of ischemia. |

The ischemia alarm conditions 620 include:

| | |
|---|---|
| 621. | 3 ST shift events with either a normal, low or elevated heart rate (ischemia) where the last detection is at an elevated heart rate. |
| 622. | Any 3 events including a too high heart rate event where the last detection is an excessive ST shift at an elevated heart rate. |

If either of the ischemia alarm conditions 620 is met and it is less than L5 minutes since the exercise induced ischemia was first detected, then the SEE DOCTOR ALERT signal will be turned on by step 682 of the ischemia subroutine 480 if it has not already been activated.

Box 630 shows the other minor event alarm conditions including the bradycardia alarm condition 632 that is three successive electrogram segments collected with heart rate too low and the unsteady heart rate alarm condition 635 that is caused by more than $P_{unsteady}\%$ of beats having a too short R-R interval.

These will trigger the SEE DOCTOR alert signal initiated by step 427 of the hi/low heart rate subroutine 420 for the bradycardia alarm condition 632 and step 416 of the unsteady hart rate subroutine 410 for the unsteady heart rate alarm condition 635. Also triggering the SEE DOCTOR alert signal is a low battery condition 636.

Figure 12:
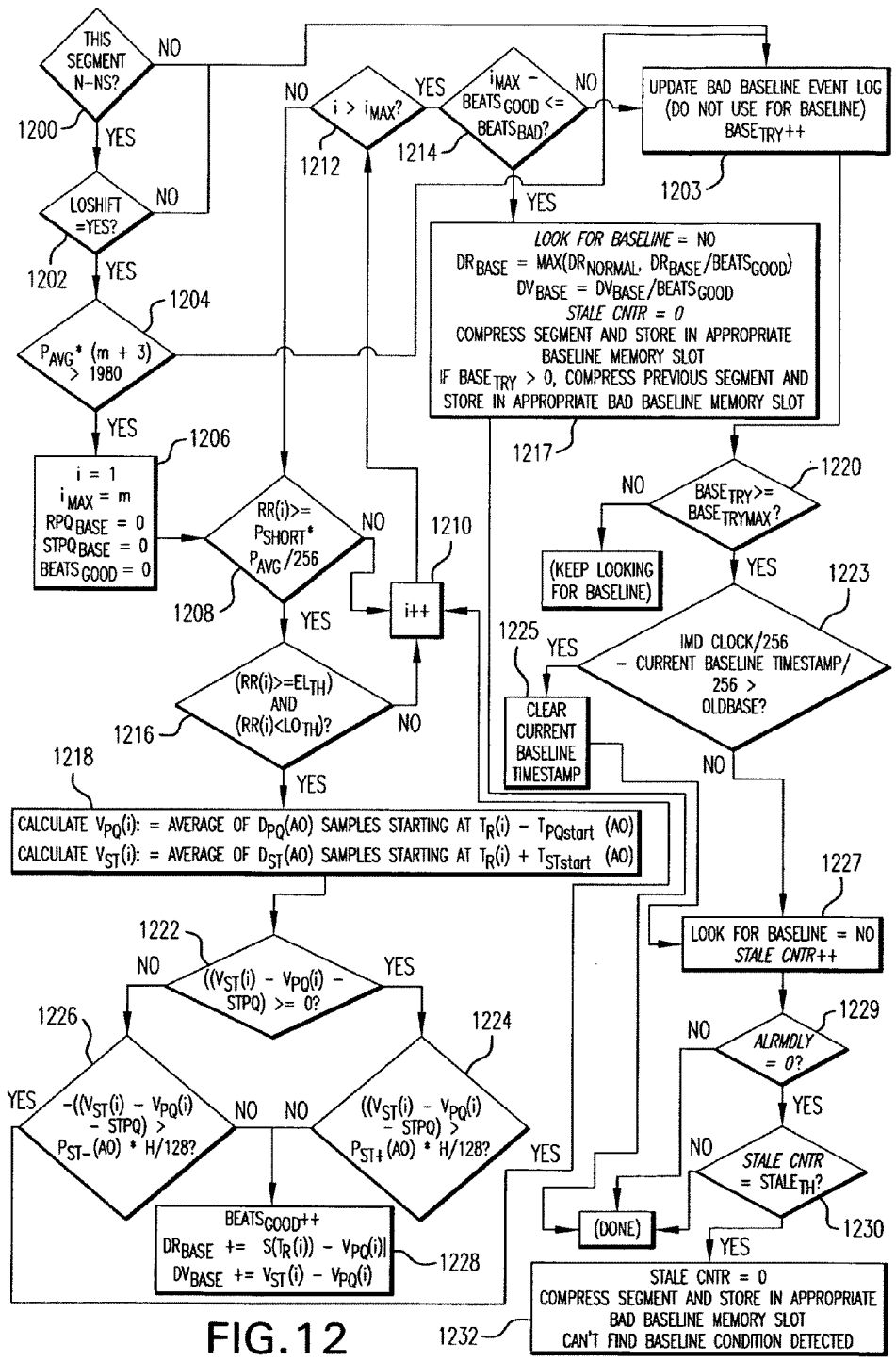
FIG. 12 is a block diagram of the baseline parameter extraction subroutine of the cardiosaver event detection program.

FIG. 12 is a flow chart of procedure that checks whether a segment qualifies as a baseline and, if so, calculates the baseline quantities $\Delta R(j)$ and $\Delta V(j)$, where j indexes the current time slot (i.e. one of 24 hours if baselines are acquired hourly)

In block 1200 the program 450 checks whether the segment was classified as having a normal heart rate and no ST shift (N−NS). If not, the segment can not be a baseline and, as will be further described below, various checks are made to determine if too many unsuccessful attempts have been made to find a baseline, which may indicate an alarmable condition.

Otherwise, if the segment is N-NS, additional preliminary checks are made to determine whether the segment may qualify as a baseline. In block 1202, if the LOSHIFT variable has been set in block 1036 of FIG. 9), which indicates that the segment is somewhat ST shifted but not enough to be considered a physiological problem, the segment can not qualify as a baseline. If LOSHIFT has not been set, control passes to block 1204. There a check is made to make sure that segment being examined has beats through out the segment. (That is, a segment with 5 beats in the first 5 seconds of the segment and no beats in the second 5 seconds of the segment should not be used as a baseline segment. Formally, this check is performed by comparing ($P_{avg}$*(m+3)>1980).

If the segment is not disqualified by the preliminary tests in blocks 1200, 1202 and 1204, each beat in the segment is checked in a manner similar to the ST shift routine, the major difference being that N−M+1 beats good, non-shifted beats does not necessarily qualify a segment as a baseline. Instead, a more stringent test, which requires that the total number of "bad beats" be below a threshold ($BEATS_{BAD}$) is applied. Also, in the baseline routine, running totals of the R to PQ height ($V_R-V_{PQ}$) and ST deviation are kept so that the $\Delta R(j)$ and $\Delta V(j)$ quantities can be calculated for the segment if it qualifies as a baseline.

In block 1206, as in the ST shift routine, the beat index i is set to 1, $i_{max}$ is set to m. In addition, $RPQ_{base}$, $STPQ_{base}$ and $Beats_{good}$ variables are set to 0., $RPQ_{base}$ and $STPQ_{base}$ are running totals of the R to PQ height ($V_R-V_{PQ}$ in FIG. 6) and ST deviation ($\Delta V$ in FIG. 6). $Beats_{good}$ is the total number of good, non-shifted beats. In block 1208, the beat referenced by i is checked to determine whether it is too short by comparing its RR interval with $P_{SHORT}/256$*$P_{avg}$. If the RR interval (RR(i)) is too small according to a comparison with other beats in the segment ($P_{SHORT}$*$P_{avg}/256$), thereby indicating a short beat, the beat is not analyzed for an ST shift. Control passes to block 1210, which increments i so that it points to the next beat. Control then transfers to block 1212, which checks if the last beat has been reached. If so, control transfers to block 1214, which will be further described below. Otherwise, control returns to block 1208.

Returning to block 1208, if the RR interval (RR(i)) is greater than or equal to $P_{SHORT}/256$*$P_{avg}$, the beat is then checked to see if it is in the normal heart rate bin. In block 1216, RR(i) is compared to the threshold RR intervals for low heart rate ($EL_{TH}$) and elevated heart rate ($LO_{TH}$), respectively, to ensure that the beat (i) is in the normal range. If the RR interval is too short or too long (i.e. the instantaneous heart rate is too high or too low, respectively), the beat is not analyzed for ST shift and control transfers to block 1210.

Otherwise, in block 1218, the PQ segment voltage is calculated as $V_{PQ}(i)$=average value of $D_{PQ}(A0)$ samples starting at the sample defined by $T_R(i)-T_{PQstart}(A0)$. (Again, $T_R$ is the number of the sample at which the peak of the R wave occurs.) Similarly, the ST segment voltage is calculated as $V_{ST}(i)$= average value of $D_{ST}(A0)$ samples starting at the sample defined by $T_R(i)+T_{STstart}(A0)$.

In block 1222, the polarity of the beat i's ST shift, positive or negative, is determined, so that different threshold tests can be applied depending on polarity. As in the ST shift routine, the ST shift is $V_{ST}(i)-V_{PQ}(i)-\Delta V_{BASE}$. Positive (or non-shifted) beats are tested in block 1224 while negative shifted beats are tested in block 1226. As in the ST shift routine, the ST shift is compared with a fraction ($P_{ST+}(A0)/128$ or $P_{ST-}(A0)/128$) of the baseline R to PQ amplitude ($\Delta R_{BASE}$).

If the beat's ST shift is below the positive or negative threshold (whichever applies), in block 1228, the beat's R to PQ height ($V_{PQR}=|V(T_R(i))-V_{PQ}(i)|$) is added to the running total $RPQ_{base}$ and the beat's ST deviation ($V_{ST}(i)-V_{PQR}(i)$) is added to $STPQ_{base}$. Also, the $Beats_{good}$ counter, which tracks the number of good, non-ST shifted beats, is incremented. Control then transfers back to block 1210.

Returning to block 1224 or block 1226, whichever applies, if the beat's ST shift is above the positive or negative threshold (whichever applies), the beat is effectively excluded from the segment by skipping block 1228. Specifically, control is transferred to block 1210.

Moving forward to block 1214, if the number of bad beats ($=i_{max}-Beats_{good}$) is less than or equal to a threshold, ($BEATS_{BAD}$), preferably set to 1, then the segment qualifies as a baseline and control passes to block 1217. The "look for baseline" flag is set to 0 since the baseline has been found. The average $\Delta R$ for the segment is set equal to $RPQ_{base}/Beats_{good}$. However, if this value is too small, it will not be used as $\Delta R(j)$ for the time slot because small values of $\Delta R$ can bias checks for ST shifts. Specifically, in both the ST shift routine and the baseline routine, ST shifts are determined by comparing ST deviations with a threshold defined by a fraction of baseline $\Delta R_{BASE}$. Thus, if $\Delta R_{BASE}$ was very small, then the threshold may be very small. Consequently, small ST shifts could be above threshold, which is not desirable. To avoid this problem, $\Delta R(j)$ for any time slot is never allowed to be smaller than a parameter $RPQ_{normal}$, which is preferably equal to 100.

The baseline's ST deviation $\Delta R(j)$ is set equal to the average ST deviation for the good beats in the segment $S_{TPQ}/Beats_{good}$. A counter (stale cntr) which keeps track of how many consecutive hours a new baseline has not been found, is reset to 0. The segment is compressed, preferably according to the turning point algorithm, and stored in an appropriate baseline memory slot. If this segment is not the first segment in the hour to be checked, then a counter $base_{try}$ will be greater than 0, in which case the previous segment is compressed and stored in an appropriate slot for bad baselines. (The operation of the counter $base_{try}$ will be further described below.) From block 1217, the baseline checking routine exits.

Returning to block 1214, if the number of bad beats ($=i_{max}-Beats_{good}$) is greater than $BEATS_{BAD}$, then the segment is disqualified as a baseline and control passes to block 1203, where a bad baseline event log is updated. Also, the counter $base_{try}$, which tracks the number of unsuccessful attempts made to find a baseline, is incremented. Control passes to block 1220, which checks whether the number of unsuccessful attempts made to find a baseline ($base_{try}$) exceeds a threshold $BASE_{trymax}$.

If not, the routine simply exits. Otherwise, control passes to block 1223, which checks how long ago the existing baseline for the current time slot was acquired. Specifically, the time that a good baseline for the current time period was found (current baseline timestamp) is subtracted from the current time kept by the clock 49 (see FIG. 4). If this difference is too large, as measured by a threshold oldbase which is preferably set to 84 hours (3.5 days), then the baseline is considered too old and is discarded. Instead, as mentioned in connection with blocks 914 and 920 in FIG. 7, default parameters $\Delta V_{normal}$ and $\Delta R_{normal}$ will used in block 620 for $\Delta V_{BASE}$ and $\Delta R_{BASE}$ until such time as a baseline segment is found for this time slot. In block 1225, the baseline's time stamp is cleared (effectively discarding it).

From either block 1225 or block 1223, control transfers to block 1227 which sets the look for baseline flag to "no" to indicate that no further attempts should be made to find a baseline for the current time slot. The stale cntr, which keeps track of the number of consecutive time slots which have had unsuccessful attempts to find a baseline, is incremented.

Inability to collect baselines (a "can't find baseline" condition) may arise from a number of causes. For example, if the patient's beta blockers have stopped working or the dose it too low, the patient might have an elevated heart rate for many hours so that the heart is never in the normal heart rate range. In fact, checking for a consistent inability to find baselines is a very useful procedure in that any cause of the patient's heart not having any "normal" segments over the baseline alert time period will trigger the alarm subroutine. Such causes can either be related to the patient's heart or they may be caused by misconfigured heart rate bins or by a fault in the software or electrical circuitry of the implant. Inability to collect baselines will typically trigger a "See Doctor" alert using alert routine 639 of the alarm subroutine 490.

However, the alarm may be suppressed, depending on the value of ALRMDLY. (See blocks 900 and 902 in FIG. 7 and corresponding discussion.) In block 1229, if ALRMDLY is not 0, the routine exits. Typically, ALRMDLY is non-zero prior to implantation. This check prevents continuous "can't find baseline" alerts while the device is on the shelf.

If ALRMDLY is 0, control passes to block 1230, which compares stale cntr to $STALE_{TH}$. If stale cntr is not equal to $STALE_{TH}$, then the routine exists. Otherwise, control passes to block 1232, which involves compressing the segment and storing it in the appropriate bad baseline memory slot, and setting a flag indicating a "can't find baseline" condition has been detected.

Figure 13:
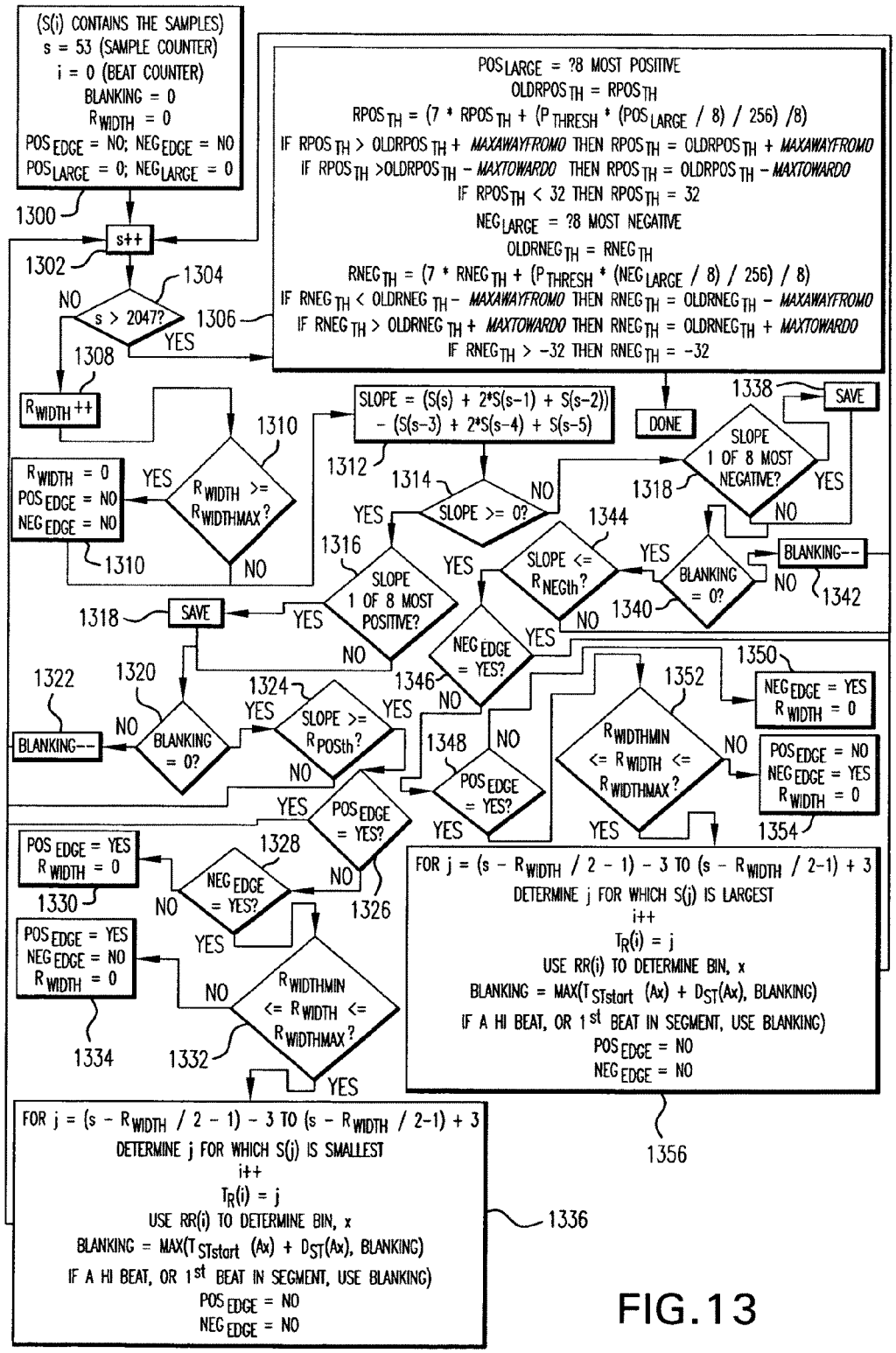
FIG. 13 is block diagram of the R wave peak detection subroutine of the cardiosaver event detection program.

FIG. 13 is a flow chart of the R peak detection routine. Peaks are located by looking for one more large magnitude slopes (positive or negative) followed by some, but not too many, samples with a small magnitude slope, which in turn are followed by a large magnitude slope of the opposite direction. If all of these conditions have been met, a peak has been found somewhere within the set of samples that satisfied the above conditions. Once a peak has been found, the routine does not look for another peak until after the end of the beat's ST segment (if known) or for a blanking interval defined by a certain number of samples (BLANKING), whichever is greater.

Throughout the discussion of this flowchart, S represents an array that contains samples corresponding to the current data segment. The counter s, which represents the current sample, indexes into the array S, so that S(s) is the $s^{th}$ sample. As before, "i" is the beat counter. In block 1300, s is set to 53. The first 48 samples are discarded to avoid start-up transient, to make room in memory for header information, and to get a 10.00 second segment. After these 48 samples, the routine starts on the $6^{th}$ sample, because of the slope calculation, explained below. Also in block 1300, the beat counter "i" is set to 0, as well as the following variables: "blanking", "$R_{width}$", "$POS_{LARGE}$" and "$NEG_{LARGE}$". Variables "$POS_{EDGE}$" and "$NEG_{EDGE}$" are set to "no". The role of these variables will be described below. Finally, the memory that stores the 8 most positive and negative slopes for the segment is cleared.

In block 1302, the s counter is incremented. In block 1304, the routine checks whether the last sample in the segment, sample 2048, has been reached. If so, final segment processing is performed in block 1306, which will be described below. Otherwise, control passes to block 1308, which increments the $R_{width}$ counter, which tracks the width of the current R wave (i.e. the R wave of the i'th beat.). In block 1310, the R width is compared to a programmable threshold, $R_{WIDTHMAX}$ (preferably set to 10). If $R_{width} >= R_{WIDTHMAX}$, then the current candidate for an R wave (tracked by $R_{width}$) is considered not to be an R wave. This check helps to prevent T waves, which may otherwise appear to be R waves due to sharp upstrokes and downstrokes but are generally wider than R waves, from being considered as R waves. If $R_{width} >= R_{WIDTHMAX}$, control passes to block 1310, which resets $R_{width}$ to 0 and sets "$POS_{EDGE}$" and "$NEG_{EDGE}$" each to "no", Control is transferred to block 1312, which also is reached directly from block 1310.

Block 1312 calculates the slope of the electrogram in the neighborhood of the current sample s. In particular, the slope at s is set equal to: (S(s)+2*S(s-1)+S(s-2))-(S(s-3)+2*S(s-4)+S(s-5)). Control passes to block 1314, which checks whether the slope is positive or 0. Positive and negative slope sub-segments are processed in asymmetrical manner by routines starting at blocks 1316 and 1318, respectively. The only difference between these procedures pertains to the polarity of tests (e.g. the positive slope procedure will check if the slope is greater than a threshold while the negative slope procedure will check if the slope is less than a threshold.)

Turning to the positive slope procedure, block 1316 checks whether the slope is more positive than any of the eight slopes stored in the positive slope memory. If so, in block 1317, the slope is stored, replacing the least positive of the 8 stored slopes. From block 1317 or block 1316, control passes to block 1320, which checks whether the variable "blanking" is equal to 0. The value of this variable is the number of samples remaining in the blanking interval. If the blanking interval is not over, the current sample is skipped. The blanking interval is decremented in block 1322 and control returns to block 1302.

If the blanking interval is over, i.e. "blanking"=0, then control passes to block 1324, which checks whether the slope is sufficiently large to be considered an R wave upstroke by comparing the slope with a threshold $R_{POSth}$, which is dynamically adjusted in a manner to be described below. If the slope is less than $R_{POSth}$, control returns to block 1302. Otherwise, control passes to block 1326, which checks whether an upstroke has already been identified for the current beat by checking whether the $POS_{edge}$ variable is set to "yes." If so, control returns to block 1302.

Otherwise, control passes to block 1328, which checks whether a downstroke has already been identified for the current beat by checking whether the $NEG_{edge}$ variable is set to "yes." If not, then a peak has not yet been located. Control passes to block 1330, where the $POS_{edge}$ variable is set to "yes" to indicate that an upstroke has been found, and the $R_{width}$ is reset to 0 to begin tracking the width of what is possibly an R wave. Control again returns to block 1302.

Returning to block 1328, if the $NEG_{edge}$ variable is set to "yes", then the newly located upstroke possibly represents the upstroke of an R wave that consists of a "v" like downstroke followed by an upstroke. However, if the width between the upstroke and downstroke is too large, the data may represent a T wave rather than an R wave. Conversely, if the if the width between the upstroke and downstroke is too small, the data may represent a fluctuation (e.g. noise) that is not an R wave. To test for both of these possibilities, in block 1332, the procedure checks whether $R_{width}$ is greater than or equal to $R_{WIDTHMIN}$, and also less than or equal to $R_{WIDTHMAX}$, where $R_{WIDTHMIN}$ and $R_{WIDTHMAX}$ are programmable thresholds preferably set to 3 and 10, respectively. If $R_{width}$ does not fall within these thresholds, control passes to block 1334, where the $POS_{edge}$ variable is set to "yes" to indicate that an upstroke has been found, the $R_{width}$ is reset to 0 to begin tracking the width of what is possibly an R wave, and the $NEG_{edge}$ variable is set to "no". Control again returns to block 1302.

Returning to block 1332, if $R_{width}$ falls within the range defined by $R_{WIDTHMIN}$ and $R_{WIDTHMAX}$, then an R wave is detected and control transfers to block 1336. To find the peak, the sample with the minimum value (the bottom of the "v" shape) is located by searching through 6 samples centered around the sample that was $R_{width}/2$ samples before the current sample. More formally, for $j=(s-R_{width}/2-1)-3$ to $(s-R_{width}/2-1)+3$, the minimum S(j) is found. The R wave time $T_R(i)$ for beat i is set to the j that resulted in the minimum S(j). Next, the beat counter i is incremented to indicate that the $i^{th}$ R wave has been located. The RR(i) interval, defined as the number of samples between the current R wave peak and the previous R wave peak, is used to determine the appropriate heart rate bin (A0-A4) for the beat. The blanking interval is set such that it ends at the estimate of the end of the ST segment, unless the amount of time to the end of the ST segment is less than BLANKING, in which case BLANKING is used as the blanking interval.

The end of the ST segment is estimated by the heart rate dependent quantity ($T_{STstart}$(Ax)+$D_{ST}$(Ax)). If the beat is characterized as a high heart rate beat, or the beat is the first one in the segment, BLANKING is used as the blanking interval, (because the time of end of the ST segment is undefined for high heart rate beats and because the previous beat is not known for the first beat found in a segment, respectively). $POS_{edge}$ and $NEG_{edge}$ are both reset to "no" to indicate that the routine is searching for the next R wave. Control passes back to block 1302.

Returning to block 1314, if the slope is negative, control passes to block 1318. The subsequent processing is symmetrical to the processing for positive slopes, except with appropriate polarity changes. Thus, block 1318 checks whether the slope is one of the 8 most negative slopes. Block 1338 is identical to block 1318. Blocks 1340 and 1342 are identical to blocks 1320 and 1322. Block 1344 checks whether the slope is less than or equal to a threshold ($R_{NEGth}$), which is also dynamically adjusted in a manner to be described below. Blocks 1346 and 1348 check whether $NEG_{edge}$ and $POS_{edge}$, respectively, are "yes". In block 1350, the $NEG_{edge}$ variable is set to "yes" to indicate that a downstroke has been found and the $R_{width}$ is reset to 0 to begin tracking the width of what is possibly an R wave. In block 1354, and the $NEG_{edge}$ variable is set to "yes" and the $POS_{edge}$ variable is set to "no" to indicate that a downstroke has been found. Block 1352 is identical to block 1332. Block 1356 is identical to block 1336 except that peak of the carat shaped (^) R wave, i.e. the j for which S(j) is largest, is found rather than the bottom of the v.

Returning to block 1304, if the end of the segment has been reached, control passes to block 1306, which calculates the positive and negative slope thresholds ($R_{POSth}$ and $R_{NEGth}$) to be used for the next segment. These thresholds are determined by computing a weighted average of the current threshold and specified fraction of the 8 largest slopes. For example, for the case of $R_{POSth}$, the weighted average is 7*current $R_{POSth}$/8+x/8, where x is equal to a programmable fraction ($P_{THRESH}$/128) of the average of the current segment's 8 largest slopes, which in turn is sum of the 8 most positive slopes in the segment divided by 8. The calculated values are checked and adjusted if necessary to make sure they don't change too quickly or get too close to 0. Specifically, for the case of $R_{POSth}$, the computed $R_{POSth}$ is compared to the old $R_{POSth}$ plus MaxAwayFrom0, a programmable parameter that serves as an upper bound to how much $R_{POSth}$ is allowed to increase from segment to segment. If $R_{POSth}$ is larger than the old $R_{POSth}$ plus MaxAwayFrom0, then $R_{POSth}$ is set equal to the old $R_{POSth}$ plus MaxAwayFrom0. Similarly, if the computed $R_{POSth}$ indicates a rapid decrease, $R_{POSth}$ is set equal to the old $R_{POSth}$ minus MaxToward0, a programmable parameter that serves as an upper bound to how much $R_{POSth}$ is allowed to decrease from segment to segment. And finally, $R_{POSth}$ is not allowed to shrink below 32. The procedure for $R_{NEGth}$ is analogous. The preferred value for MaxAwayFrom0 is 10 and the preferred value for MaxToward0 is 255 (effectively disabling this limit).

An alternate to ST shift detection is to process just the T wave, which can change its peak or average amplitude rapidly if there is a heart attack. The T wave can, however change its amplitude slowly under normal conditions so a T wave shift detector would need a much shorter time U than that of a detector using the ST segment before the T wave. If the detector is checking for such T wave shift, i.e. a voltage shift of the T wave part of the ST segment, then it may be desirable to check against a baseline where U is 1 to 30 minutes and W is 15 seconds to 15 minutes. For example, U=3 minutes and W=15 seconds is a preferred setting to catch a quickly changing T wave. This would also allow use of recent electrogram segments stored in the recent electrogram memory of FIG. 4 as baseline electrogram segments for T wave shift detection. It is envisioned that the programmer 68 of FIG. 1 would allow the patient's doctor to program the cardiosaver 5 to use ST segment shift or T wave shift detectors by themselves, or together simultaneously. If both were used then the programmer 68 would allow the patient's doctor to choose whether a positive detection will result if either technique detects an event or only if both detect an event.

The parameters Y, $P_{COLLECT}$, $P_{COLLECT2}$, U and W are stored with the programmable parameters 471 in the RAM 47 in FIG. 4. These parameters may be permanently set at the time of manufacturing of the cardiosaver 5 or they may be programmed through the programmer 68 of FIG. 1. The calculated criteria for cardiac event detection extracted from the baseline electrogram segments stored in baseline electrogram memory 474 are stored in the calculated baseline data memory 475 of the RAM 47.

Although it may be effective to fix the values of time offsets $T_{PQ}$ (502) and $T_{ST}$ (504) and the durations $D_{PQ}$ (506) and $D_{ST}$ (508), it is envisioned that the time offsets $T_{PQ}$ and $T_{ST}$ and the durations $D_{PQ}$ and $D_{ST}$ could be automatically adjusted by the cardiosaver 5 to account for changes in the patient's heart rate. If the heart rate increases or decreases, as compared with the patient's normal heart rate, it envisioned that the offsets $T_{PQ}$ (502) and $T_{ST}$ (504) and/or the durations $D_{PQ}$ (506) and $D_{ST}$ (508) could vary depending upon the R-R interval between beats or the average R-R interval for an electrogram segment. A simple technique for doing this would vary the offsets $T_{PQ}$ and $T_{ST}$ and the durations $D_{PQ}$ and $D_{ST}$ in proportion to the change in R-R interval. For example if the patient's normal heart rate is 60 beats per minute, the R-R interval is 1 second; at 80 beats per minute the R-R interval is 0.75 seconds, a 25% decrease. This could automatically produce a 25% decrease in the values of $T_{PQ}$, $T_{ST}$, $D_{PQ}$ and $D_{ST}$. Alternately, the values for $T_{PQ}$, $T_{ST}$, $D_{PQ}$ and $D_{ST}$ could be fixed for each of up to 20 preset heart rate ranges. In either case, it is envisioned that after the device has been implanted, the patient's physician would, through the programmer 68 of FIG. 1, download from the cardiosaver 5 to the programmer 68, a recent electrogram segment from the recent electrogram memory 472. The physician would then use the programmer 68 to select the values of $T_{PQ}$, $T_{ST}$, $D_{PQ}$ and $D_{ST}$ for the heart rate in the downloaded recent electrogram segment. The programmer 68 would then allow the physician to choose to either manually specify the values of $T_{PQ}$, $T_{ST}$, $D_{PQ}$ and $D_{ST}$ for each heart rate range or have the cardiosaver 5 automatically adjust the values of $T_{PQ}$, $T_{ST}$, $D_{PQ}$ and $D_{ST}$ based on the R-R interval for each beat of any electrogram segment collected in the future by the cardiosaver 5. It is also envisioned that only the offset times, $T_{PQ}$ and $T_{ST}$, might be automatically adjusted and the durations $D_{PQ}$ and $D_{ST}$ would be fixed so that the average values of the ST and PQ segments $V_{PQ}$ (512), $V_{ST}$ (514), $V'_{PQ}$ (512') and $V'_{ST}$ (514') would always use the same number of data samples for averaging.

When used in pacemakers or combination pacemaker/ICDs it envisioned that the start time $T_{ST}$ and duration $D_{ST}$ of the ST segment may have different values than during sinus rhythm (when the pacemaker is not pacing) as pacing the heart changes the characteristics of ischemic ST shifts causing them to occur later relative to the start of the R wave. It is also envisioned, that the offset for the start of the ST segment may be better measured from the S Wave instead of the R wave used for sinus rhythm when the pacemaker is not pacing. The technique of using different timing parameters for start and duration when pacing can be applied to analysis of any sub-segment of the electrogram including the sub-segment that includes the T wave peak.

It is also envisioned that the patient would undergo a stress test following implant. The electrogram data collected by the implant 5 would be transmitted to the programmer 68 of FIG. 1, and one or more of the parameters $T_{PQ}$ (502), $T_{ST}$ (504), $D_{PQ}$ (506) and $D_{ST}$ (508) of FIG. 6 would be automatically selected by the Programmer based on the electrogram data from the stress test. The data from the stress test should cover multiple heart rate ranges and would also be used by the programmer 68 to generate the excessive ST shift detection percentage thresholds $P_{ST}$ for each of the heart rate ranges. In each case where the programmer 68 automatically selects parameters for the ST shift detection algorithm, a manual override would also be available to the medical practitioner. Such an override is of particular importance as it allows adjustment of the algorithm parameters to compensate for missed events or false positive detections.

The S wave peak voltage $V_S$ (507) is also shown on the baseline beat 500 in FIG. 6. While the preferred embodiment of the present invention uses an average ΔR(avg) of the average PQ to R wave amplitudes ΔR(i) as the normalization voltage for setting the threshold for ST shift detection, it is also envisioned that normalization voltage could be the average of the entire R wave to S wave amplitude ($V_R$–$V_S$) or it could be the larger of ΔR(i) or the PQ to S amplitude ΔS(i)= $V_S$–$V_{PQ}$. It is important to note here that the threshold for ST shift detection is set as a percentage of the average of baseline average signal amplitudes. This is important because the baseline signal is only collected if the electrogram is normal and therefore the thresholds would not be affected by transient changes in signal amplitude (e.g. R wave height) that can occur during an ST elevation myocardial infarction. Therefore, for the purposes of the present invention the threshold is calculated as a percentage of an average of the signal amplitude of U baselines. In turn, the signal amplitude of each of the U baselines is the average signal amplitude of at least two beats of the baseline electrogram segment where the average signal amplitude of a baseline segment can be any of the following:

the average PQ segment to R voltage difference ΔR(i),
the peak-to-peak voltage of the beat (i.e. the R to S wave voltage difference) ($V_R$–$V_S$),
the average PQ segment to S wave voltage difference ΔS(i),
the larger of ΔR(i) or ΔS(i), or
any average signal amplitude calculated from at least two beats of the baseline electrogram segment.

One embodiment of ST shift and T wave shift detection might use a baseline for ST shift detection that is an average of the baselines over the 24±½ hour period before and a baseline for T wave shift that is 1 to 4 minutes in the past. This would require that the baseline extraction subroutine 835 be run for T wave shift parameters approximately every 60 seconds and for ST segment parameters every hour.

Figure 14:
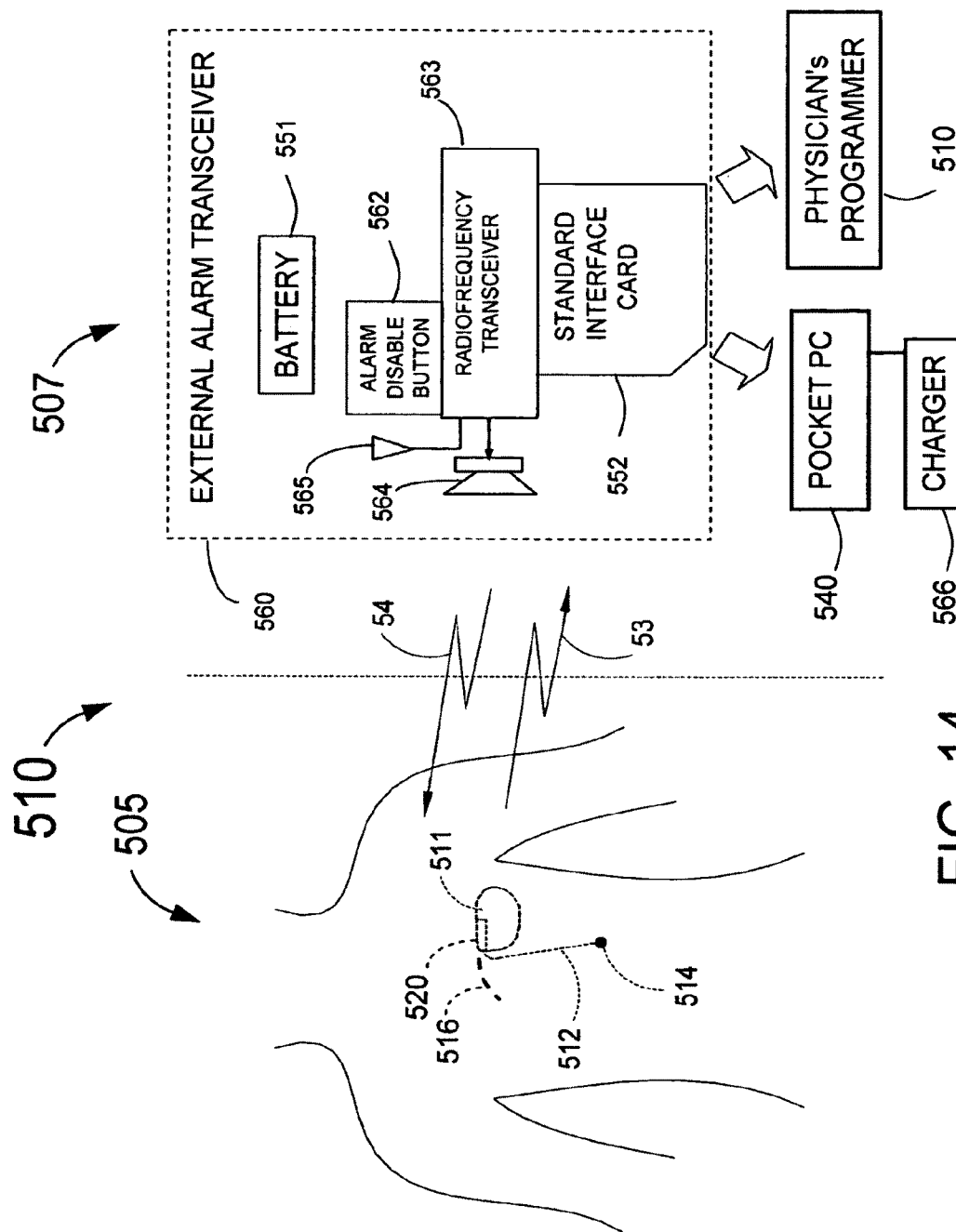
FIG. 14 is an alternate embodiment of the guardian system.

FIG. 14 shows a modified embodiment of the guardian system 510. The cardiosaver implant 505 with lead 512, electrode 514, antenna 516, header 520 and metal case 511 would be implanted subcutaneously in a patient at risk of having a serious cardiac event such as an acute myocardial infarction. The lead 512 could be placed either subcutaneously or into the patient's heart. The case 511 would act as the indifferent electrode. The system 510 also included external equipment that includes a physician's programmer 510 an external alarm transceiver 560 and a pocket PC 540 with charger 566. The external alarm transceiver 560 has its own battery 561 and includes an alarm disable button 562 radiofrequency transceiver 563, speaker 564, antenna 565 and standard interface card 552. The cardiosaver 505 has the same capabilities as the cardiosaver 5 of FIGS. 1 through 4.

The standardized interface card 552 of the external alarm transceiver 510 can be inserted into a standardized interface card slot in a handheld or laptop computer. The pocket PC 540 is such a handheld computer. The physician's programmer 510 is typically a laptop computer. Such standardized card slots include compact flash card slots, PCMCIA adapter (PC adapter) card slots, memory stick card slots, Secure Digital (SD) card slots and Multi-Media card slots. The external alarm transceiver 510 is designed to operate by itself as a self-contained external alarm system, however when inserted into the standardized card slot in the pocket PC 540, the combination forms an external alarm system with enhanced functionality. For example, in stand alone mode without the pocket PC 540, the external alarm transceiver 560 can receive alarm notifications from the cardiosaver implant 505 and can produce an external alarm signal by generating one or more sounds through the speaker 564. These sounds can wake the patient up or provide additional alerting to that provided by the internal alarm signal generated by the cardiosaver 505. The alarm disable button 562 can acknowledge and turn off both external and internal alarm signals. The standalone external alarm transceiver 560 therefore provides key functionality could be small enough to wear on a chain around the neck or on a belt.

When plugged into the pocket PC 540, the external alarm transceiver 560 can facilitate the display of text messages to the patient and electrogram data that is transmitted from the cardiosaver 505. The pocket PC 540 also enables the patient operated initiator 55 and panic button 52 capabilities of the external alarm system 60 of FIG. 1. Being a pocket PC also readily allows connection to wireless communication capabilities such as wireless internet access that will facilitate retransmission of data to a medical practitioner at a geographically remote location. It is also envisioned that the charger 566 could recharge the batter 551 when the external alarm adapter 560 is plugged into the pocket PC 540.

The external alarm transceiver 560 can also serve as the wireless two-way communications interface between the cardiosaver 505 and the programmer 510. The physician's programmer 510 is typically a laptop computer running some version of the Microsoft Windows operating system. As such, any or the above standardized slot interfaces can be either directly interfaced to such a laptop computer or interfaced using a readily available conversion adapter. For example, almost all laptop computers have a PCMCIA slot and PCMCIA card adapters are available for compact flash cards, Secure Digital cards etc. Thus the external alarm adapter 560 could provide the interface to the physician's programmer 510. This provides additional security as each cardiosaver implant 505 and external alarm adapter 560 could be uniquely paired with built in security codes so that to program the implant 505, the physician would need the patient's external alarm adapter 560 that would act both as a wireless transceiver and as a security key.

Although the guardian system 10 as described herein could clearly operate as a stand-alone system, it is clearly conceivable to utilize the guardian system 10 with additional pacemaker or implanted defibrillator circuitry. As shown in FIG. 4, pacemaker circuitry 170 and/or defibrillator circuitry 180 could be made part of any cardiosaver 5 or 505. Furthermore, two separate devices (one pacemaker or one defibrillator plus one cardiosaver 5) could be implanted within the same patient.

Figure 15:
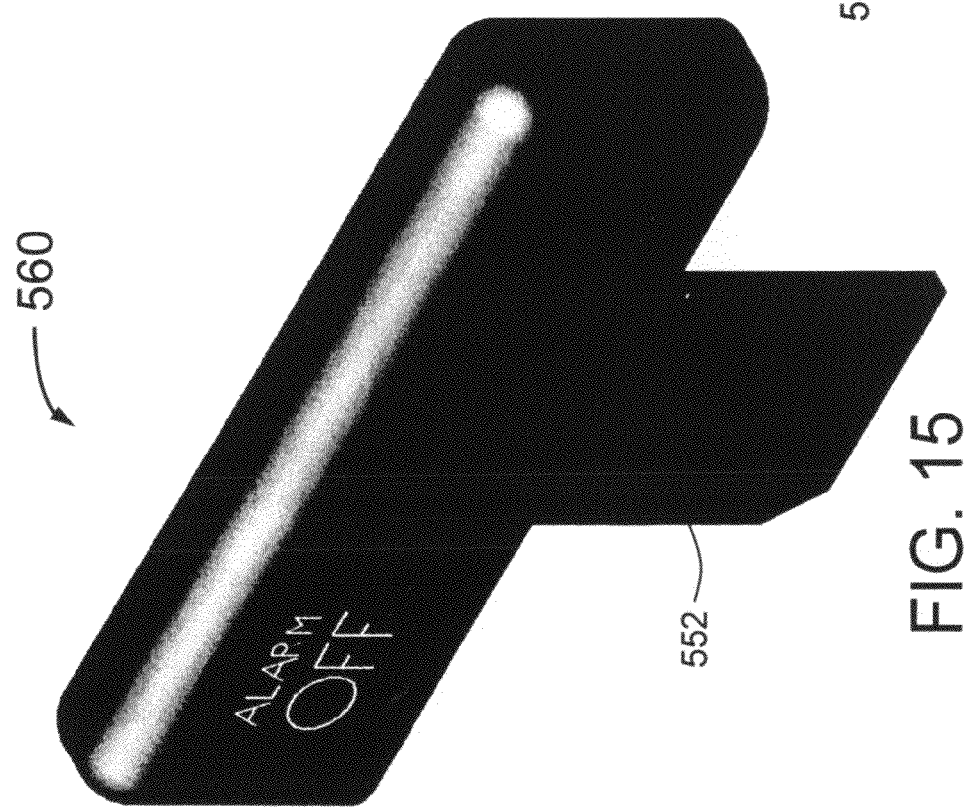
FIG. 15 illustrates the preferred physical embodiment of the external alarm transceiver.

FIG. 15 illustrates a preferred physical embodiment of the external alarm transceiver 560 having standardized interface card 552, alarm disable button 562 labeled "ALARM OFF" and speaker 564. It is also envisioned that by depressing and holding the alarm disable button 562 for a minimum length of time, when there is not an alarm, the external alarm transceiver could verify the operational status of the cardiosaver 505 and emit a confirming sound from the speaker 564.

Figure 16:
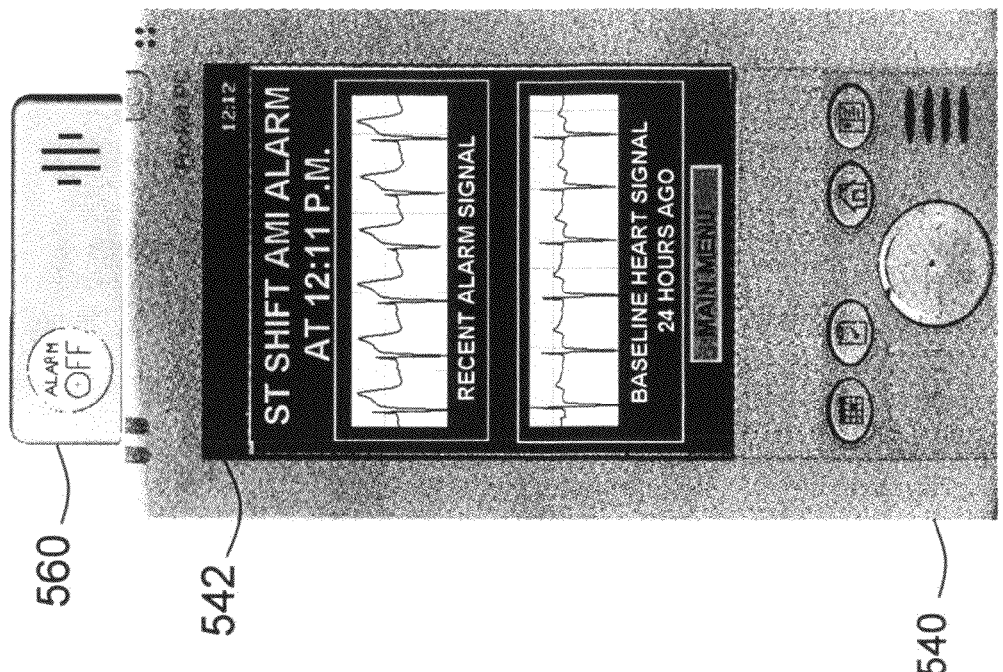
FIG. 16 illustrates the physical embodiment of the combined external alarm transceiver and pocket PC.

FIG. 16 illustrates the physical embodiment of the combined external alarm transceiver 560 and pocket PC 540 where the standardized interface card 552 has been inserted into a matching standardized interface card slot the pocket PC 540. The screen 542 of the pocket PC 540 shows an example of the display produced by an external alarm system following the detection of an acute myocardial infarction by the cardiosaver 505. The screen 542 of FIG. 15 displays the time of the alarm, the recent electrogram segment from which the cardiac event was detected and the baseline electrogram segment used for comparison in the cardiac event detection. Such a display would greatly facilitate diagnosis of the patient's condition upon arrival at an emergency room and could eliminate the need for additional electrocardiogram measurements before the patient is treated.

Figure 17:
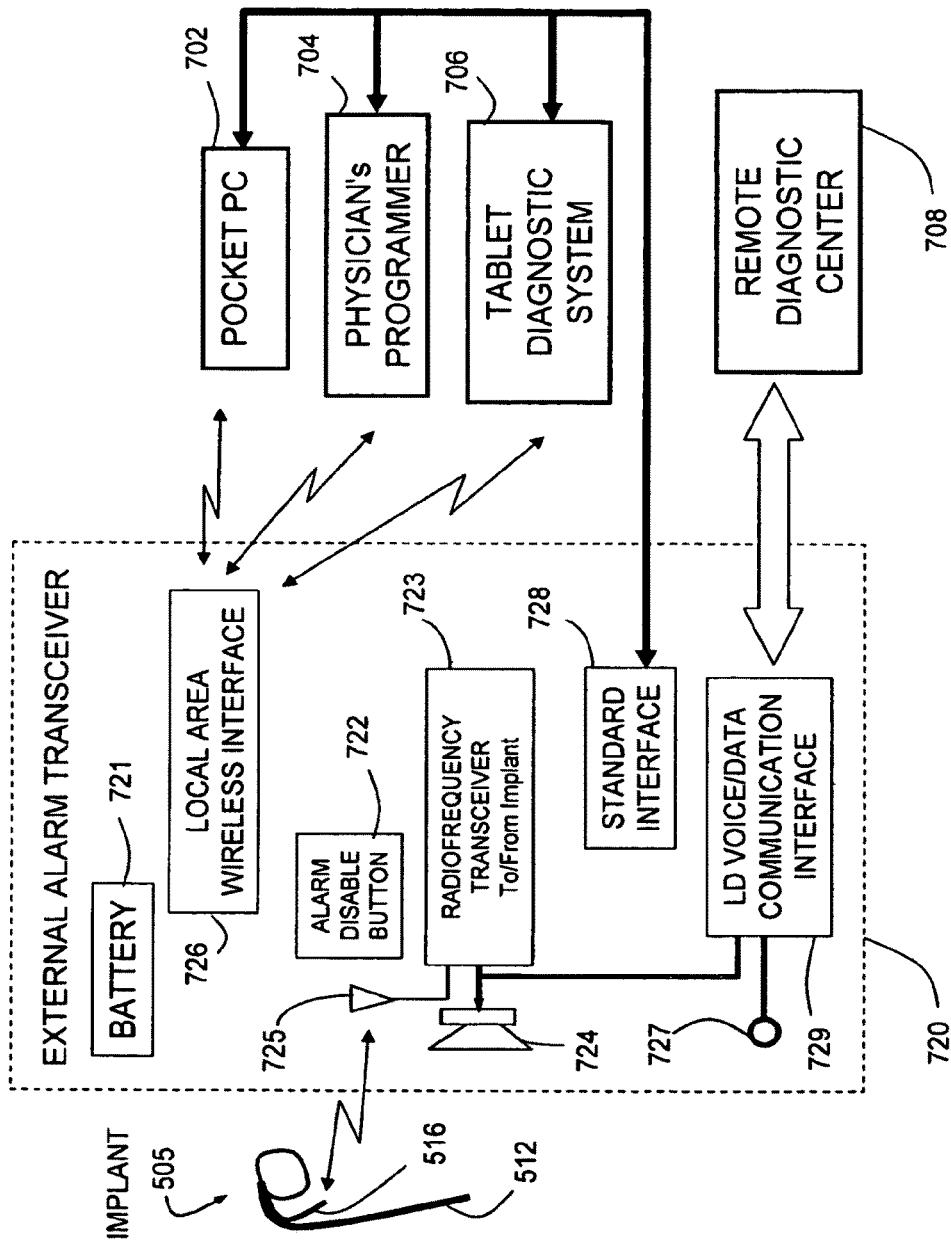
FIG. 17 shows an advanced embodiment of the external alarm transceiver.

FIG. 17 shows an advanced embodiment of the external alarm transceiver 720 having a battery 721, an alarm disable button 722, a RF transceiver for data communication to and from the implanted device, a loudspeaker 724, a microphone 727, a local area wireless interface 723, a standard interface 728 and a long distance (LD) voice/data communication interface 729. The function of the alarm disable button 722 and the radiofrequency transceiver 723 are as described for the similar devices shown in FIG. 13.

The local area wireless interface 723 provides wireless communication within a building (e.g. home, doctor's office or hospital) to and from the implant 505 with lead 512 and antenna 516 through the external alarm transceiver 720 from and to assorted external equipment such as Pocket PCs 702, Palm OS PDAs, Notebook PCs, physician's programmers 704 and tablet diagnostic systems 706. The means for transmission from the local area wireless interface 723 may be by radiofrequency or infra-red transmission. A preferred embodiment of the local area wireless interface 723 would use a standardized protocol such as IRDA with infra-red transmission and Bluetooth or WiFi (802.11.a, b, or g) with radiofrequency transmission. The local area wireless interface 723 would allow display of implant data and the sending of commands to the implant 505.

The standard interface 728 provides a physical (wired) connection for data communication with devices nearby to the patient for the purposes of displaying data captured by the implant 505 and for sending commands and programs to the implant 505. The standard interface 728 could be any standard computer interface; for example: USB, RS-232 or parallel data interfaces. The pocket PC 702 and physician's programmer 704 would have functionality similar to the pocket PC 540 and physician's programmer 510 of FIG. 13.

The tablet diagnostic system 706 would provide a level of functionality between that of the pocket PC 702 and physician's programmer 706. For example, the tablet diagnostic system would have the programmer's ability to download complete data sets from the implant 505 while the pocket PC is limited to alarm and baseline electrogram segments or the most recent electrogram segment. The tablet diagnostic system 706 would be ideal for an emergency room to allow emergency room medical professionals to quickly view the electrogram data stored within the implant 505 to assess the patient's condition. The recently introduced Tablet PCs such as the Toshiba Portege 3500 or the Compaq TC1000 have IRDA, WiFi and USB interfaces built into them and so would make an ideal platform for the tablet diagnostic system 706. It is envisioned that such a tablet diagnostic system in an emergency room or medical clinic would preferably be connected to its own external alarm transceiver. The tablet diagnostic system 706 could be hand held or mounted on a wall or patient bed. A unit located near the bed of an incoming patient having a guardian implant 505 would enable display of patient diagnostic data without requiring any attachments to the patient. Such wireless diagnosis is similar to that envisioned for the tricorder and diagnostic beds of the Star Trek science fiction series created by Gene Roddenberry.

The long distance voice/data communication interface 729 with microphone 727 and also attached to the loudspeaker 724 will provide the patient with emergency contact with a remote diagnostic center 708. Such a system could work much like the ONSTAR emergency assistance system now built into may cars. For example, when a major or EMERGENCY alarm is identified by the guardian implant 505, the following steps could be followed:

1. The guardian will first ascertain if an external alarm transceiver is within range, if not the internal alarm will be initiated.
2. If the external alarm transceiver is within range the system will next see if there is access to the remote diagnostic center 708 through the long distance voice/data communication interface 729. If not the external alarm transceiver 720 and implant 505 will initiate internal and/or external alarm notification of the patient.
3. If there is access to the remote diagnostic center 708 the long distance voice/data communication interface 729, the patient alarm information including alarm and baseline electrogram segments will be transmitted to the remote diagnostic center 708. A medical professional at the remote diagnostic center 708 will view the data and immediately establish voice communication to the external alarm transceiver 720 through the long distance voice/data communication interface 729. If this occurs, the first thing that the patient will hear is a ringing tone and/or a voice announcement followed by the contact with the medical professional who can address the patient by name and facilitate appropriate emergency care for the patient. In this case, the internal and external alarms will not be needed and to the patient it will resemble an incoming telephone call from the medical professional. It is also envisioned that the voice of the medical professional could be the first thing that the patient hears although an initial alerting signal is preferred.

This method of establishing the highest level of communication available to the guardian system with the fall back of just the internal alarm will provide the best possible patient alerting based on what is available at the time of the alarm.

The data communications between the external alarm transceiver 720 and the remote diagnostic center 708 would utilize a standardized (or custom) data communications protocol. For example, the data communications might utilize any or all of the following either within a private network, a VPN, an intranet (e.g. a single provider network such as the Sprint data network) or through the public internet:

1. Basic TCP/IP messaging within a single network or through the internet.
2. Short Messaging Service (SMS)

3. Multimedia Message Service (MMS) used for cell phone transmission
4. Universal Datagram Protocol (UDP)

It is also envisioned that the present invention would take advantage of existing telephone network call center technology including use of Automatic Number Identification (ANI) to identify the incoming call, and Dialed Number Identification Service (DNIS) where different numbers might be dialed by the external alarm transceiver 720 depending on the severity of the detected cardiac event. For example, in the case where the call is placed by the emergency alarm transceiver 720, an EMERGENCY alarm might dial a different number than a SEE DOCTOR alert which might be different from a patient-initiated "panic button" call. DNIS could help get the appropriate help for the patient even if data connectivity is unavailable and might be used to prioritize which call is answered first (e.g., an EMERGENCY alarm would have higher priority than a SEE DOCTOR alert).

It is also envisioned that the remote diagnostic center 708 could facilitate the scheduling of an appointment with the patient's doctor following a SEE DOCTOR alert.

Although throughout this specification all patients have been referred to in the masculine gender, it is of course understood that patients could be male or female. Furthermore, although the only electrogram indications for an acute myocardial infarction that are discussed herein are shifts involving the ST segment and T wave height, it should be understood that other changes in the electrogram (depending on where in the heart the occlusion has occurred and where the electrodes are placed) could also be used to determine that an acute myocardial infarction is occurring. Furthermore, sensors such as heart motion sensors, or devices to measure pressure, $pO_2$ or any other indication of an acute myocardial infarction or cardiac events could be used independently or in conjunction with a ST segment or T wave shift detectors to sense a cardiac event.

It is also envisioned that all of the processing techniques described herein for an implantable cardiosaver are applicable to a guardian system configuration using skin surface electrodes and a non-implanted cardiosaver 5 the term electrogram would be replaced by the term electrocardiogram. Thus the cardiosaver device described in FIGS. 5 through 12 would also function as a monitoring device that is completely external to the patient.

Figure 18:
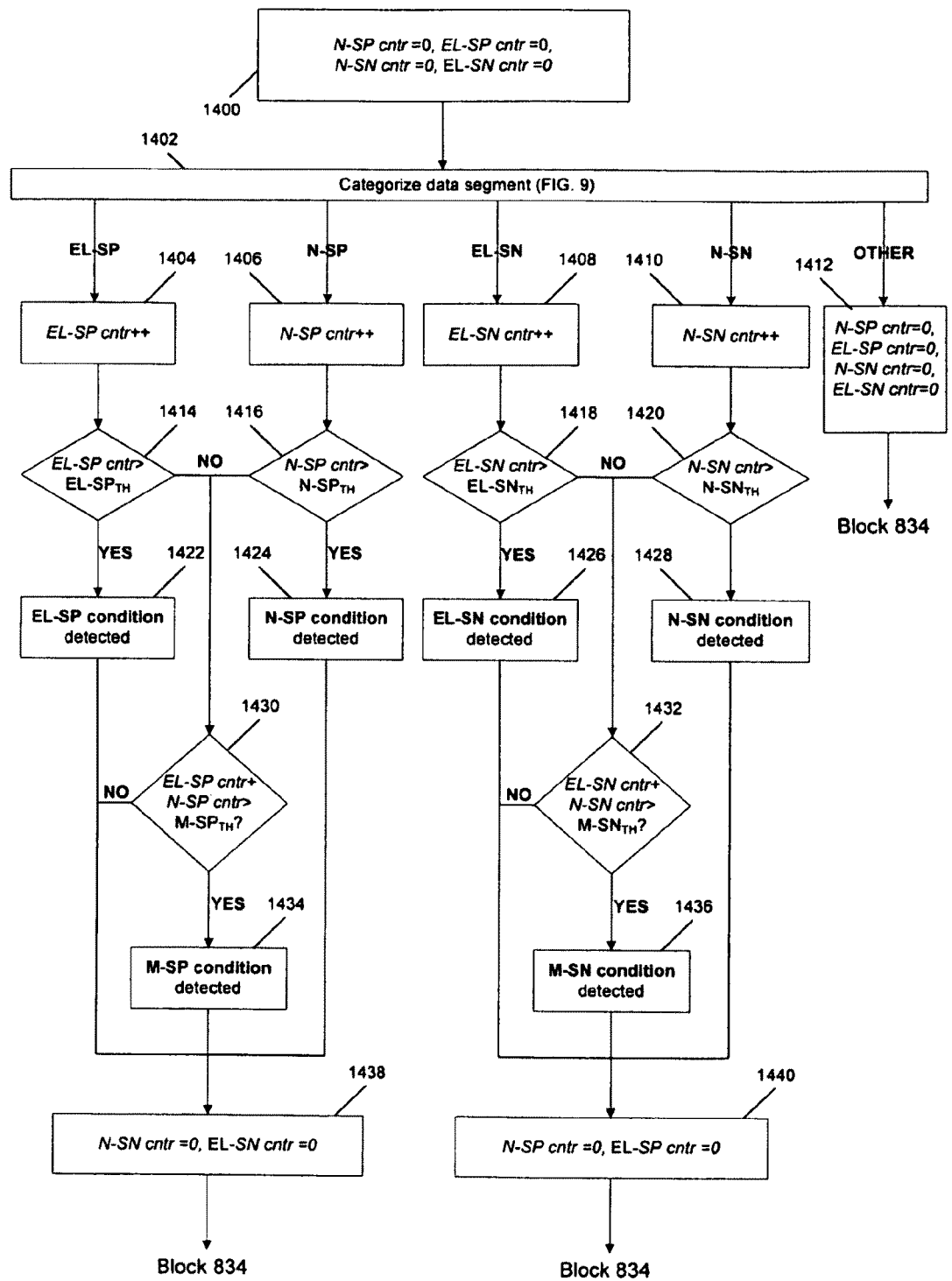
FIG. 18 is an alternate scheme for detecting ST shift related conditions that may be used in conjunction the cardiosaver event detection program shown in FIG. 5.

FIG. 18 is an alternate scheme for detecting ST shift related conditions that may be used in conjunction the cardiosaver event detection program shown in FIG. 5. The routine shown in FIG. 18 performs different tests for detecting ST shift conditions depending on the polarity of the ST shift (positive or negative) and heart rate. With a "can to tip" lead orientation, positive ST shifts may necessarily indicate a severe type of ischemia arising from an acute blockage of a coronary artery. On the other hand, negative ST shifts could result either from such an acute blockage or from exercise/higher heart rates.

Furthermore, the inventors' work has shown that, when a heart rate returns to the normal range after being elevated, negative ST shifts as recorded by a "can to tip" electrode often persist for a number of minutes. The program shown in FIG. 18 allows this "exercise induced" ischemia condition to be distinguished from a case in which a negative ST shift lasts for a long time at low heart rates, which may be indicative of a more severe form of ischemia.

To track both the polarity of ST shifts and heart rate, the program shown in FIG. 18 includes four counters, N-SP, EL-SP, N-SN and EL-SN. N-SP and EL-SP count the number of segments with positive ST shifts at normal and elevated heart rates, respectively. N-SN and EL-SN count the number of segments with negative ST shifts at normal and elevated heart rates, respectively. All of these counters are initialized to 0 in block 1400, which may be added to the initialization block 800 in FIG. 5.

After a segment is acquired (see block 802 of FIG. 5), it is categorized in block 1402 (analogous to block 804 of FIG. 5). If the segment is characterized by a positive shift, control is transferred to block 1404 or block 1406 according to whether the segment is N-SP or EL-SP. If the segment is characterized by a negative shift (N-SN or EL-SN), control is transferred to block 1408 or block 1410 according to whether the segment is N-SN or EL-SN. If the segment is not ST shifted, control is transferred to block 1412.

In blocks 1404 and 1406 the EL-SP cntr and the N-SP cntr are incremented respectively. In blocks 1414 and 1416, respectively, the EL-SP cntr and the N-SP cntr are checked against programmable thresholds EL-$SP_{TH}$ and N-$SP_{TH}$ respectively. N-$SP_{TH}$ is preferably set to 3, which means that positive shifts at normal heart rates will trigger an N-SP detectable condition within 90 segments at the normal 30 second acquisition interval. A longer amount of time, preferably five minutes (EL-$SP_{TH}$, =300 s/30 s=10), may be required to trigger a detectable condition at higher rates. Blocks 1422 and 1424 respectively set flags indicating the detection of a positive shift for elevated and normal heart rates, respectively.

It is possible for a positive ST shift to persist during a transition of the heart rate between normal and elevated. In this case, it may be desirable to detect a positive shift condition, even if neither the N-SP cntr nor the EL-SP cntr have reached threshold. To effect such a detection, block 1430 compares the number of consecutive positive ST shifted segments, the sum of the N-SP cntr and the EL-SP cntr, is compared to a threshold M-$SP_{TH}$ for mixed heart rate positive ST shifts, and a mixed heart rate shift condition is flagged in block 1434 if the sum exceeds the threshold. If N-$SP_{TH}$ is set at a small value, such as its preferred value of 3, step 1430 is not important.

In block 1438, the negative shift counters N-SN cntr or EL-SN cntr are reset to 0. This step ensures that the system can keep track of the number of consecutive negative ST shifted segments.

After block 1438, control passes to block 834 of FIG. 5. It will be appreciated that the additional condition detection described with reference to FIG. 5 may be performed in conjunction with the ST polarity and heart rate routine shown in FIG. 18.

The steps for processing negative ST shifts are analogous to the steps for processing positive ST shifts. In blocks 1408 and 1410, respectively, the EL-SN cntr and N-SN cntr, respectively, are incremented. In blocks 1418 and 1420, respectively, the EL-SN cntr and N-SN cntr, respectively, are compared to programmable normal and elevated thresholds EL-$SN_{TH}$ and N-$SN_{TH}$ respectively. With a "can to tip" lead orientation, it may be desirable to make the thresholds N-$SN_{TH}$ and EL-$SN_{TH}$ longer than the corresponding positive ST thresholds N-$SN_{TH}$ and EL-$SN_{TH}$. N-$SN_{TH}$ is preferably set to approximately 5 minutes. In the case where a negative ST shift persist or worsens after exercise (or more generally a transition from a high heart rate to a low heart), 5 minutes may allow the negative shift to resolve. At higher heart rates, a longer threshold may be desirable, a preferred value for .EL-$SN_{TH}$ being approximately, 15 minutes (the effective length of time required to trigger a persistent ischemia condition in block 862 of FIG. 5).

EL-SN and N-SN flags are set in blocks 1426 and 1428 respectively. The mixed heart rate condition for a negative shift is checked in block 1432 and a flag is set as appropriate in block 1436. Analogously to block 1438, in block 1440, the positive shift counters N-SP cntr or EL-SP cntr are reset to 0. Processing continues with block 834 of FIG. 5.

Returning to block 1402, if the current segment is not shifted, in block 1412, the four ST counters are reset to 0. Processing continues with block 834 of FIG. 5.

Figure 19:
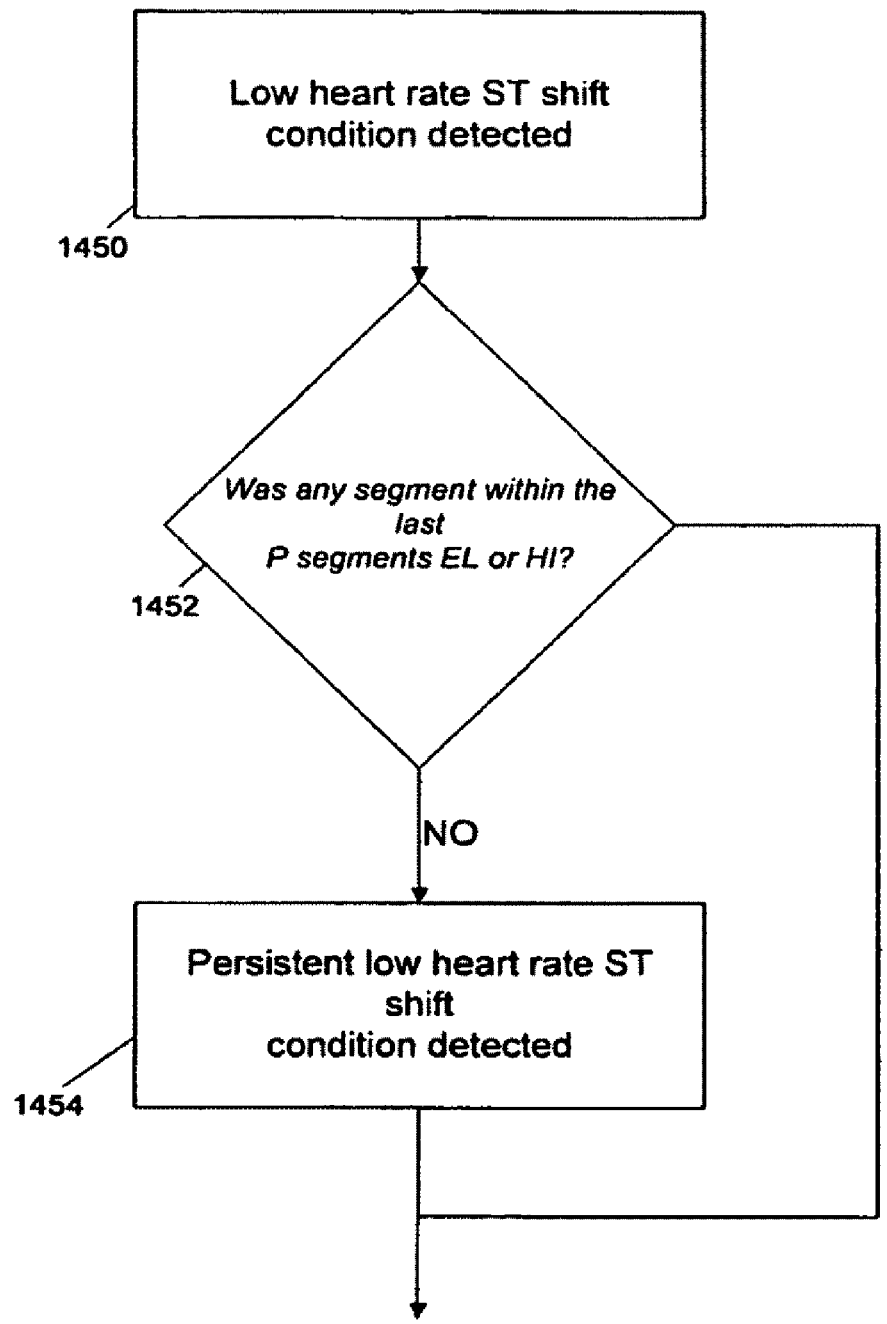
FIG. 19 is yet an alternate scheme for detecting ST shift related conditions that may be used in conjunction the cardiosaver event detection program shown in FIG. 5.

An alternative method for handling the case where a negative ST shift temporarily persist or worsens after exercise (or more generally a transition from a high heart rate to a low heart), involves checking whether a high heart rate condition preceded an ST depression that occurred at a low heart rate. FIG. 19 is a block diagram of an embodiment of this method, which may be implemented in conjunction with the program shown in FIG. 5.

In block 1450, a low heart rate ST shift condition has been detected. In block 1452, the routine checks whether any of the last P segments was characterized by an elevated or high heart rate. If so, then a persistent low heart rate ST shift condition is not detected and block 1454 is skipped. P may be set according to the time after cessation of exercise/high heart rate that exercise induced ST shifts resolve, the interval between segment acquisition, and the number of consecutive segments required to trigger detection of a low heart rate with ST shift condition. If there is a 90 second interval between the last sample at a high heart rate and the first sample at a normal heart rate, 30 seconds between subsequent acquisitions, then (P−1)*30+90 seconds will have elapsed between the last high heart rate segment and the current segment, assuming the first low heart rate segment and all subsequent segments are above the threshold for detecting ST shifts at normal heart rates. If it is desired to have at 5 minute window after a high heart rate before triggering detection of a persistent low heart rate ST shift condition, then P should be set to 8.

In an alternate embodiment, a normal heart rate segment could be reclassified as a high heart rate segment within a certain window after the patient's heart rate has changed from high to normal. In this case, the high heart rate ST shift thresholds would be applied to the reclassified segment.

Various other modifications, adaptations, and alternative designs are of course possible in light of the above teachings. Therefore, it should be understood at this time that, within the scope of the appended claims, the invention can be practiced otherwise than as specifically described herein.

What is claimed is:

1. A cardiac event detection system for detecting a cardiac event in a patient comprising:
    (a) at least two electrodes for sensing an electrogram electrical signal from said patient's heart;
    (b) an implantable device coupled to said electrodes, said implantable device having an analog-to-digital circuit system contained therein for digitizing said electrogram electrical signal to produce electrogram segments;
    (c) a processor contained in said implantable device and electrically coupled to said electrodes, said processor including means for determining whether an electrogram segment qualifies as a baseline segment, said processor further including means for tracking the failure of electrogram segments to qualify as baseline electrogram segments.

2. The system of claim 1 wherein the means for tracking includes means for determining whether no electrogram segments have qualified as a baseline electrogram segment over a baseline alert time period.

3. The system of claim 2 where implanted device includes patient alerting means which are activated following determination that no electrogram segments have qualified as a baseline electrogram segment over the baseline alert time period.

4. The system of claim 2 wherein the inability to collect a baseline electrogram segment is caused by the patient's heart rate being higher than a preset normal heart rate range.

5. The system of claim 2 wherein the inability to collect a baseline electrogram segment is caused by the patient's heart rate being lower than a preset normal heart rate range.

6. The system of claim 2 wherein the inability to collect a baseline electrogram segment is caused by the patient's heart rate being irregular than a preset normal heart rate range.

7. The system of claim 2 wherein the inability to collect a baseline electrogram segment is caused by the patient's electrogram segments having too many abnormal beats to qualify as a baseline electrogram segment.

8. The system of claim 2 wherein at least one of the electrodes is located within the heart.

9. The system of claim 8 wherein the electrode located within the heart is located within the right ventricle.

10. The system of claim 1 wherein at least one electrode is located subcutaneously.

* * * * *